(12) United States Patent
Li et al.

(10) Patent No.: US 11,884,725 B2
(45) Date of Patent: Jan. 30, 2024

(54) ANTIBODY AGAINST TIM-3 AND APPLICATION THEREOF

(71) Applicant: AMPSOURCE BIOPHARMA SHANGHAI INC., Shanghai (CN)

(72) Inventors: Qiang Li, Shanghai (CN); Tongtong Xue, Chengdu (CN); Yuncheng Zheng, Shanghai (CN); Liang Xiao, Chengdu (CN); Dengnian Liu, Chengdu (CN); Jianyu Sun, Shanghai (CN); Jiangjiang Hu, Chengdu (CN); Xinlu Ma, Shanghai (CN); Kangyong Zhu, Shanghai (CN); Yuanli Li, Shanghai (CN)

(73) Assignee: Ampsource Biopharma Shanghai Inc., Shanghai (CN)

( * ) Notice: Subject to any disclaimer, the term of this patent is extended or adjusted under 35 U.S.C. 154(b) by 660 days.

(21) Appl. No.: 17/050,161

(22) PCT Filed: Apr. 22, 2019

(86) PCT No.: PCT/CN2019/083727
§ 371 (c)(1),
(2) Date: Oct. 23, 2020

(87) PCT Pub. No.: WO2019/206095
PCT Pub. Date: Oct. 31, 2019

(65) Prior Publication Data
US 2021/0238282 A1 Aug. 5, 2021

(30) Foreign Application Priority Data
Apr. 24, 2018 (CN) .......................... 201810371407.3

(51) Int. Cl.
*C07K 16/28* (2006.01)
*A61P 35/00* (2006.01)
*A61K 45/06* (2006.01)
*A61K 39/00* (2006.01)
*C12N 5/12* (2006.01)

(52) U.S. Cl.
CPC .......... *C07K 16/2803* (2013.01); *A61K 45/06* (2013.01); *A61P 35/00* (2018.01); *C12N 5/12* (2013.01); *A61K 2039/507* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein | |
| 3,850,752 A | 11/1974 | Schuurs | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 10/1988 | Tom et al. | |
| 4,816,567 A | 3/1989 | Cabilly et al. | |
| 4,946,778 A | 8/1990 | Ladner et al. | |
| 5,225,539 A | 7/1993 | Winter | |
| 5,260,203 A | 11/1993 | Ladner et al. | |
| 5,530,101 A | 6/1996 | Queen et al. | |
| 5,585,089 A | 12/1996 | Queen et al. | |
| 5,624,821 A | 4/1997 | Winter et al. | |
| 5,648,260 A | 7/1997 | Winter et al. | |
| 5,693,762 A | 12/1997 | Queen et al. | |
| 6,180,370 B1 | 1/2001 | Queen et al. | |
| 9,605,070 B2 | 3/2017 | Sabatos-Payton et al. | |
| 10,550,181 B2 | 2/2020 | Takayanagi et al. | |

FOREIGN PATENT DOCUMENTS

| | | |
|---|---|---|
| EP | 0173494 A3 | 11/1987 |
| EP | 0388151 A1 | 9/1990 |
| EP | 0184187 B1 | 6/1992 |
| EP | 0171496 B1 | 5/1993 |
| EP | 0125023 B2 | 3/2002 |
| WO | WO 86/01533 A1 | 3/1986 |
| WO | WO 88/01649 | 3/1988 |
| WO | WO 02/43478 A2 | 6/2002 |
| WO | WO 2011/155607 A1 | 8/2013 |
| WO | WO 2015/117002 A1 | 8/2015 |
| WO | WO 2016/068803 A1 | 5/2016 |
| WO | WO 2016/071448 A1 | 5/2016 |
| WO | WO 2017/079115 A1 | 5/2017 |

(Continued)

OTHER PUBLICATIONS

Lee et al., "TIM Polymorphisms—Genetics and Function," Genes Immunity, vol. 12, No. 8, pp. 595-604 (Dec. 2011).
Rodriguez-Manzanet et al., "The costimulatory role of TIM molecules," Immunol Rev, vol. 229, No. 1, pp. 259-270 (2009).
Anderson et al., "Promotion of Tissue Inflammation by the Immune Receptor Tim-3 Expressed on innate Immune Cells," Science Magazine, vol. 318 No. 5853, pp. 1141-1143 (Nov. 16, 2007).
Anderson, David, "TIM-3 as a therapeutic target in human infl ammatory diseases," Expert Opin Ther Targets, vol. 11, No. 8, pp. 1005-1009 (2007).
Anderson et al., "TIM-3 in autoimmunity," Current Opinion in Immunology, vol. 18, No. 6, pp. 665-669 (2006).
Degauque et al., "Regulation of T-Cell Immunity by T-Cell Immunoglobulin and Mucin Domain Proteins," Transplantation, vol. 84, pp. S12-16 , (2007).

(Continued)

*Primary Examiner* — Daniel C Gamett
(74) *Attorney, Agent, or Firm* — KDW Firm PLLC

(57) ABSTRACT

Provided by the present invention are an antibody against human TIM-3 or an antigen-binding fragment thereof, and further provided are a nucleic acid molecule encoding the antibody, an expression vector for expressing the antibody and a host cell, and a method for producing the antibody. Further provided by the present invention are a pharmaceutical composition comprising the antibody or an antigen-binding fragment of the antibody, and an application of the pharmaceutical composition in the preparation of a medicine, the medicine is used for preventing and/or treating various diseases (including tumors, infectious diseases and autoimmune diseases).

20 Claims, 10 Drawing Sheets
Specification includes a Sequence Listing.

(56) References Cited

FOREIGN PATENT DOCUMENTS

| WO | WO 2017/178493 A1 | 10/2017 |
| WO | WO 2019/206095 A1 | 10/2019 |

OTHER PUBLICATIONS

Zhu et al., "The Tim-3 ligand galectin-9 negatively regulates T helper type 1 immunity," Nature Immunology, vol. 6, No. 12, pp. 1245-1252 (2005).
Gorman et al., "Tim-3 directly enhances CD8 T cell responses to acute Listeria monocytogenes infection," J Immunol, vol. 192, No. 7, pp. 3133-3142 (2014).
Jost et al., "Dysregulated Tim-3 expression on natural killer cells is associated with increased Galectin-9 levels in HIV-1 infection," Retrovirology, vol. 10, No. 74 (2013).
Wang et al., "Elevated expression of Tim-3 on CD8 T cells correlates with disease severity of pulmonary tuberculosis," Journal of Infection, vol. 62, No. 4, pp. 292-300 (2011).
Jayaraman et al., "Tim3 binding to galectin-9 stimulates antimicrobial immunity," Journal of Experimental Medicine, vol. 207, No. 11, 2343-2354 (2010).
Ma et al., "Enhanced Virus-Specific CD8+ T Cell Responses by Listeria monocytogenes-Infected Dendritic Cells in the Context of Tim-3 Blockade," PLoS One, vol. 9, Issue. 1, pp. e87821 (2014).
Nebbia et al., "Upregulation of the Tim-3/Galectin-9 Pathway of T Cell Exhaustion in Chronic Hepatitis B Virus Infection," PLoS One vol. 7, Issue. 10, pp. e47648 (2012).
Komohara et al., "The Coordinated Actions of TIM-3 on Cancer and Myeloid Cells in the Regulation of Tumorigenicity and Clinical Prognosis in Clear Cell Renal Cell Carcinomas," Cancer Immunology Research, vol. 3, No. 9, pp. 999-1007 (2015).
Yan et al., "Tim-3 fosters HCC development by enhancing TGF-β-mediated alternative activation of Macrophages," Gut, vol. 64, vol. 10, pp. 1593-1604 (Jan. 21, 2015).
Fourcade et al., "Upregulation of Tim-3 and PD-1 expression is associated with tumor antigen—specific CD8+ T cell dysfunction in melanoma patients," Journal of Experimental Medicine, vol. 207, No. 10, pp. 2175-2186 (2010).
Edelman et al, "The Covalent Structure of an Entire TG Immunoglobulin Molecule" Proc. Natl. Acad. USA, vol. 63, pp. 78-85 (1969).
Sabatos et al., "Interaction of Tim-3 and Tim-3 ligand regulates T helper type 1 responses and induction of peripheral tolerance," Nature Immunology, vol. 4, No. 11, (2003).
Holliger et al., "Engineered antibody fragments and the rise of single domains," Nature Biotechnology, vol. 23, No. 9, pp. 1126-1136 (2005).
Chothia et al., "Structural Repertoire of the Human VH Segments," J. Mol. Biol, vol. 227, pp. 799-817 (1992).

Tomlinson et al., "The Repertoire of Human Germline VH Sequences Reveals about Fifty Groups of VH Segments with Different Hypervariable Loops" J. Mol. Biol, vol. 227, pp. 776-798 (1992).
Lefranc et al., "IMGT unique numbering for immunoglobulin and T cell receptor variable domains and Ig superfamily V-like domains," Developmental and Comparative Immunology, vol. 27, pp. 55-77 (2003).
MacCallum et al., "Antibody-antigen Interactions: Contact Analysis and Binding Site Topography," J. Mol. Biol., vol. 262, pp. 732-745 (1996).
Makabe et al., "Thermodynamic Consequences of Mutations in Vernier Zone Residues of a Humanized Anti-human Epidermal Growth Factor Receptor Murine Antibody, 528*☐," Journal of Biological Chemistry, vol. 283, No. 2, pp. 1156-1166 (2008).
Better et al., "*Escherichia coli* Secretion of an Acove Chimeric Antibody Fragment" Science, vol. 240, No. 4855, pp. 1041-1043 (1988).
Liu et al., "Chimeric mouse-human IgGi antibody that can mediate lysis of cancer cells," Proc. Natl. Acad. Sci. USA, vol. 84, pp. 3439-3443 (1987).
Sun et al., "Chimeric antibody with human constant regions and mouse variable regions directed against carcinoma-associated antigen 17-1A," Proc. Natl. Acad. Sci. USA, vol. 84, pp. 214-218 (1987).
Nishimura et al., "Recombinant Human-Mouse Chimeric Monoclonal Antibody Specific for Common Acute Lymphocytic Leukemia Antigen1," Cancer Research, vol. 47, pp. 999-1005 (1987).
Wood et al., "The synthesis and in Vivo assembly of functional antibodies in yeast," Nature, vol. 314, pp. 446-449 (1985).
Shaw et al., "Mouse/Human Chimeric Antibodies to a Tumor-Associated Antigen: Biologic Activity of the Four Human IgG Subclasses," J Natl Cancer Inst, vol. 80, No. 19, pp. 1553-1559 (1988).
Malmqvist, Magnus, "Biospecific interaction analysis using biosensor technology," Nature, vol. 361, pp. 186-187 (1993).
Davies et al., "Antibody—Antigen Complexes 1" Annual Rev Biochem, vol. 59, pp. 439-473 (1990).
Cao et al., "Tim-3 Expression in Cervical Cancer Promotes Tumor Metastasis," PLOS One, vol. 8, Issue. 1, pp. e53834 (2013).
Zhuang et al., "Ectopic Expression of TIM-3 in Lung Cancers, A Potential Independent Prognostic Factor for Patients With NSCLC," Am J Clin Pathol, vol. 137, No. 6, pp. 978-985 (2012).
Kikushige et al., "TIM-3 Is a Promising Target to Selectively Kill Acute Myeloid Leukemia Stem Cells," Cell Stem Cell, vol. 7, No. 6, pp. 708-717 (2010).
Kohler et al., "Continuous cultures of fused cells secreting antibody of predefined specificity," Nature, vol. 256, pp. 495-497 (1975).
Lonberg et al. "Antigen-specific human antibodies from mice comprising four distinct genetic modifications," Nature, vol. 368, No. 6474, pp. 856-859 (1994).
International Preliminary Report on Patentability and Written Opinion for Application No. PCT/CN2019/083727 dated Oct. 27, 2020.
International Search Report for Application No. PCT/CN2019/083727 dated Jul. 3, 2019.
European Search Report for Application No. 19791891 dated Dec. 21, 2021.

```
               FR-H1                    CDR-H1        FR-H2
Mab22-V_H  EVQLQLSGPELVKPGASVKMSCKAS  GYTFTNYV  MHWMRQKPGQGL
AB12S3-V_H ----VQ--A-VK----------V----  --------  --------A---R-
AB12S4-V_H ----V---A-V---------------  --------  -----------R-
AB12S5-V_H Q---VQ--A-VK----------V----  --------  ---V--A---R-
AB12S6-V_H Q-------A-VK----------V----  --------  ---V--A---R-
AB12S7-V_H --------A-VK----------V----  --------  -----------R-

CDR-H2          FR-H3
Mab22-V_H  EWIGY  IDPDNDGI  KYNEKIKGKATLTSDKSSSTAYMELSSLTSED
AB12S3-V_H -----  --------  -----------------------------R----
AB12S4-V_H -----  --------  -----------------------------R----
AB12S5-V_H --M-W  --------  --SQ-FQ-RV-I-R-T-A-----------R----
AB12S6-V_H --M-W  --------  --SQ-FQ-RV--------A----------R----
AB12S7-V_H --M-W  --------  --SQ-FQ-RV-I-R---------------R----

CDR-H3          FR-H4
Mab22-V_H  SAVYYC  ARDFGYVDWFPY  WGQGTLVTVSA
AB12S3-V_H T-----  ------------  ------T----S
AB12S4-V_H ------  ------------  ------T----S
AB12S5-V_H T-----  ------------  -------T---S
AB12S6-V_H T-----  ------------  -----------S
AB12S7-V_H T-----  ------------  -----------S
```

Figure 2

```
              FR-L1                          CDR-L1      FR-L2
Mab22-VL  DIVMTQSHKFMSTSVGNRVSITCKAS      QDVTTA      VAWYQQKSGQSPK
AB12S3-VL  ---------PSSL-A---D--T-----      ------      -------P-KA--
AB12S4-VL  ---------PSS------D--T-----      ------      -------P-K---
AB12S5-VL  --Q------PSSL-A---D--T--Q--      ------      LN-----P-KA--
AB12S6-VL  --Q------PSS--A---D--T--Q--      ------      LN-----P-K---
AB12S7-VL  ---------PSSL-A---D--T--Q--      ------      LN-----------

CDR-L2        FR-L3
Mab22-VL  LLIY  SAS   NRYIGVPDRFTGSGSGTDFTFTISSVQTEDLAVYYC    QQ
AB12S3-VL ----  ---   --------------------------L-P--I-T---    --
AB12S4-VL ----  ---   -----------------------------P--I-----   --
AB12S5-VL ----  ---   -LET---S--S---------------L-P--I-T---    --
AB12S6-VL ----  ---   -LET---S--S---------------L-P--I-T---    --
AB12S7-VL ----  ---   -LET---S--S---------------L-P--I-T---    --

CDR-L3     FR-L4
Mab22-VL  HYSIPPT   FGGGTNLEIK
AB12S3-VL -------   ------KV--
AB12S4-VL -------   ----------
AB12S5-VL -------   ------KV--
AB12S6-VL -------   ----------
AB12S7-VL -------   ----------
```

Figure 3

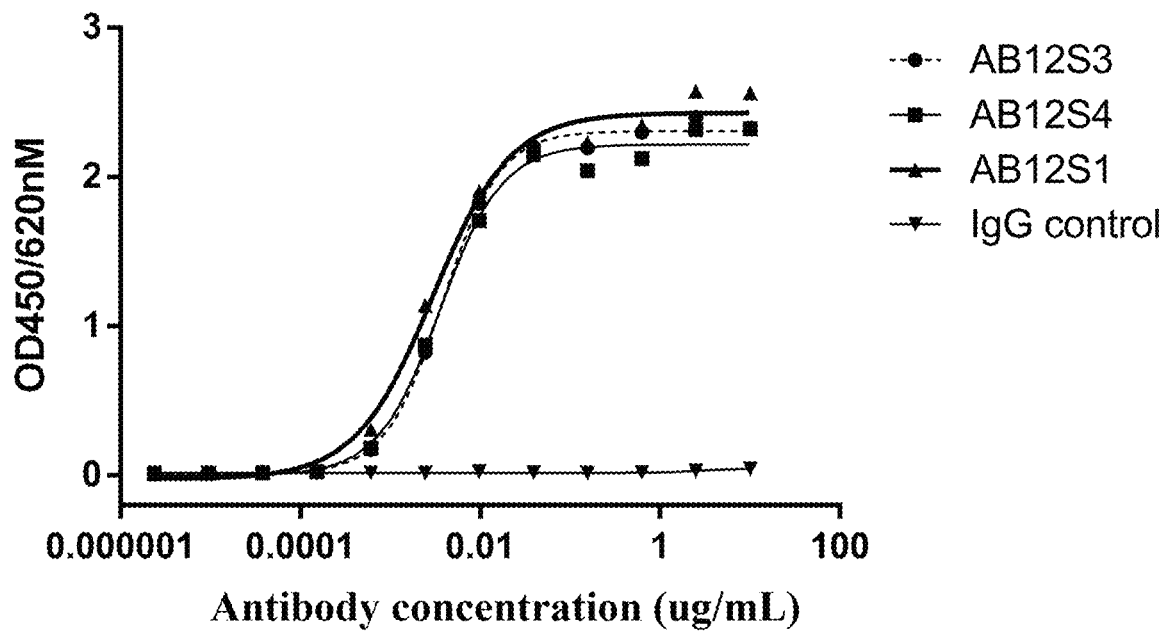

Figure 4

ANTIBODY AGAINST TIM-3 AND APPLICATION THEREOF

TECHNICAL FIELD

The present disclosure belongs to the field of therapeutic monoclonal antibodies. More specifically, the present disclosure relates to an antibody against human TIM-3 or an antigen-binding fragment thereof, and use of the antibody for anti-infection, anti-tumor and autoimmune diseases.

BACKGROUND

T-cell immunoglobulin and mucin domain 3 (TIM-3) is important immune checkpoint molecules that have been discovered in recent years. The TIM-3 molecule is a single transmembrane molecule, and the structure of the TIM-3 molecule includes an IgV subunit, a mucin-like domain, a single transmembrane domain, and a Tyr-rich intracellular segment (Lee J et al., Genes Immun, 2011, 12: 595-604). The IgV subunit is located on the outside of a cell and participates in ligand recognition together with the mucin-like domain.

TIM-3 is highly expressed on the surface of $CD4^+$ T helper 1 (Th1) cells and $CD8^+$ cytotoxic T (Tc1) cells that secrete IFN-γ (Rodriguez-Manzanet R et al., Immunol Rev, 2009, 229 (1): 259-270). Galectin-9 (Gal-9), as one of natural ligands of TIM-3, is a member of the endogenous galectin protein family and widely distributed in tissues, and plays an important role in cell aggregation, adhesion, differentiation and apoptosis, the regulation of tumor metastasis and inflammation. Gal-9 binds to TIM-3 on the surface of T cells to trigger an intracellular signaling pathway and induce the functional exhaustion or apoptosis of the T cells, thus relieving an immune response. Gal-9 plays an important regulatory role in autoimmune diseases, allergic diseases and rejections. Therefore, TIM-3 is considered to be a negative immunomodulatory molecule. A subsequent discovery is that TIM-3 is also expressed on the surface of natural immune cells, such as regulatory T cells (Treg), monocytes, macrophages, dendritic cells (DCs) and natural killer (NK) cells, (Andemon A C et al., Science, 2007, 318 (5853): 1141-1143). At present, studies prove that TIM-3/Gal-9 can regulate the immune response of a variety of cells, and is widely involved in the occurrence and development of inflammation, autoimmune diseases, and tumors (Anderson D E, Expert Opin Ther Targets, 2007, 11(8): 1005-1009; Anderson A C, Curr Opin Immunol, 2006, 18 (6): 665-669; Degauque N et al., Transplantation, 2007, 84: S12-16; Zhu C et al., Nat Immunol, 2005, 6: 1245-1252).

In recent years, studies have found that the high expression of TIM-3 on T cells is closely related to the functional exhaustion of the T cells during pathogen infection and that the expression of TIM-3 on macrophages is also up-regulated (Gorman J V et al., J Immunol, 2014, 192(7): 3133-3142; Jost S et al., Retrovirology, 2013, 10: 74), suggesting that TIM-3 also plays an important role in the process of infection and immunity. Wang et al. have found that after the TIM-3 pathway of peripheral blood mononuclear cells is blocked with mouse anti-human TIM-3 antibody in human patients infected with *M. tuberculosis*, the production of IFN-γ by T cells is significantly enhanced, so that the exhaustion of the T cells is improved, and the body's resistance to *M. tuberculosis* is enhanced (Wang X et al., J Infect, 2011, 62 (4): 292-300). Jayaraman et al. have found that after C57BL/6J mice were infected with *Mycobacterium tuberculosis* through the respiratory tract, the injection of TIM3-Ig fusion protein can enhance the elimination of *M. tuberculosis* in vivo (Jayaraman P et al., J Exp Med, 2010, 207 (11): 2343-2354). Ma et al. have found that DC cells of normal persons or HCV-infected persons, after being blocked by an antibody against TIM-3, can have enhanced antigen uptake, accelerated maturation and increased IL-12 secretion (Ma C J et al., PLoS One, 2014, 9 (1): e87821). Nebbia et al. have found that blocking the TIM-3 pathway with recombinant TIM3-Fc fusion protein can improve the functional exhaustion of HBV-specific $CD8^+$ T cells. The IFN-γ and TNF-α expression of HBV-specific $CD8^+$ T cells in peripheral blood mononuclear cells of some chronic HBV patients can be recovered by blocking the TIM-3 pathway in vitro (Nebbia G et al., PLoS One, 2012, 7 (10): e47648). The series of studies above prove that by blocking the TIM-3 signaling pathway through the antibody against TIM-3 (antagonist antibody) or fusion protein (composed of only extracellular fragments of TIM-3), the function of immune cells can be reversed in vivo and in vitro, thereby enhancing an anti-infection ability of human bodies. Therefore, TIM-3 is a potential intervention target for anti-infective immunotherapy.

The abnormal expression of TIM-3, as an important immunomodulatory target, on various immune cells is closely related to the occurrence and development of various tumors. It has been found at present that the expression of TIM-3 on the surface of $CD8^+$ T cells of a variety of malignant tumors, such as urinary system tumors, renal cell carcinoma, colon cancer, breast cancer and hematological tumors, is up-regulated. TIM-3 can regulate the functional exhaustion of T cells and suppress the immune response of the T cells. Inhibition of signals downstream of TIM-3 with blocking antibodies or fusion proteins can increase IFN-γ secreted by T cells. In in vitro experiments of renal clear cell carcinoma and liver cancer, the tumors are significantly inhibited after the TIM-3/Gal-9 pathway is suppressed by using monoclonal antibodies (Komohara Y et al., Cancer Immunol Res, 2015, 3 (9): 999-1007; Yan W et al., Gut, 2015, 64 (10): 1593-1604). The subcutaneous injection of anti-TIM-3 monoclonal antibodies can inhibit the growth of EIA lymphoma in mice (Fourcade J et al., Exp Med, 2010, 207(10): 2175-2186).

Therefore, a TIM-3 blocking antibody with high specificity and affinity, lower toxic side effects and better clinical efficacy is urgently needed in clinics, which will also provide more medicament choices for patients with tumors, infectious diseases or autoimmune diseases.

SUMMARY

The present disclosure discloses an antibody or an antigen-binding fragment thereof that binds to TIM-3 with high affinity and specificity. The present disclosure further provides a nucleic acid molecule for encoding the antibody molecule, an expression vector, a host cell, and a method for producing the antibody molecule. The present disclosure further provides a bispecific antibody, a multi-bispecific antibody and a pharmaceutical composition containing the antibody molecule. In addition, the present disclosure further provides use of an anti-TIM-3 antibody or an antigen-binding fragment thereof (alone or in combination with other active agents or treatment methods) for preparing a medicament for treating, preventing and/or diagnosing cancer, infectious diseases, Crohn's disease, sepsis, systemic inflammatory response syndrome (SIRS), glomerulonephritis or other diseases.

In a first aspect, the present disclosure provides an antibody or an antigen-binding fragment thereof capable of specifically binding to TIM-3, wherein the antibody or the antigen-binding fragment thereof includes complementarity determining regions (CDRs) selected from following groups:
(a) following three CDRs of a heavy chain variable region (VH):
  (i) CDR-H1, which has a sequence of CDR-H1 contained in a VH as shown by SEQ ID NO: 1, or has a sequence with one or more amino acid substitutions, deletions or additions (such as 1, 2 or 3 substitutions, deletions or additions) relative to the sequence of CDR-H1 contained in the VH;
  (ii) CDR-H2, which has a sequence of CDR-H2 contained in the VH as shown by SEQ ID NO: 1, or has a sequence with one or more amino acid substitutions, deletions or additions (such as 1, 2 or 3 substitutions, deletions or additions) relative to the sequence of CDR-H2 contained in the VH; and
  (iii) CDR-H3, which has a sequence of CDR-H3 contained in the VH as shown by SEQ ID NO: 1, or has a sequence with one or more amino acid substitutions, deletions or additions (such as 1, 2 or 3 substitutions, deletions or additions) relative to the sequence of CDR-H3 contained in the VH; and/or
following three CDRs of a light chain variable region (VL):
  (iv) CDR-L1, which has a sequence of CDR-L1 contained in a VL as shown by SEQ ID NO: 2, or has a sequence with one or more amino acid substitutions, deletions or additions (such as 1, 2 or 3 substitutions, deletions or additions) relative to the sequence of CDR-L1 contained in the VL;
  (v) CDR-L2, which has a sequence of CDR-L2 contained in the VL as shown by SEQ ID NO: 2, or has a sequence with one or more amino acid substitutions, deletions or additions (such as 1, 2 or 3 substitutions, deletions or additions) relative to the sequence of CDR-L2 contained in the VL; and
  (vi) CDR-L3, which has a sequence of CDR-L3 contained in the VL as shown by SEQ ID NO: 2, or has a sequence with one or more amino acid substitutions, deletions or additions (such as 1, 2 or 3 substitutions, deletions or additions) relative to the sequence of CDR-L3 contained in the VL; or
(b) following three CDRs of a heavy chain variable region (VH):
  (i) CDR-H1, which has a sequence of CDR-H1 contained in a VH as shown by SEQ ID NO: 7, or has a sequence with one or more amino acid substitutions, deletions or additions (such as 1, 2 or 3 substitutions, deletions or additions) relative to the sequence of CDR-H1 contained in the VH;
  (ii) CDR-H2, which has a sequence of CDR-H2 contained in the VH as shown by SEQ ID NO: 7, or has a sequence with one or more amino acid substitutions, deletions or additions (such as 1, 2 or 3 substitutions, deletions or additions) relative to the sequence of CDR-H2 contained in the VH; and
  (iii) CDR-H3, which has a sequence of CDR-H3 contained in the VH as shown by SEQ ID NO: 7, or has a sequence with one or more amino acid substitutions, deletions or additions (such as 1, 2 or 3 substitutions, deletions or additions) relative to the sequence of CDR-H3 contained in the VH; and/or following three CDRs of a light chain variable region (VL):
  (iv) CDR-L1, which has a sequence of CDR-L1 contained in a VL as shown by SEQ ID NO: 8, or has a sequence with one or more amino acid substitutions, deletions or additions (such as 1, 2 or 3 substitutions, deletions or additions) relative to the sequence of CDR-L1 contained in the VL;
  (v) CDR-L2, which has a sequence of CDR-L2 contained in the VL as shown by SEQ ID NO: 8, or has a sequence with one or more amino acid substitutions, deletions or additions (such as 1, 2 or 3 substitutions, deletions or additions) relative to the sequence of CDR-L2 contained in the VL; and
  (vi) CDR-L3, which has a sequence of CDR-L3 contained in the VL as shown by SEQ ID NO: 8, or has a sequence with one or more amino acid substitutions, deletions or additions (such as 1, 2 or 3 substitutions, deletions or additions) relative to the sequence of CDR-L3 contained in the VL.

In some preferred embodiments, the substitutions in any one of (i) to (vi) are conservative substitutions.

In some preferred embodiments, CDR-H1, CDR-H2 and CDR-H3 contained in the heavy chain variable region (VH), and/or CDR-L1, CDR-L2 and CDR-L3 contained in the light chain variable region (VL) are defined by a Kabat, Chothia or IMGT numbering system.

In some preferred embodiments, the antibody or the antigen-binding fragment thereof in the present disclosure includes:
  (a) three CDRs contained in a heavy chain variable region (VH) selected from:
    a VH as shown by any one of SEQ ID NO: 1, SEQ ID NO: 3, SEQ ID NO: 5, SEQ ID NO: 7, SEQ ID NO: 9 and SEQ ID NO: 11, and/or
  (b) three CDRs contained in a light chain variable region (VL) selected from:
    a VL as shown by any one of SEQ ID NO: 2, SEQ ID NO: 4, SEQ ID NO: 6, SEQ ID NO: 8, SEQ ID NO: 10 and SEQ ID NO: 12.

In some preferred embodiments, the three CDRs contained in the heavy chain variable region (VH), and/or the three CDRs contained in the light chain variable region (VL) are defined by the Kabat, Chothia or IMGT numbering system.

In some preferred embodiments, the antibody or the antigen-binding fragment thereof in the present disclosure includes: (1) three CDRs contained in the heavy chain variable region (VH) as shown by SEQ ID NO: 1, and/or three CDRs contained in the light chain variable region (VL) as shown by SEQ ID NO: 2, where the three CDRs contained in the heavy chain variable region (VH) and the three CDRs contained in the light chain variable region (VL) are defined by the IMGT numbering system.

In some preferred embodiments, the antibody or the antigen-binding fragment thereof includes:
  (a) following three heavy chain variable region (VH) CDRs:
    (i) CDR-H1, consisting of a sequence as shown by SEQ ID NO: 18, or a sequence with one or more amino acid substitutions, deletions or additions (such as 1, 2 or 3 substitutions, deletions or additions) relative to the sequence as shown by SEQ ID NO: 18;
    (ii) CDR-H2, consisting of a sequence as shown by SEQ ID NO: 19, or a sequence with one or more amino acid substitutions, deletions or additions (such as 1, 2 or 3 substitutions, deletions or additions) relative to the sequence as shown by SEQ ID NO: 19; and (iii) CDR-H3, consisting of a sequence as shown by SEQ ID NO: 20, or a sequence with one or more amino acid substitutions, deletions or additions (such as 1, 2 or 3 substitutions, deletions or additions) relative to the sequence as shown by SEQ ID NO: 20; and/or (b) following three light chain variable region (VL) CDRs:

(iv) CDR-L1, consisting of a sequence as shown by SEQ ID NO: 27, or a sequence with one or more amino acid substitutions, deletions or additions (such as 1, 2 or 3 substitutions, deletions or additions) relative to the sequence as shown by SEQ ID NO: 27;

(v) CDR-L2, consisting of a sequence as shown by SEQ ID NO: 25, or a sequence with one or more amino acid substitutions, deletions or additions (such as 1, 2 or 3 substitutions, deletions or additions) relative to the sequence as shown by SEQ ID NO: 25; and (vi) CDR-L3, consisting of a sequence as shown by SEQ ID NO: 23, or a sequence with one or more amino acid substitutions, deletions or additions (such as 1, 2 or 3 substitutions, deletions or additions) relative to the sequence as shown by SEQ ID NO: 23;

where the heavy chain variable region (VH) CDRs and the light chain variable region (VL) CDRs are defined by the IMGT numbering system.

In some preferred embodiments, the substitutions in any one of (i) to (vi) are conservative substitutions.

In some preferred embodiments, a VH of the antibody or the antigen-binding fragment thereof in the present disclosure includes: CDR-H1 as shown by SEQ ID NO: 18, CDR-H2 as shown by SEQ ID NO: 19 and CDR-H3 as shown by SEQ ID NO: 20; and a VL of the antibody or the antigen-binding fragment thereof includes: CDR-L1 as shown by SEQ ID NO: 27, CDR-L2 as shown by SEQ ID NO: 25 and CDR-L3 as shown by SEQ ID NO: 23.

In some preferred embodiments, the antibody or the antigen-binding fragment thereof in the present disclosure includes:

(a) three CDRs contained in the heavy chain variable region (VH) as shown by SEQ ID NO: 1, and/or three CDRs contained in the light chain variable region (VL) as shown by SEQ ID NO: 2;

where the three CDRs contained in the heavy chain variable region (VH) and the three CDRs contained in the light chain variable region (VL) are defined by the Chothia numbering system.

In some preferred embodiments, the antibody or the antigen-binding fragment thereof includes:

(a) following three heavy chain variable region (VH) CDRs:

(i) CDR-H1, consisting of a sequence as shown by SEQ ID NO: 16, or a sequence with one or more amino acid substitutions, deletions or additions (such as 1, 2 or 3 substitutions, deletions or additions) relative to the sequence as shown by SEQ ID NO: 16;

(ii) CDR-H2, consisting of a sequence as shown by SEQ ID NO: 17, or a sequence with one or more amino acid substitutions, deletions or additions (such as 1, 2 or 3 substitutions, deletions or additions) relative to the sequence as shown by SEQ ID NO: 17; and (iii) CDR-H3, consisting of a sequence as shown by SEQ ID NO: 15, or a sequence with one or more amino acid substitutions, deletions or additions (such as 1, 2 or 3 substitutions, deletions or additions) relative to the sequence as shown by SEQ ID NO: 15; and/or (b) following three light chain variable region (VL) CDRs:

(iv) CDR-L1, consisting of a sequence as shown by SEQ ID NO: 24, or a sequence with one or more amino acid substitutions, deletions or additions (such as 1, 2 or 3 substitutions, deletions or additions) relative to the sequence as shown by SEQ ID NO: 24;

(v) CDR-L2, consisting of a sequence as shown by SEQ ID NO: 25, or a sequence with one or more amino acid substitutions, deletions or additions (such as 1, 2 or 3 substitutions, deletions or additions) relative to the sequence as shown by SEQ ID NO: 25; and (vi) CDR-L3, consisting of a sequence as shown by SEQ ID NO: 26, or a sequence with one or more amino acid substitutions, deletions or additions (such as 1, 2 or 3 substitutions, deletions or additions) relative to the sequence as shown by SEQ ID NO: 26;

where the heavy chain variable region (VH) CDRs and the light chain variable region (VL) CDRs are defined by the Chothia numbering system.

In some preferred embodiments, the substitutions in any one of (i) to (vi) are conservative substitutions.

In some preferred embodiments, a VH of the antibody or the antigen-binding fragment thereof in the present disclosure includes: CDR-H1 as shown by SEQ ID NO: 16, CDR-H2 as shown by SEQ ID NO: 17 and CDR-H3 as shown by SEQ ID NO: 15; and a VL of the antibody or the antigen-binding fragment thereof includes: CDR-L1 as shown by SEQ ID NO: 24, CDR-L2 as shown by SEQ ID NO: 25 and CDR-L3 as shown by SEQ ID NO: 26.

In some preferred embodiments, the antibody or the antigen-binding fragment thereof in the present disclosure includes:

(a) three CDRs contained in the heavy chain variable region (VH) as shown by SEQ ID NO: 1, and/or three CDRs contained in the light chain variable region (VL) as shown by SEQ ID NO: 2; or (b) three CDRs contained in the heavy chain variable region (VH) as shown by SEQ ID NO: 7, and/or three CDRs contained in the light chain variable region (VL) as shown by SEQ ID NO: 8;

where the three CDRs contained in the heavy chain variable region (VH) and the three CDRs contained in the light chain variable region (VL) are defined by the Kabat numbering system.

In some preferred embodiments, the antibody or the antigen-binding fragment thereof includes:

(a) following three heavy chain variable region (VH) CDRs:

(i) CDR-H1, consisting of a sequence as shown by SEQ ID NO: 13, or a sequence with one or more amino acid substitutions, deletions or additions (such as 1, 2 or 3 substitutions, deletions or additions) relative to the sequence as shown by SEQ ID NO: 13;

(ii) CDR-H2, consisting of a sequence as shown by SEQ ID NO: 14, or a sequence with one or more amino acid substitutions, deletions or additions (such as 1, 2 or 3 substitutions, deletions or additions) relative to the sequence as shown by SEQ ID NO: 14; and (iii) CDR-H3, consisting of a sequence as shown by SEQ ID NO: 15, or a sequence with one or more amino acid substitutions, deletions or additions (such as 1, 2 or 3 substitutions, deletions or additions) relative to the sequence as shown by SEQ ID NO: 15; and/or (b) following three light chain variable region (VL) CDRs:

(iv) CDR-L1, consisting of a sequence as shown by SEQ ID NO: 21, or a sequence with one or more amino acid substitutions, deletions or additions (such as 1, 2 or 3 substitutions, deletions or additions) relative to the sequence as shown by SEQ ID NO: 21;

(v) CDR-L2, consisting of a sequence as shown by SEQ ID NO: 22, or a sequence with one or more amino acid substitutions, deletions or additions (such as 1, 2 or 3 substitutions, deletions or additions) relative to the sequence as shown by SEQ ID NO: 22; and (vi) CDR-L3, consisting of a sequence as shown by SEQ ID NO: 23, or a sequence with one or more amino acid substitutions, deletions or additions (such as 1, 2 or 3 substitutions, deletions or additions) relative to the sequence as shown by SEQ ID NO: 23; where the heavy chain variable region (VH) CDRs and the light chain variable region (VL) CDRs are defined by the Kabat numbering system.

In some preferred embodiments, the substitutions in any one of (i) to (vi) are conservative substitutions.

In some preferred embodiments, a VH of the antibody or the antigen-binding fragment thereof in the present disclosure includes: CDR-H1 as shown by SEQ ID NO: 13, CDR-H2 as shown by SEQ ID NO: 14 and CDR-H3 as shown by SEQ ID NO: 15; and a VL of the antibody or the antigen-binding fragment thereof includes: CDR-L1 as shown by SEQ ID NO: 21, CDR-L2 as shown by SEQ ID NO: 22 and CDR-L3 as shown by SEQ ID NO: 23.

In some preferred embodiments, the antibody or the antigen-binding fragment thereof includes:

(a) following three heavy chain variable region (VH) CDRs:

(i) CDR-H1, consisting of a sequence as shown by SEQ ID NO: 13, or a sequence with one or more amino acid substitutions, deletions or additions (such as 1, 2 or 3 substitutions, deletions or additions) relative to the sequence as shown by SEQ ID NO: 13;

(ii) CDR-H2, consisting of a sequence as shown by SEQ ID NO: 28, or a sequence with one or more amino acid substitutions, deletions or additions (such as 1, 2 or 3 substitutions, deletions or additions) relative to the sequence as shown by SEQ ID NO: 28; and (iii) CDR-H3, consisting of a sequence as shown by SEQ ID NO: 15, or a sequence with one or more amino acid substitutions, deletions or additions (such as 1, 2 or 3 substitutions, deletions or additions) relative to the sequence as shown by SEQ ID NO: 15; and/or (b) following three light chain variable region (VL) CDRs:

(iv) CDR-L1, consisting of a sequence as shown by SEQ ID NO: 29, or a sequence with one or more amino acid substitutions, deletions or additions (such as 1, 2 or 3 substitutions, deletions or additions) relative to the sequence as shown by SEQ ID NO: 29;

(v) CDR-L2, consisting of a sequence as shown by SEQ ID NO: 30, or a sequence with one or more amino acid substitutions, deletions or additions (such as 1, 2 or 3 substitutions, deletions or additions) relative to the sequence as shown by SEQ ID NO: 30; and (vi) CDR-L3, consisting of a sequence as shown by SEQ ID NO: 23, or a sequence with one or more amino acid substitutions, deletions or additions (such as 1, 2 or 3 substitutions, deletions or additions) relative to the sequence as shown by SEQ ID NO: 23;

where the heavy chain variable region (VH) CDRs and the light chain variable region (VL) CDRs are defined by the Kabat numbering system.

In some preferred embodiments, the substitutions in any one of (i) to (vi) are conservative substitutions.

In some preferred embodiments, a VH of the antibody or the antigen-binding fragment thereof in the present disclosure includes: CDR-H1 as shown by SEQ ID NO: 13, CDR-H2 as shown by SEQ ID NO: 28 and CDR-H3 as shown by SEQ ID NO: 15; and a VL of the antibody or the antigen-binding fragment thereof includes: CDR-L1 as shown by SEQ ID NO: 29, CDR-L2 as shown by SEQ ID NO: 30 and CDR-L3 as shown by SEQ ID NO: 23.

In some preferred embodiments, the antibody or the antigen-binding fragment thereof in the present disclosure further includes a framework region (FR) derived from a mammalian (e.g., a murine or a human) immunoglobulin.

In some preferred embodiments, a VH of the antibody or the antigen-binding fragment thereof in the present disclosure includes a framework region (FR) derived from a heavy chain variable region (VH) of a murine immunoglobulin, and/or a VL of the antibody or the antigen-binding fragment thereof includes a framework region (FR) derived from a light chain variable region (VL) of a murine immunoglobulin.

In some preferred embodiments, a VH of the antibody or the antigen-binding fragment thereof in the present disclosure includes a framework region (FR) derived from a heavy chain variable region (VH) of a human immunoglobulin, and/or a VL of the antibody or the antigen-binding fragment thereof includes a framework region (FR) derived from a light chain variable region (VL) of a human immunoglobulin. In such embodiments, the FR in the heavy chain variable region and/or the FR in the light chain variable region of the antibody or the antigen-binding fragment thereof in the present disclosure may include one or more non-human (e.g., murine) amino acid residues, for example, the heavy chain framework region (FR) and/or the light chain framework region (FR) may include one or more amino acid back mutations which include corresponding murine amino acid residues.

In some preferred embodiments, the antibody or the antigen-binding fragment thereof in the present disclosure includes:

(a) a heavy chain framework region of a human immunoglobulin or a variant thereof, where the variant has at most 20 conservative amino acid substitutions (for example, at most 15 conservative substitutions, at most 10 conservative substitutions or at most 5 conservative substitutions, such as 1, 2, 3, 4 or 5 conservative substitutions) relative to a sequence from which the variant is derived; and/or
(b) a light chain framework region of a human immunoglobulin or a variant thereof, where the variant has at most 20 conservative amino acid substitutions (for example, at most 15 conservative substitutions, at most 10 conservative substitutions or at most 5 conservative substitutions, such as 1, 2, 3, 4 or 5 conservative substitutions) relative to a sequence from which the variant is derived.

Therefore, in some preferred embodiments, the antibody or the antigen-binding fragment thereof in the present disclosure is humanized. In some preferred embodiments, a degree of humanization of the antibody or the antigen-binding fragment thereof in the present disclosure is at least 75%, at least 80%, at least 85%, at least 90%, at least 91%, at least 92%, at least 93%, at least 94%, at least 95%, at least 96%, at least 97%, at least 98%, at least 99% or 100%.

In some preferred embodiments, the antibody or the antigen-binding fragment thereof in the present disclosure includes:
(a) a heavy chain variable region (VH), including an amino acid sequence selected from:
  (i) a sequence as shown by any one of SEQ ID NOs: 1, 3, 5, 7, 9 and 11;
  (ii) a sequence with one or more amino acid substitutions, deletions or additions (such as 1, 2, 3, 4 or 5 substitutions, deletions or additions) relative to the sequence as shown by any one of SEQ ID NOs: 1, 3, 5, 7, 9 and 11; or
  (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by any one of SEQ ID NOs: 1, 3, 5, 7, 9 and 11; and/or
(b) a light chain variable region (VL), including an amino acid sequence selected from:
  (iv) a sequence as shown by any one of SEQ ID NOs: 2, 4, 6, 8, 10 and 12;
  (v) a sequence with one or more amino acid substitutions, deletions or additions (such as 1, 2, 3, 4 or 5 substitutions, deletions or additions) relative to the sequence as shown by any one of SEQ ID NOs: 2, 4, 6, 8, 10 and 12; or
  (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by any one of SEQ ID NOs: 2, 4, 6, 8, 10 and 12.

In some preferred embodiments, the substitutions in (ii) or (v) are conservative substitutions.

In some preferred embodiments, the antibody or the antigen-binding fragment thereof in the present disclosure includes:
(a) a heavy chain variable region (VH), including an amino acid sequence selected from:
  (i) a sequence as shown by SEQ ID NO: 1;
  (ii) a sequence with one or more substitutions, deletions or additions (such as 1, 2, 3, 4 or 5 substitutions, deletions or additions) relative to the sequence as shown by SEQ ID NO: 1; or
  (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 1; and
(b) a light chain variable region (VL), including an amino acid sequence selected from:
  (iv) a sequence as shown by SEQ ID NO: 2;
  (v) a sequence with one or more amino acid substitutions, deletions or additions (such as 1, 2, 3, 4 or 5 substitutions, deletions or additions) relative to the sequence as shown by SEQ ID NO: 2; or
  (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 2.

In some preferred embodiments, the substitutions in (ii) or (v) are conservative substitutions.

In some preferred embodiments, the antibody or the antigen-binding fragment thereof in the present disclosure includes:
(a) a heavy chain variable region (VH), including an amino acid sequence selected from:
  (i) a sequence as shown by SEQ ID NO: 3;
  (ii) a sequence with one or more amino acid substitutions, deletions or additions (such as 1, 2, 3, 4 or 5 substitutions, deletions or additions) relative to the sequence as shown by SEQ ID NO: 3; or
  (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 3; and
(b) a light chain variable region (VL), including an amino acid sequence selected from:
  (iv) a sequence as shown by SEQ ID NO: 4;
  (v) a sequence with one or more amino acid substitutions, deletions or additions (such as 1, 2, 3, 4 or 5 substitutions, deletions or additions) relative to the sequence as shown by SEQ ID NO: 4; or
  (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 4.

In some preferred embodiments, the substitutions in (ii) or (v) are conservative substitutions.

In some preferred embodiments, the antibody or the antigen-binding fragment thereof in the present disclosure includes:
(a) a heavy chain variable region (VH), including an amino acid sequence selected from:
  (i) a sequence as shown by SEQ ID NO: 5;
  (ii) a sequence with one or more amino acid substitutions, deletions or additions (such as 1, 2, 3, 4 or 5 substitutions, deletions or additions) relative to the sequence as shown by SEQ ID NO: 5; or
  (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 5; and
(b) a light chain variable region (VL), including an amino acid sequence selected from:
  (iv) a sequence as shown by SEQ ID NO: 6;
  (v) a sequence with one or more amino acid substitutions, deletions or additions (such as 1, 2, 3, 4 or 5 substitutions, deletions or additions) relative to the sequence as shown by SEQ ID NO: 6; or (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 6.

In some preferred embodiments, the substitutions in (ii) or (v) are conservative substitutions.

In some preferred embodiments, the antibody or the antigen-binding fragment thereof in the present disclosure includes:
(a) a heavy chain variable region (VH), including an amino acid sequence selected from:
 (i) a sequence as shown by SEQ ID NO: 7;
 (ii) a sequence with one or more amino acid substitutions, deletions or additions (such as 1, 2, 3, 4 or 5 substitutions, deletions or additions) relative to the sequence as shown by SEQ ID NO: 7; or
 (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 7; and
(b) a light chain variable region (VL), including an amino acid sequence selected from:
 (iv) a sequence as shown by SEQ ID NO: 8;
 (v) a sequence with one or more amino acid substitutions, deletions or additions (such as 1, 2, 3, 4 or 5 substitutions, deletions or additions) relative to the sequence as shown by SEQ ID NO: 8; or
 (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 8.

In some preferred embodiments, the substitutions in (ii) or (v) are conservative substitutions.

In some preferred embodiments, the antibody or the antigen-binding fragment thereof in the present disclosure includes:
(a) a heavy chain variable region (VH), including an amino acid sequence selected from:
 (i) a sequence as shown by SEQ ID NO: 9;
 (ii) a sequence with one or more amino acid substitutions, deletions or additions (such as 1, 2, 3, 4 or 5 substitutions, deletions or additions) relative to the sequence as shown by SEQ ID NO: 9; or
 (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 9; and
(b) a light chain variable region (VL), including an amino acid sequence selected from:
 (iv) a sequence as shown by SEQ ID NO: 10;
 (v) a sequence with one or more amino acid substitutions, deletions or additions (such as 1, 2, 3, 4 or 5 substitutions, deletions or additions) relative to the sequence as shown by SEQ ID NO: 10; or
 (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 10.

In some preferred embodiments, the substitutions in (ii) or (v) are conservative substitutions.

In some preferred embodiments, the antibody or the antigen-binding fragment thereof in the present disclosure includes:
(a) a heavy chain variable region (VH), including an amino acid sequence selected from:
 (i) a sequence as shown by SEQ ID NO: 11;
 (ii) a sequence with one or more amino acid substitutions, deletions or additions (such as 1, 2, 3, 4 or 5 substitutions, deletions or additions) relative to the sequence as shown by SEQ ID NO: 11; or
 (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 11; and
(b) a light chain variable region (VL), including an amino acid sequence selected from:
 (iv) a sequence as shown by SEQ ID NO: 12;
 (v) a sequence with one or more amino acid substitutions, deletions or additions (such as 1, 2, 3, 4 or 5 substitutions, deletions or additions) relative to the sequence as shown by SEQ ID NO: 12; or
 (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 12.

In some preferred embodiments, the substitutions in (ii) or (v) are conservative substitutions.

In some preferred embodiments, the antibody or the antigen-binding fragment thereof in the present disclosure includes:
(1) a VH having a sequence as shown by SEQ ID NO: 1 and a VL having a sequence as shown by SEQ ID NO: 2;
(2) a VH having a sequence as shown by SEQ ID NO: 3 and a VL having a sequence as shown by SEQ ID NO: 4;
(3) a VH having a sequence as shown by SEQ ID NO: 5 and a VL having a sequence as shown by SEQ ID NO: 6;
(4) a VH having a sequence as shown by SEQ ID NO: 7 and a VL having a sequence as shown by SEQ ID NO: 8;
(5) a VH having a sequence as shown by SEQ ID NO: 9 and a VL having a sequence as shown by SEQ ID NO: 10; or
(6) a VH having a sequence as shown by SEQ ID NO: 11 and a VL having a sequence as shown by SEQ ID NO: 12.

In some preferred embodiments, the antibody or the antigen-binding fragment thereof in the present disclosure further includes a constant region sequence derived from a mammalian (e.g., a murine or a human) immunoglobulin or a variant thereof, where the variant has one or more substitutions, deletions or additions relative to a sequence from which the variant is derived. In some preferred embodiments, the variant has one or more conservative substitutions relative to the sequence from which the variant is derived. In some embodiments, an anti-TIM-3 antibody molecule has a heavy chain constant region (Fc) selected from, for example, heavy chain constant regions of IgG1, IgG2, IgG3, IgG4, IgM, IgA1, IgA2, IgD and IgE, particularly selected from, for example, heavy chain constant regions of IgG1, IgG2, IgG3 and IgG4, and more particularly selected from a heavy chain constant region of IgG1 or IgG4 (such as human IgG1 or IgG4). In some embodiments, the anti-TIM-3 antibody molecule has a light chain constant region selected from, for example, κ or Δ light chain constant regions, preferably a κ light chain constant region (such as a human κ light chain).

In some preferred embodiments, a heavy chain of the antibody or the antigen-binding fragment thereof in the present disclosure includes: a heavy chain constant region (CH) of a human immunoglobulin or a variant thereof, where the variant has one or more substitutions, deletions or additions (for example, at most 20, at most 15, at most 10 or at most 5 substitutions, deletions or additions, such as 1, 2, 3, 4 or 5 substitutions, deletions or additions) relative to a sequence from which the variant is derived; and/or
- a light chain of the antibody or the antigen-binding fragment thereof in the present disclosure includes a light chain constant region (CL) of a human immunoglobulin or a variant thereof, where the variant has at most 20 conservative substitutions (for example, at most 15, at most 10 or at most 5 conservative substitutions, such as 1, 2, 3, 4 or 5 conservative substitutions) relative to a sequence from which the variant is derived.

In some embodiments, a heavy chain of the antibody or the antigen-binding fragment thereof in the present disclosure includes: a heavy chain constant region (CH) of a murine immunoglobulin or a variant thereof, where the variant has at most 20 conservative amino acid substitutions (for example, at most 15, at most 10 or at most 5 conservative substitutions, such as 1, 2, 3, 4 or 5 conservative substitutions) relative to a sequence from which the variant is derived; and/or
- a light chain of the antibody or the antigen-binding fragment thereof in the present disclosure includes a light chain constant region (CL) of a murine immunoglobulin or a variant thereof, where the variant has at most 20 conservative amino acid substitutions (for example, at most 15, at most 10 or at most 5 conservative substitutions, such as 1, 2, 3, 4 or 5 conservative substitutions) relative to a sequence from which the variant is derived.

In some embodiments, the constant region is changed, for example, mutated to modify properties of the anti-TIM-3 antibody molecule (e.g., to change one or more of the following properties: Fc receptor binding, antibody glycosylation, the number of cysteine residues, a function of an effector cell or a function of a complement). At least one amino acid residue in the constant region of the antibody may be replaced with different residues for a functional change, for example, changing the affinity of the antibody to an effector ligand (such as FcR or complement C1q), thereby changing (such as enhancing, decreasing or eliminating) an effector function. A method for replacing amino acid residues in the Fc region of the antibody to change the effector function is known in the art (referring to, for example, EP388151A1, U.S. Pat. Nos. 5,648,260 and 5,624,821). The Fc region of the antibody mediates several important effector functions, such as ADCC, phagocytosis and CDC. In some cases, these effector functions are necessary for therapeutic antibodies; but in other cases, these effector functions may be unnecessary or even harmful, which depends on an intended purpose. Therefore, in some embodiments, the antibody or the antigen-binding fragment thereof in the present disclosure has decreased or even eliminated effector functions (such as ADCC and/or CDC activity). An amino acid mutation in human IgG4 that stabilizes the structure of the antibody, such as S228P (in EU nomenclature, or S241 P in Kabat nomenclature), is also contemplated.

In such embodiments, the antibody or the antigen-binding fragment thereof in the present disclosure includes a variant of a heavy chain constant region of human IgG, where the variant has at least one of the following substitutions relative to a wild-type sequence from which the variant is derived: Ser228Pro, Leu234Ala, Leu235Ala, Gly237Ala, Asp265Ala, Asn297Ala, Pro329Ala, Asp356Glu and Leu358Met (these amino acid positions are positions based on an EU numbering system, Edelman G M et al, Proc Natl Acad USA, 63, 78-85 (1969). PMID: 5257969).

In some exemplary embodiments, the antibody or the antigen-binding fragment thereof in the present disclosure includes a variant of a heavy chain constant region of human IgG1, where the variant has the following substitution relative to a wild-type sequence from which the variant is derived: Leu234Ala or Leu235Ala (positions based on the EU numbering system). In such embodiments, the antibody or the antigen-binding fragment thereof in the present disclosure has decreased ADCC activity and CDC activity.

In some exemplary embodiments, the antibody or the antigen-binding fragment thereof in the present disclosure includes a variant of a heavy chain constant region of human IgG1, where the variant has the following substitution relative to a wild-type sequence from which the variant is derived: Asn297Ala (a position based on the EU numbering system). In such embodiments, the antibody or the antigen-binding fragment thereof in the present disclosure has eliminated ADCC activity.

In some exemplary embodiments, the antibody or the antigen-binding fragment thereof in the present disclosure includes a variant of a heavy chain constant region of human IgG1, where the variant has the following substitution relative to a wild-type sequence from which the variant is derived: Asp265Ala or Pro329Ala (positions based on the EU numbering system). In such embodiments, the antibody or the antigen-binding fragment thereof in the present disclosure has eliminated ADCC activity.

In some exemplary embodiments, the antibody or the antigen-binding fragment thereof in the present disclosure includes a variant of a heavy chain constant region of human IgG4, where the variant has the following substitution relative to a wild-type sequence from which the variant is derived: Ser228Pro (a position based on the EU numbering system). In such embodiments, the antibody or the antigen-binding fragment thereof in the present disclosure is stable in structure, can reduce Fab-arm exchange, and is not easy to produce an incomplete antibody.

In some preferred embodiments, a heavy chain of the antibody or the antigen-binding fragment thereof in the present disclosure includes a variant of a heavy chain constant region (CH) of a human immunoglobulin, where the variant has substantially unchanged effector functions relative to a wild-type sequence from which the variant is derived. In such embodiments, the variant has at most 20 conservative amino acid substitutions (for example, at most 15, at most 10 or at most 5 conservative substitutions, such as 1, 2, 3, 4 or 5 conservative substitutions) relative to a wild-type sequence from which the variant is derived.

In some preferred embodiments, the antibody or the antigen-binding fragment thereof in the present disclosure includes:
(a) a heavy chain, including an amino acid sequence selected from:
  (i) a sequence as shown by SEQ ID NO: 38;
  (ii) a sequence with one or more amino acid substitutions, deletions or additions (such as 1, 2, 3, 4 or 5 substitutions, deletions or additions) relative to the sequence as shown by SEQ ID NO: 38; or (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 38; and (b) a light chain, including an amino acid sequence selected from:

(iv) a sequence as shown by SEQ ID NO: 40;

(v) a sequence with one or more amino acid substitutions, deletions or additions (such as 1, 2, 3, 4 or 5 substitutions, deletions or additions) relative to the sequence as shown by SEQ ID NO: 40; or (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 40.

In some preferred embodiments, the substitutions in (ii) or (v) are conservative substitutions.

In some preferred embodiments, the antibody or the antigen-binding fragment thereof in the present disclosure includes:

(a) a heavy chain, including an amino acid sequence selected from:

(i) a sequence as shown by SEQ ID NO: 42;

(ii) a sequence with one or more amino acid substitutions, deletions or additions (such as 1, 2, 3, 4 or 5 substitutions, deletions or additions) relative to the sequence as shown by SEQ ID NO: 42; or (iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 42; and (b) a light chain, including an amino acid sequence selected from:

(iv) a sequence as shown by SEQ ID NO: 44;

(v) a sequence with one or more amino acid substitutions, deletions or additions (such as 1, 2, 3, 4 or 5 substitutions, deletions or additions) relative to the sequence as shown by SEQ ID NO: 44; or (vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by SEQ ID NO: 44.

In some preferred embodiments, the substitutions in (ii) or (v) are conservative substitutions.

In some exemplary embodiments, the antibody or the antigen-binding fragment thereof in the present disclosure includes:

(1) a heavy chain having a sequence as shown by SEQ ID NO: 38 and a light chain having a sequence as shown by SEQ ID NO: 40; or (2) a heavy chain having a sequence as shown by SEQ ID NO: 42 and a light chain having a sequence as shown by SEQ ID NO: 44.

The anti-TIM-3 antibody or the antigen-binding fragment thereof disclosed herein can inhibit, reduce or neutralize one or more kinds of activity of TIM-3, for example, block or reduce immune checkpoints on T cells or NK cells, or reactivate an immune response by adjusting antigen presenting cells.

In an embodiment, the antibody molecule or the antigen-binding fragment thereof may exhibit at least one of the following properties:

a) binding to TIM-3 (especially human TIM-3) at a KD of 100 nM or below, preferably 10 nM or below, 1 nM or below, 100 pM or below, or 1 pM or below;

b) promoting the proliferation of T cells (such as $CD4^+$ or $CD8^+$ T cells) in mixed lymphocyte reaction (MLR) assay;

c) promoting the production of interferon-γ (IFN-γ) in the MLR assay;

d) promoting the secretion of interleukin-2 (IL-2) in the MLR assay;

e) being cytotoxic (antibody-dependent cell-mediated cytotoxicity, ADCC) to cells expressing TIM-3, such as acute myeloid leukemia cells expressing TIM-3;

f) enhancing cytotoxic activity of NK cells;

g) reducing activity of repressors of regulatory T cells (Treg) or macrophages; or h) increasing an ability of macrophages or dendritic cells to stimulate an immune response.

In some preferred embodiments, the antibody or the antigen-binding fragment thereof in the present disclosure is derived from the following monoclonal antibody, or is the following monoclonal antibody:

a monoclonal antibody produced by hybridoma cell strain #22, where hybridoma cell strain #22 is deposited at China Center for Type Culture Collection (CCTCC) (address: WuHan University, Wuhan, China) and having a deposit number CCTCC NO. C2017181.

In some preferred embodiments, the antibody or the antigen-binding fragment thereof in the present disclosure is a chimeric antibody or a humanized antibody. In some preferred embodiments, the antibody or the antigen-binding fragment thereof in the present disclosure is selected from scFv, Fab, Fab', (Fab')2, an Fv fragment, a diabody, a bispecific antibody or a multi-specific antibody.

In a second aspect, disclosed is a nucleotide sequence for encoding the anti-TIM-3 antibody molecule of the present disclosure. In some embodiments, the nucleotide sequence for encoding the anti-TIM-3 antibody molecule is codon-optimized. For example, the present disclosure is characterized by a first nucleic acid and a second nucleic acid encoding the heavy chain variable region and the light chain variable region of the anti-TIM-3 antibody molecule, separately, where the antibody molecule is selected from any one of: Mab22, AB12S3, AB12S4, AB12S5, AB12S6, AB12S7, or a sequence substantially identical thereto. For example, the nucleic acid may include nucleotide sequences of AB12S3 and AB12S4 shown in Table 4 or sequences substantially identical thereto (e.g., sequences that have at least about 85%, 90%, 95%, 99% or more similarity, or sequence that have one or more nucleotide substitutions (such as conservative substitutions), or sequences that differ from the sequences shown in Table 4 by no more than 3, 6, 15, 30 or 45 nucleotides).

In a third aspect, the present disclosure provides a vector (such as a cloning vector or an expression vector), which includes the isolated nucleic acid molecule of the present disclosure. In some preferred embodiments, the vector of the present disclosure is, for example, a plasmid, a cosmid, a phage or the like. In some preferred embodiments, the vector can express the antibody or the antigen-binding fragment thereof in the present disclosure in a subject (for example, a mammal such as a human).

In a fourth aspect, the present disclosure provides a host cell, which includes the isolated nucleic acid molecule of the present disclosure or the vector of the present disclosure. The host cell may be a eukaryotic cell (e.g., a mammalian cell, an insect cell, a yeast cell) or a prokaryotic cell (e.g., *Escherichia coli*). Suitable eukaryotic cells include, but are not limited to, NSO cells, Vero cells, Hela cells, COS cells, CHO cells, HEK293 cells, BHK cells and MDCKII cells. Suitable insect cells include, but are not limited to, Sf9 cells. In some preferred embodiments, the host cell of the present disclosure is a mammalian cell, such as CHO (e.g., CHO-K1, CHO-S, CHO DXB11, and CHO DG44).

In a fifth aspect, the present disclosure provides a method for preparing the antibody or the antigen-binding fragment thereof in the present disclosure. The method includes: culturing the host cell of the present disclosure under a condition that expression of the antibody or the antigen-binding fragment thereof is allowed, and recovering the antibody or the antigen-binding fragment thereof from a culture of the cultured host cell.

In a sixth aspect, the present disclosure discloses a pharmaceutical composition, which includes a pharmaceutically acceptable carrier and/or excipient and/or stabilizer and at least one of the anti-TIM-3 antibody molecules described in the present disclosure.

In some preferred embodiments, the pharmaceutical composition may further include an additional pharmaceutically active agent. In some preferred embodiments, the additional pharmaceutically active agent is a medicament with antitumor activity. In some preferred embodiments, the additional pharmaceutically active agent is a medicament for treating infection. In some preferred embodiments, the additional pharmaceutically active agent is a medicament for treating autoimmune diseases.

In some preferred embodiments, in the pharmaceutical composition, the antibody or the antigen-binding fragment thereof in the present disclosure and the additional pharmaceutically active agent are provided as separate components or as components of a same composition. Therefore, the antibody or the antigen-binding fragment thereof in the present disclosure and the additional pharmaceutically active agent may be administered simultaneously, separately or sequentially.

In some embodiment, the pharmaceutical composition of the present disclosure further includes a second antibody that specifically binds to a receptor or a ligand or a nucleic acid encoding the second antibody, where the receptor or the ligand is selected from PD-1, PD-L1, PD-L2, LAG-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3 or any combination thereof.

In some particular embodiments, the second antibody is an antibody or an antigen-binding fragment thereof that binds to human PD-1. In some preferred embodiments, the pharmaceutical composition of the present disclosure includes an antibody or an antigen-binding fragment thereof that binds to human PD-1.

In some preferred embodiments, the antibody or the antigen-binding fragment thereof that binds to human PD-1, included in the pharmaceutical composition of the present disclosure, is selected from: Nivolumab (or Opdivo®) or an antigen binding fragment thereof, or Pembrolizumab (or Keytruda®) or an antigen-binding fragment thereof.

In some particular embodiments, the second antibody is an antibody or an antigen-binding fragment thereof that binds to human PD-L1. In some preferred embodiments, the pharmaceutical composition of the present disclosure includes an antibody or an antigen-binding fragment thereof that binds to human PD-L1.

In some embodiments, the antibody or the antigen-binding fragment thereof is used for preparing a medicament which is used for at least any one of: (1) improving activity of immune cells in vitro or in vivo in a subject (such as a human); (2) enhancing an immune response in a subject (such as a human); (3) treating cancer in a subject (such as a human); (4) treating an infectious disease in a subject (such as a human); (5) treating an autoimmune disease in a subject (such as a human); and (6) any combination of (1) to (5).

In a seventh aspect, the present disclosure provides use for preparing a medicament for treating a TIM-3 mediated disorder or disease (e.g., cancer, an infectious disease or an autoimmune disease) in a subject. The tumor is selected from a solid tumor, a hematological tumor (such as leukemia, lymphoma, myeloma such as multiple myeloma) or a metastatic lesion. Non-limiting examples of the cancer are selected from lung cancer (e.g., lung adenocarcinoma or non-small cell lung cancer (NSCLC) (e.g., NSCLC with a history of squamous and/or non-squamous disease, or NSCLC adenocarcinoma)), melanoma (e.g., advanced melanoma), renal cancer (e.g., renal cell carcinoma), liver cancer (e.g., hepatocellular carcinoma), myeloma (e.g., multiple myeloma), prostate cancer, breast cancer (e.g., breast cancer that does not express one, two or all of an estrogen receptor, a progesterone receptor or Her2/neu, for example, triple negative breast cancer), ovarian cancer, colorectal cancer, pancreatic cancer, head and neck cancer (for example, head and neck squamous cell carcinoma (HNSCC)), anal cancer, gastro-esophageal cancer (for example, esophageal squamous cell carcinoma), mesothelioma, nasopharyngeal cancer, thyroid cancer, cervical cancer, a lymphoproliferative disease (e.g., post-transplant lymphoproliferative disease) or hematological cancer (e.g. diffuse large B-cell lymphoma, T-cell lymphoma, B-cell lymphoma, or non-Hodgkin's lymphoma) or leukemia (e.g., myeloid leukemia or lymphocytic leukemia).

In an embodiment, the cancer is selected from advanced or metastatic cancer, melanoma or lung cancer such as non-small cell lung cancer.

In an embodiment, the cancer is lung cancer, e.g., lung adenocarcinoma, non-small cell lung cancer or small cell lung cancer.

In an embodiment, the cancer is melanoma, for example, advanced melanoma. In an embodiment, the cancer is advanced or unresectable melanoma that does not respond to other therapies. In other embodiments, the cancer is melanoma with a BRAF mutation (e.g., a BRAFV600 mutation).

In another embodiment, the cancer is liver cancer, for example, advanced liver cancer with or without viral infection, e.g., chronic viral hepatitis.

In another embodiment, the cancer is prostate cancer, e.g., advanced prostate cancer.

In another embodiment, the cancer is myeloma, e.g., multiple myeloma.

In another embodiment, the cancer is renal cancer, for example, renal cell carcinoma (RCC) (e.g., metastatic RCC or clear cell renal cell carcinoma (CCRCC) or renal papillary cell carcinoma).

In an embodiment, the tumor microenvironment has an elevated level of PD-L1 expression.

Alternatively, or in combination, the tumor microenvironment may have increased expression of IFNγ and/or CD8.

In some embodiments, the subject has been identified as or is identified as having a tumor that has one or more of a high PD-L1 level or high PD-L1 expression, or is identified as being tumor infiltrating lymphocyte (TIL)+, or both the aforementioned cases.

In some embodiments, the infectious disease is selected from viral infection, bacterial infection, fungal infection or parasitic infection. For example, non-limiting examples of the infectious disease include HIV, hepatitis virus (type A, type B or type C), herpes virus, sepsis or the like.

In some embodiments, the autoimmune disease is selected from rheumatoid arthritis, psoriasis, systemic lupus erythematosus, primary biliary cirrhosis, autoimmune hemolytic anemia, autoimmune thrombocytopenic purpura, insulin-dependent diabetes mellitus, Graves' disease, myasthenia gravis, autoimmune hepatitis and multiple sclerosis.

In an eighth aspect, the present disclosure provides a method for adjusting (e.g., stimulating or suppressing) an immune response in a subject. The method includes administering to the subject the anti-TIM-3 antibody molecule disclosed herein (e.g., a therapeutically effective amount of an anti-TIM-3 antibody molecule) alone or in combination with one or more active agents (e.g., in combination with other immunomodulators) or a surgery, so that the immune response in the subject is adjusted.

In some embodiments, the antibody molecule enhances, stimulates or increases the immune response in the subject. In some embodiments, the antibody molecule suppresses, reduces or neutralizes the immune response in the subject. The subject may be a mammal such as a monkey, a primate, preferably a higher primate such as a human (e.g., a patient suffering from or at risk of suffering from the disorder described in the present disclosure).

In a ninth aspect, the present disclosure provides a method for treating (e.g., suppressing and/or delaying progression) a cancer or a tumor in a subject. The method includes: administering to the subject the anti-TIM-3 antibody molecule described herein, e.g., a therapeutically effective amount of an anti-TIM-3 antibody molecule, alone or in combination with one or more active agents or procedures. In a particular embodiment, the anti-TIM-3 antibody molecule is administered in combination with a modulator of a costimulatory molecule (e.g., an agonist of a costimulatory molecule) or a modulator of an inhibitory molecule (e.g., an inhibitor of an immune checkpoint molecule), for example, as described in the present disclosure.

In a tenth aspect, the present disclosure further provides a method for reducing or suppressing the growth of cancer or tumor cells in a subject (for example, for treating cancer). The method includes: administering to the subject the anti-TIM-3 antibody molecule described herein, e.g., a therapeutically effective amount of an anti-TIM-3 antibody molecule, alone or in combination with a second active agent.

In an eleventh aspect, the present disclosure provides a diagnostic or therapeutic kit, which includes the anti-TIM-3 antibody molecule described herein and instructions for use.

The humanized antibody against TIM-3 prepared in the present disclosure binds to TIM-3 with high affinity and extremely strong specificity. In vivo anti-tumor research data shows that the humanized antibody provided by the present disclosure can significantly suppress the growth of transplanted tumors in mice, and even completely eliminate tumors in some mice. In addition, the antibody of the present disclosure is expressed in CHO cells, and has the advantages of a high yield, high activity, a simple purification process and a low production cost.

DETAILED DESCRIPTION

Abbreviations and Definitions

TIM-3 T-cell immunoglobulin and mucin domain 3
CDR Complementarity determining region in a variable region of an immunoglobulin, defined by the Kabat numbering system
$EC_{50}$ A concentration at which 50% efficacy or binding is effected
ELISA Enzyme-linked immunosorbent assay
FR Framework region of an antibody: a variable region of an immunoglobulin excluding the CDRs
HRP Horseradish peroxidase
IL-2 Interleukin 2
IFN Interferon
$IC_{50}$ A concentration at which 50% inhibition is effected
IgG Immunoglobulin G
Kabat Immunoglobulin comparison and numbering system advocated by Elvin A Kabat
mAb Monoclonal antibody
PCR Polymerase chain reaction
V region IgG chain segment whose sequence is variable among different antibodies.
It extends to Kabat residue 109 of the light chain and residue 113 of the heavy chain.
VH Heavy chain variable region of an immunoglobulin
VL Light chain variable region of an immunoglobulin
VK κ light chain variable region of an immunoglobulin
$K_D$ Equilibrium dissociation constant
Ka Association rate constant
Kd Dissociation rate constant The term "TIM-3" used in the present disclosure includes isotypes, mammalian (e.g., human) TIM-3, species homologs of human TIM-3, and analogs including at least one common epitope with TIM-3. The amino acid sequence of TIM-3 (e.g., human TIM-3) is known in the art (for example, Sabatos et al., Nat Immunol, 2003, 4 (11):1102). In some embodiments, the antibody molecule provided by the present disclosure specifically binds to an epitope (e.g., a linear or conformational epitope) on TIM-3 of a mammal (e.g., a human or a cynomolgus). In some embodiments, the binding epitope is at least a portion of an IgV domain of human or cynomolgus TIM-3. Nucleotide and protein sequences of human TIM-3 can be found in Genbank accession number AF251707.1 and Uniprot accession number Q8TDQ0.

The term "antibody" covers full-length antibodies (including two heavy chains and two light chains), various functional fragments thereof (which may only include, for example, an antigen-binding portion, such as Fab, Fab', F(ab')$_2$, Fc, Fd, Fd', Fv or scFv fragments) and modified antibodies (e.g., a humanized antibody, a glycosylated antibody, etc.). The present disclosure further includes an anti-TIM-3 antibody with a glycosylation modification.

In some applications, modifications are made to remove undesirable glycosylation sites, for example, fucose is removed from an oligosaccharide chain to enhance antibody-dependent cell-mediated cytotoxicity (ADCC). In other applications, galactosylation may be performed to change complement dependent cytotoxicity (CDC).

The anti-TIM-3 antibody molecule in the present disclosure may be a humanized, a chimeric, a camelid, shark or in vitro-generated antibody molecule. Antibodies and antibody fragments may originate from any antibody class, including but not limited to IgG, IgA, IgM, IgD, and IgE, and from any antibody subclass (e.g., IgG1, IgG2, IgG3 and IgG4).

The antibody may also be a human antibody, a humanized antibody, a CDR grafted antibody or an antibody produced in vitro. The antibody may have, for example, a heavy chain constant region selected from IgG1, IgG2, IgG3 or IgG4. The antibody may also have, for example, a light chain selected from κ or λ.

The term "monoclonal antibody or mAb" refers to an antibody obtained from a single cloned cell strain, where the cell strain is not limited to a eukaryotic, prokaryotic or phage cloned cell strain. The monoclonal antibody or the antigen-binding fragment may be obtained through, for example, hybridoma technology, recombination technology, phage display technology, synthesis technology (such as CDR-grafting) or recombinantly obtained by other existing technologies.

"Antibody fragments" and "antigen-binding fragments" refer to antigen-binding fragments and analogs of antibodies, which generally include at least part of an antigen-binding region or a variable region (for example, one or more CDRs) of a parental antibody. The antibody fragments retain at least part of the binding specificity of the parental antibody. Generally, when the activity is represented in moles, the antibody fragment retains at least 10% of parental binding activity. Preferably, the antibody fragment retains at least 20%, 50%, 70%, 80%, 90%, 95% or 100% or more of the binding affinity of the parental antibody to a target. Examples of antibody fragments include, but are not limited to: Fab, Fab', F(ab')$_2$ and Fv fragments, a diabody, a linear antibody, a single-chain antibody molecule such as ScFv, a single antibody, a nanobody and a single-domain antibody, and a multi-specific antibody composed of antibody fragments. Engineered antibody variants are summarized by Holliger et al., 2005; Nat Biotechnol, 23: 1126-1136.

A "Fab fragment" consists of one light chain and the CH1 and variable region of one heavy chain. The heavy chain of a Fab molecule cannot form a disulfide bond with another heavy chain molecule.

An "Fc" region contains two heavy chain fragments including the CH1 and CH2 domains of an antibody. The two heavy chain fragments are held together by two or more disulfide bonds under the hydrophobic effect of the CH3 domain.

A "Fab' fragment" contains one light chain, and the VH domain and the CH1 domain and the constant region between the CH1 domain and the CH2 domain of one heavy chain, so that an inter-chain disulfide bond can be formed between two heavy chains of two Fab' fragments to form a F(ab')2 molecule.

A "F(ab')$_2$ fragment" contains two light chains, and the VH domains and CH1 domains and constant regions between the CH1 domains and CH2 domains of two heavy chains, so that an inter-chain disulfide bond is formed between the two heavy chains. Therefore, the F(ab')$_2$ fragment is composed of two Fab' fragments held together by the disulfide bond between the two heavy chains.

An "Fv region" includes variable regions from both the heavy chain and the light chain and lacks constant regions.

A "single-chain Fv antibody" (or "scFv antibody") refers to an antibody fragment including VH and VL domains of an antibody, where these domains are present in a single polypeptide chain. For a summary of scFv, reference may be made to Pluckthun (1994), The Pharmacology of Monoclonal Antibodies, Vol. 113, edited by Rosenburg and Moore, Springer-Verlag, New York, pages 269-315. Reference may also be made to International Patent Application Publication No. WO 88/01649 and U.S. Pat. Nos. 4,946,778 and 5,260,203.

The "antigen-binding fragment" refers to an immunoglobulin fragment which includes only a heavy chain variable region or a light chain variable region, and has immunological functions. Examples of antigen-binding fragments include: (i) a Fab fragment which is a monovalent fragment composed of VL, VH, CL and CH1 domains; (ii) a F(ab')$_2$ fragment which is a bivalent fragment including two Fab fragments connected by a disulfide bond in the hinge region; (iii) a Fd fragment composed of VH and CH1 domains; (iv) a Fv fragment composed of VL and VH domains of a single arm of an antibody; (v) a diabody (dAb) fragment composed of a VH domain; (vi) a camelid (or a camelized variable domain); (vii) a single-chain Fv (scFv); (viii) a single-domain antibody. These antibody fragments can be obtained using any appropriate method including several conventional technologies known to those skilled in the art, and the use of the fragments can be screened in the same way as an intact antibody.

The term "hypervariable region", "CDR" or "complementarity determining region" used herein refers to amino acid residues of an antibody that are responsible for antigen binding. CDR sequences are amino acid residues within the variable region and may be defined by IMGT, Kabat, Chothia and AbM methods or identified by any CDR sequence determination method well-known in the art. CDRs of an antibody may be identified as hypervariable regions originally defined by Kabat et al., for example, residues 24-34 (L1), 50-56 (L2) and 89-97 (L3) in a light chain variable domain and residues 31-35 (H1), 50-65 (H2) and 95-102 (H3) in a heavy chain variable domain (see Kabat et al., 1991, Sequences of Proteins of Immunological Interest, 5th edition, Public Health Service, National Institutes of Health, Bethesda, Md.). CDR positions may be identified as being defined by a "hypervariable loop" (HVL) structure originally described by Chothia et al., for example, residues 26-32 (L1), 50-52 (L2) and 91-96 (L3) in the light chain variable domain and residues 26-32 (H1), 52-56 (H2) and 95-102 (H3) in the heavy chain variable domain (see Chothia et al., J Mol Biol, 1992, 227: 799-817; Tomlinson et al., J Mol Biol, 1992, 227: 776-798). ImMunoGeneTics (IMGT) also provides a numbering system for immunoglobulin variable regions including CDRs, and CDRs are defined according to IMGT numbering, for example, residues 27-32 (L1), 50-52 (L2) and 89-97 (L3) in the light chain variable domain and residues 26-35 (H1), 51-57 (H2) and 93-102 (H3) in the heavy chain variable domain (see Lefranc, M. P. et al., Dev Comp Immunol, 2003, 27: 55-77, which is incorporated herein by reference). Other methods for CDR identification include an "AbM definition" or a "contact definition" of CDRs. The "AbM definition" is a compromise between Kabat and Chothia and obtained using Oxford Molecular's AbM antibody modeling software. The "contact definition" of CDRs is based on observed contact with the antigen and described in MacCallum et al., 1996, J. Mol. Biol., 262: 732-745. In a "configuration definition" method of CDRs, CDR positions may be identified as residues that make enthalpic contributions to antigen binding (see Makabe et al., 2008, Journal of Biological Chemistry, 283: 1156-1166). The methods used in the present disclosure may define CDRs by use of or according to any one of these methods including but not limited to a Kabat definition, an IMGT definition, a Chothia definition, the AbM definition, the contact definition and/or the configuration definition.

In some embodiments, the anti-TIM-3 antibody molecule includes at least one, two or three complementarity determining regions (CDRs) from the heavy chain variable region of the antibody described in the present disclosure, where the antibody is, for example, any one selected from Mab22, AB12S3, AB12S4, AB12S5, AB12S6 and AB12S7, or as listed in Table 1, or encoded by the nucleotide sequences in Table 4, or a substantially identical sequence (e.g., with at least 80%, 85%, 90%, 92%, 95%, 97%, 98%, 99% or higher similarity or with one or more amino acid substitutions (e.g., conservative substitutions)) to any one of the above sequences. In some embodiments, the anti-TIM-3 antibody molecule includes at least one, two or three complementarity determining regions (CDRs) from the heavy chain variable region and the light chain variable region of the antibody described in the present disclosure, where the antibody is, for example, any one selected from Mab22, AB12S3, AB12S4, AB12S5, AB12S6 and AB12S7, or as listed in Table 1, or encoded by the nucleotide sequences in Table 4, or a substantially identical sequence (e.g., with at least 80%, 85%, 90%, 92%, 95%, 97%, 98%, 99% or higher similarity or with one or more amino acid substitutions (e.g., conservative substitutions)) to any one of the above sequences. In some embodiments, the anti-TIM-3 antibody molecule includes at least one, two, three, four, five or six CDRs from the heavy chain and light chain variable regions, where the heavy chain and light chain variable regions include amino acid sequences shown in Table 1 or encoded by the nucleotide sequences shown in Table 4. In some embodiments, relative to the CDRs shown in Table 1 or encoded by the nucleotide sequences shown in Table 4, one or more of the CDRs (or all the CDRs) have one, two, three, four, five, six or more changes such as amino acid substitutions (e.g. conservative substitutions), insertions or deletions.

The term "framework region", "variable framework region" or "FR" refers to residues in the variable domain other than the residues in the hypervariable region as defined by the present disclosure. In some embodiments, the light chain variable framework region or the heavy chain variable framework region of the anti-TIM-3 antibody molecule may be selected from: (a) a light or heavy chain variable framework region including at least 70%, 75%, 80%, 85%, 86%, 87%, 88%, 89%, 90%, 91%, 92%, 94%, 95%, 96%, 97%, 98%, 99% or preferably 100% of amino acid residues from a human light or heavy chain variable framework region (e.g., light or heavy chain variable framework region residues from a human mature antibody, a human germline sequence or a human consensus sequence); (b) a non-human framework region (e.g. a rodent framework); or (c) a non-human framework region that has been modified, e.g., to remove antigenic determinants or cytotoxic determinants, e.g., a deimmunized or partially humanized framework. In some embodiments, the light or heavy chain variable framework region includes a light or heavy chain variable framework region sequence that is at least 70%, 75%, 80%, 85%, 86%, 87%, 88%, 89%, 90%, 91%, 92%, 94%, 95%, 96%, 97%, 98%, 99% identical or identical to a framework region of a VL or VH fragment of a human germline gene. In some embodiments, the anti-TIM-3 antibody molecule includes a heavy chain variable region having at least 1, 2, 3, 4, 5, 6, 7, 10, 15, 20 or more changes (e.g., amino acid substitutions, insertions or deletions) from an amino acid sequence of, for example, the FR in the complete variable region (as shown in Table 1). In some embodiments, the anti-TIM-3 antibody molecule includes a light chain variable region having at least 1, 2, 3, 4, 5, 6, 7, 10, 15, 20 or more changes (e.g., amino acid substitutions, insertions or deletions) from an amino acid sequence of, for example, the FR in the complete variable region (as shown in Table 1).

The term "chimeric antibody" refers to an antibody obtained by fusing the variable region of a murine antibody with the constant region of a human antibody and can reduce an immune response induced by the murine antibody. Chimeric antibodies may be produced by any suitable recombinant DNA technology. Some technologies are known in the art (see PCT/US86/02269; EP184,187; EP171,496; EP173,494; WO86/01533; U.S. Pat. No. 4,816,567; EP125,023; Better et al., Science, 1988, 240: 1041-1043); Liu et al., PNAS, 1987, 84: 3439-3443; Liu et al., J Immunol, 1987, 139: 3521-3526; Sun et al., PNAS, 1987, 84: 214-218; Nishimura et al., Canc Res, 1987, 47: 999-1005; Wood et al., Nature, 1985, 314: 446-449; and Shaw et al., J Natl Cancer Inst, 1988, 80: 1553-1559). In a preferred embodiment of the present disclosure, the light chain variable region of the chimeric antibody against TIM-3 further includes a light chain FR of a murine κ chain, a murine λ chain or variants thereof. The heavy chain variable region of the chimeric antibody against TIM-3 further includes a heavy chain FR of murine IgG1, IgG2, IgG3 or variants thereof. The constant region of the human antibody may be selected from a heavy chain constant region of human IgG1, IgG2, IgG3, IgG4 or variants thereof, preferably a heavy chain constant region of human IgG1 or IgG4.

The term "multi-specific antibody" is obtained by coupling a first antibody or an antigen-binding fragment thereof with another antibody or an antigen-binding fragment thereof or an antibody analog, where each antibody or the antigen-binding fragment thereof or the antibody analog retains original binding specificity. For example, the multi-specific antibody is a trispecific antibody or a tetraspecific antibody. The term "bispecific antibody" refers to that the anti-TIM-3 antibody or the antigen-binding fragment thereof in the present disclosure may be derivatized or linked to another functional molecule such as another peptide or protein (e.g., a tumor-associated antigen, a cytokine and a cell surface receptor) to generate a bispecific antibody that binds to at least two different binding sites or target molecules. To produce the bispecific antibody of the present disclosure, the antibody of the present disclosure may be functionally linked (for example, by chemical coupling, gene fusion, non-covalent binding or other means) to one or more other binding molecules, such as another antibody, antibody fragment, peptide or binding mimetic, to produce the bispecific antibody. For example, the "bispecific antibody" includes two variable domains or ScFv units such that the antibody recognizes two different antigens.

The term "immunobinding" and "immunobinding property" used herein refers to a non-covalent interaction that occurs between an immunoglobulin molecule and an antigen for which the immunoglobulin is specific. The strength or affinity of the immunobinding interaction may be represented by the equilibrium dissociation constant ($K_D$) of the interaction, where the smaller the $K_D$, the higher the affinity. The immunobinding property of the selected polypeptide may be quantified using a method known in the art. One method involves the measurement of a rate at which an antigen binding site/antigen complex is formed and dissociated. Both the "association rate constant" (ka or kon) and the "dissociation rate constant" (kd or koff) may be calculated according to the concentration and an actual rate of association and dissociation. (See Malmqvist M, Nature, 1993, 361: 186-187). The ratio of kd/ka is equal to the dissociation constant $K_D$ (generally see Davies et al., Annual Rev Biochem, 1990, 59: 439-473). Any effective method may be used for measuring values of $K_D$, ka and kd. In a preferred embodiment, the dissociation constant is measured by a bioluminescent interferometry method (e.g., a ForteBio Octet method in Example 5.2). In other preferred embodiments, the dissociation constant may be measured using a surface plasmon resonance technique (such as Biacore) or Kinexa. The antibody of the present disclosure is considered to specifically bind to the TIM-3 epitope, when the equilibrium association constant ($K_D$) is ≤10 µM, preferably ≤100 nM, more preferably ≤10 nM, and most preferably ≤100 pM to about 1 pM.

Homologous Antibody

In yet another aspect, amino acid sequences included in the heavy and light chain variable regions of the antibody of the present disclosure are homologous with amino acid sequences of the preferred antibody described herein, and the antibody retains desired functional characteristics of the anti-TIM-3 antibody of the present disclosure.

For example, the present disclosure provides a humanized antibody that binds to TIM-3 or an antigen-binding fragment thereof, where the humanized antibody or the antigen-binding fragment thereof includes a heavy chain variable region and a light chain variable region, where (a) the heavy chain variable region includes an amino acid sequence that is at least 80% homologous with an amino acid sequence selected from SEQ ID NOs: 1, 3, 5, 7, 9 and 11; more preferably, the heavy chain variable region includes an amino acid sequence that is at least 85%, 90%, 95%, 96%, 97%, 98% or 99% homologous with an amino acid sequence selected from SEQ ID NOs: 1, 3, 5, 7, 9 and 11; (b) the light chain variable region includes an amino acid sequence that is at least 80% homologous with an amino acid sequence selected from SEQ ID NOs: 2, 4, 6, 8, 10 and 12; more preferably, the light chain variable region includes an amino acid sequence that is at least 85%, 90%, 95%, 96%, 97%, 98%, or 99% homologous with an amino acid sequence selected from SEQ ID NOs: 2, 4, 6, 8, 10 and 12.

Antibody with Conservative Modifications

The term "conservative modification" is intended to mean that the amino acid modification does not significantly affect or change the binding characteristics of the antibody containing the amino acid sequence. Such conservative modifications include amino acid substitutions, additions and deletions. A modification may be introduced into the antibody of the present disclosure by using a standard technology known in the art, such as a site-directed mutagenesis and a PCR-mediated mutagenesis. A conservative amino acid substitution refers to the substitution of an amino acid residue with an amino acid residue with a similar side chain. The families of amino acid residues with similar side chains have been described in detail in the art. These families include amino acids with basic side chains (such as lysine, arginine and histidine), amino acids with acidic side chains (such as aspartic acid and glutamic acid), amino acids with uncharged polar side chains (such as glycine, asparagine, glutamine, serine, threonine, tyrosine, cysteine and tryptophan), amino acids with non-polar side chains (such as alanine, valine, leucine, isoleucine, proline, phenylalanine and methionine), amino acids with β-branched side chains (such as threonine, valine and isoleucine) and amino acids with aromatic side chains (such as tyrosine, phenylalanine, tryptophan and histidine). Therefore, one or more amino acid residues in the CDRs of the antibody of the present disclosure may be substituted with other amino acid residues from the same side chain family.

Use of the Anti-TIM-3 Antibody

The anti-TIM-3 antibody molecule disclosed herein can inhibit, reduce or neutralize one or more kinds of activity of TIM-3, for example, block immune checkpoints on T cells or NK cells, or reactivate an immune response by adjusting antigen presenting cells. In an embodiment, the antibody molecule has one or more kinds of activity as follows: enhancing the secretion of IFN-γ and/or TNFα in T cells; enhancing the proliferation of T cells (such as $CD4^+$ or $CD8^+$ T cells); enhancing the cytotoxicity of NK cells; reducing suppressor activity of regulatory T cells (Treg) or macrophages; or increasing an ability of macrophages or dendritic cells to stimulate an immune response. Therefore, such antibody molecules can be used for treating or preventing diseases for which the immune response in a subject is desired to be enhanced, such as cancer, infectious diseases and autoimmune diseases.

Cancer

In some embodiments, the anti-TIM-3 antibody molecule is used for treating cancer in which TIM-3 is expressed. The cancer in which TIM-3 is expressed includes cervical cancer (Cao et al., PLOS One, 2013, 8 (1): e53834), lung cancer (Zhuang et al., Am J Clin Pathol, 2012, 137 (6): 978-985) (e.g., non-small cell lung cancer), acute myeloid leukemia (Kikushige et al., Cell Stem Cell, 2010, 7 (6): 708-17), diffuse large B-cell lymphoma, melanoma (Fourcade et al., JEM, 2010, 207 (10): 2175), renal cancer (e.g., renal cell carcinoma (RCC) such as renal clear cell carcinoma, renal papillary cell carcinoma or metastatic renal cell carcinoma), squamous cell carcinoma, esophageal squamous cell carcinoma, nasopharyngeal cancer, colorectal cancer, breast cancer (e.g., breast cancer that does not express one, two or all of an estrogen receptor protein, a progesterone receptor or Her2/neu, for example, triple negative breast cancer), mesothelioma, hepatocellular carcinoma and ovarian cancer. The cancer in which TIM-3 is expressed may be a metastatic cancer. In an embodiment, the anti-TIM-3 antibody molecule is used for treating cancer characterized by one or more of the following macrophage cell markers: LILRB4 (inhibitory receptor of macrophages), CD14, CD16, CD68, MSR1, SIGLEC1, TREM2, CD163, ITGAX, ITGAM, CD11b or CD11c. Examples of such cancer include, but are not limited to, diffuse large B-cell lymphoma, glioblastoma multiforme, kidney renal clear cell carcinoma, pancreatic adenocarcinoma, sarcoma, liver hepatocellular carcinoma, lung adenocarcinoma, kidney renal papillary cell carcinoma, cutaneous melanoma, brain low-grade glioma, lung squamous cell carcinoma, ovarian serous cystic adenocarcinoma, head and neck squamous cell carcinoma, breast invasive carcinoma, acute myeloid leukemia, cervical squamous cell carcinoma, endocervical adenocarcinoma, uterine cancer, colorectal cancer, uterine corpus endometrial carcinoma, thyroid cancer, bladder urothelial carcinoma, adrenal cortical carcinoma, kidney chromophobe and prostatic adenocarcinoma.

In some aspects, the present disclosure provides a method for adjusting (e.g., stimulating or suppressing) an immune response in a subject. The method includes administering to the subject the anti-TIM-3 antibody molecule disclosed herein (e.g., a therapeutically effective amount of anti-TIM-3 antibody molecules) alone or in combination with one or more active agents or a surgery (e.g., in combination with other immunomodulators), so that the immune response in the subject is adjusted. In some embodiments, the antibody molecule enhances, stimulates or increases the immune response in the subject. In some embodiments, the antibody molecule suppresses, reduces or neutralizes the immune response in the subject.

The subject may be a mammal, such as a monkey, a primate, preferably a higher primate, such as a human (e.g., a patient suffering from or at risk of suffering from the disease described herein). In some embodiments, the subject needs to enhance the immune response, and in some embodiments, the subject needs to suppress the immune response.

In an embodiment, the subject is suffering from or at risk of suffering from the disease described herein, for example, cancer and infectious diseases described herein. In a particular embodiment, the subject is immunocompromised or at risk of being immunocompromised. For example, the subject is undergoing or has undergone chemotherapy and/or radiotherapy. Alternatively, or in combination, the subject is immunocompromised or at risk of being immunocompromised due to infection.

In an aspect, the present disclosure provides a method for treating (e.g., suppressing and/or delaying progression) cancer or a tumor in a subject. The method includes: administering to the subject the anti-TIM-3 antibody molecule described herein, e.g., a therapeutically effective amount of the anti-TIM-3 antibody molecule, alone or in combination with one or more active agents or procedures. In a particular embodiment, the anti-TIM-3 antibody molecule is administered in combination with a modulator of a costimulatory molecule (e.g., an agonist of a costimulatory molecule) or a modulator of an inhibitory molecule (e.g., an inhibitor of an immune checkpoint molecule) as described herein, for example.

The present disclosure further provides a method for reducing or suppressing the growth of cancer or tumor cells in a subject (for example, for treating cancer). The method includes: administering to the subject the anti-TIM-3 antibody molecule described herein, e.g., a therapeutically effective amount of an anti-TIM-3 antibody molecule, alone or in combination with a second active agent.

In some embodiments, the cancer treated with the anti-TIM-3 antibody molecule (alone or in combination with one or more immunomodulators) includes, but is not limited to, a solid tumor, a hematological tumor (such as leukemia, lymphoma, myeloma such as multiple myeloma) and a metastatic lesion. In an embodiment, the cancer is a solid tumor. Examples of solid tumors include malignant tumors, for example, sarcoma and cancer such as adenocarcinomas of various organ systems, e.g., those affecting lung, breast, ovary, lymph, stomach and intestines (e.g., colon), anus, genitals, genitourinary tract (e.g., kidney, urethra, bladder cells, prostate), pharynx, CNS (e.g., brain, nerve or glial cells), head and neck, skin (e.g., melanoma) and pancreas, and adenocarcinomas including malignant tumors, e.g., colorectal cancer, renal cancer, renal cell carcinoma, liver cancer, non-small cell lung cancer, small intestinal carcinoma and esophageal cancer. The cancer may be early, mid-term, advanced or metastatic cancer.

In an embodiment, the cancer is selected from lung cancer (e.g., lung adenocarcinoma or non-small cell lung cancer (NSCLC) (e.g., NSCLC with a history of squamous and/or non-squamous disease, or NSCLC adenocarcinoma)), melanoma (e.g., advanced melanoma), renal cancer (e.g., renal cell carcinoma), liver cancer (e.g., hepatocellular carcinoma), myeloma (e.g., multiple myeloma), prostate cancer, breast cancer (e.g., breast cancer that does not express one, two or all of an estrogen receptor, a progesterone receptor or Her2/neu, for example, triple negative breast cancer), ovarian cancer, colorectal cancer, pancreatic cancer, head and neck cancer (for example, head and neck squamous cell carcinoma (HNSCC)), anal cancer, gastro-esophageal cancer (for example, esophageal squamous cell carcinoma), mesothelioma, nasopharyngeal cancer, thyroid cancer, cervical cancer, a lymphoproliferative disease (e.g., post-transplant lymphoproliferative disease) or hematological cancer (e.g. diffuse large B-cell lymphoma, T-cell lymphoma, B-cell lymphoma, or non-Hodgkin's lymphoma) or leukemia (e.g., myeloid leukemia or lymphocytic leukemia).

In another embodiment, the cancer is selected from cancer (e.g., advanced or metastatic cancer), melanoma or lung cancer such as non-small cell lung cancer.

In an embodiment, the cancer is lung cancer, e.g., lung adenocarcinoma, non-small cell lung cancer or small cell lung cancer.

In an embodiment, the cancer is melanoma, for example, advanced melanoma. In an embodiment, the cancer is advanced or unresectable melanoma that does not respond to other therapies. In other embodiments, the cancer is melanoma with a BRAF mutation (e.g., a BRAFV600 mutation).

In another embodiment, the cancer is liver cancer, for example, advanced liver cancer with or without viral infection, e.g., chronic viral hepatitis.

In another embodiment, the cancer is prostate cancer, e.g., advanced prostate cancer.

In another embodiment, the cancer is myeloma, e.g., multiple myeloma.

In another embodiment, the cancer is renal cancer, for example, renal cell carcinoma (RCC) (e.g., metastatic RCC or clear cell renal cell carcinoma (CCRCC) or renal papillary cell carcinoma).

In an embodiment, the cancer microenvironment has an elevated level of PD-L1 expression. Alternatively, or in combination, the cancer microenvironment may have increased expression of IFNγ and/or CD8.

In some embodiments, the subject has been identified as or is identified as having a tumor that has high PD-L1 expression, or is identified as being tumor infiltrating lymphocyte (TIL)$^+$ (with an increased number of TILs), or both the aforementioned cases. In some embodiments, the subject has or is identified as having a tumor that has high PD-L1 expression and is TIL$^+$. In some embodiments, the method described herein further includes identifying a subject based on having or being identified as having a tumor with high PD-L1 expression and TIL$^+$. In some embodiments, tumors that are TIL$^+$ are CD8-positive and IFNγ-positive. In some embodiments, the subject has or is identified as having a high percentage of cells that are positive for one, two or more of PD-L1, CD8 and/or IFNγ. In some embodiments, the subject has or is identified as having a high percentage of cells that are positive for all of PD-L1, CD8 and IFNγ. In some embodiments, the subject has or is identified as having one, two or more of PD-L1, CD8 and/or IFNγ, and has or is identified as having one or more of the following cancer: lung cancer such as squamous cell lung cancer or lung adenocarcinoma, head and neck cancer, squamous cell cervical cancer, stomach cancer, esophageal cancer, thyroid cancer, melanoma and/or nasopharyngeal carcinoma (NPC). In some embodiments, the method described herein further describes that the subject has or is identified as having one, two or more of PD-L1, CD8 and/or IFNγ, and has or is identified as having one or more of squamous cell lung cancer or lung adenocarcinoma, head and neck cancer, squamous cell cervical cancer, stomach cancer, thyroid cancer, melanoma and/or nasopharyngeal carcinoma.

In some embodiments, the subject has or is identified as having a tumor that has one, two or more of the following characteristics: high PD-1 expression, high TIM-3 expression and/or high level of infiltration of regulatory T cells in the tumor. In some embodiments, the subject has or is identified as having a tumor with a high PD-1 level, a high TIM-3 level and an elevated level of regulatory T cells in the tumor. In some embodiments, the method described herein further includes that the subject has or is identified as being based on one, two or more of the following characteristics: a high percentage of PD-1$^+$ cells, a high percentage of TIM-3$^+$ cells, and/or high level of infiltration of regulatory T cells in the tumor (for example, an increased number or percentage of Tregs are present in the tumor). In some embodiments, the method described herein further includes that the subject has or is identified as having one, two or more of the following characteristics: a high percentage of PD-1$^+$ cells, a high percentage of TIM-3$^+$ cells, and/or high level of infiltration of regulatory T cells in the tumor and has one or more of the following cancer: lung cancer (e.g., non-small cell lung cancer (NSCLC)), hepatocellular cancer (e.g., hepatocellular carcinoma), or ovarian cancer (such as ovarian cancer).

Infectious Disease

Based on the types of infectious organisms or substances involved, infections are broadly classified as bacterial infections, viral infections, fungal infections or parasitic infections. Other less common types of infection include, for example, infectious diseases involving rickettsiae, *mycoplasma* and substances that cause scrapie, bovine spongiform encephalopathy (BSE) and Prion's disease (e.g., a Kuru disease and a Creutzfeldt-Jakob disease). Examples of bacteria, viruses, fungi and parasites that cause infections are well-known in the art. An infection may be acute, subacute, chronic or latent, and the infection may be local or systemic. In multiple embodiments, the anti-TIM-3 antibody molecule may be used alone or in combination with a vaccine in an adjuvant form, so as to stimulate an immune response against, for example, pathogens or toxins. Examples of pathogens for which this treatment method may be particularly useful include pathogens for which currently no vaccine is particularly effective or pathogens for which conventional vaccines are not fully effective. These pathogens include, but are not limited to, HIV, hepatitis (A, B and C), influenza, herpes, Giardia, malaria, *Leishmania, Staphylococcus aureus* and *Pseudomonas aeruginosa*.

Some examples of infectious and pathogenic viruses treatable with the antibody against TIM-3 include herpes virus (e.g., VZV, HSV-1, HAV-6, HSV-II, CMV, and Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV virus, Dengue virus, papilloma virus, molluscum virus, polio virus, rabies virus, JC virus, arbo-encephalitis virus and Ebola virus (e.g. BDBV, EBOV, RESTV, SUDV, and TAFV).

Examples of inflammatory diseases that can be prevented, treated or managed according to the method of the present disclosure include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis and chronic inflammation caused by chronic viral or bacterial infections.

Therefore, the antibody and the antigen-binding fragment thereof in the present disclosure have practicability in the treatment of inflammatory and autoimmune diseases.

Autoimmune Disease

Down-regulation of an immune system is desirable in the treatment of inflammatory and autoimmune diseases and graft-versus-host diseases (GvHDs). Examples of autoimmune diseases that can be treated by administering the antibody of the present disclosure include, but are not limited to, alopeciagreata, ankylosing spondylitis, antiphospholipid syndrome, auto-immune Addison's disease, adrenal autoimmune disease, autoimmune hemolytic anemia, autoimmune hepatitis, autoimmune oophoritis and orchitis, autoimmune thrombocytopenia, Behcet's disease, bullous pemphigoid, cardiomyopathy, celiacsprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoidlupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenic purpura (ITP), IgA neuropathy, juvenile arthritis, lichen planus, lupus erythematosus, Meniere's disease, mixed connective tissue disease, multiple sclerosis, neuromyelitis optica (NMO), type 1 or immune mediated diabetes mellitus, myasthenia gravis, pemphigus vulgaris, pernicious anemia, polyarteritis nodosa, polychrondritis, polyglandular syndromes, polymyalgia rheumatic, polymyositis, dermatomyositis, primary agamma globulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-mansyndrome, systemic lupusery thematosus, lupus erythematosus, takayasu arteritis, temporal arteristis/giant cell arteritis, transverse myelitis, ulcerative colitis, uveitis, vasculitides (e.g., dermatitis herpetiformis and vasculitis), vitiligo and Wegener's granulomatosis.

Detection Method and Kit

In some aspects, the present disclosure provides a method for detecting (e.g., in vitro or in vivo) the presence or level of TIM-3 in a sample (for example, a biological sample, e.g., blood, serum, semen, urine or tissue biopsy samples (from, for example, a hyperproliferative or cancerous lesion)). The method may be used for evaluation (e.g., monitoring the treatment or progress, diagnosis and/or staging of the disease (e.g., immune disorder, cancer or infectious disease) of the present disclosure in a subject). The method may include: (i) contacting the sample with the anti-TIM-3 antibody molecule of the present disclosure under the condition where interaction is allowed or administering the anti-TIM-3 antibody molecule to the subject and (ii) detecting whether a complex is formed between the antibody molecule and the sample. The formation of the complex indicates the presence of TIM-3 and may indicate the suitability of or need for the treatment described herein. The method may involve, for example, immunohistochemistry, immunocytochemistry, flow cytometry, antibody molecule complexed magnetic beads, ELISA assay, PCR-technology (e.g., RT-PCR). Generally, the anti-TIM-3 antibody molecule used in in vivo and in vitro diagnostic methods is directly or indirectly labelled with a detectable substance to output a detection signal. Suitable detectable substances include various biologically active enzymes, prosthetic groups, fluorescent substances, luminescent substances and radioactive substances.

In another aspect, the present disclosure provides a kit including the antibody or the antigen-binding fragment thereof in the present disclosure. In some preferred embodiments, the antibody or the antigen-binding fragment thereof in the present disclosure bears a detectable label. In a preferred embodiment, the kit further includes a second antibody that specifically recognizes the antibody or the antigen-binding fragment thereof in the present disclosure. Preferably, the second antibody further includes a detectable label.

In the present disclosure, the detectable label may be any substance detectable by a fluorescence, spectroscopy, photochemical, biochemical, immunological, electrical, optical or chemical means. It is particularly preferable that such a label is applicable to immunological detection (for example, enzyme-linked immunoassay, radioimmunoassay, fluorescence immunoassay, chemiluminescence immunoassay, etc.). Such labels are well-known in the art and include, but are not limited to, enzymes (for example, horseradish peroxidase, alkaline phosphatase, β-galactosidase, urease, glucose oxidase, etc.), radionuclides (for example, 3H, 125I, 35S, 14C or 32P), fluorescent dyes (for example, fluorescein isothiocyanate (FITC), fluorescein, tetramethylrhodamine isothiocyanate (TRITC), phycoerythrin (PE), Texas red, rhodamine, quantum dots or cyanine dye derivatives (e.g., Cy7, Alexa 750)), acridine ester compounds, magnetic beads (such as Dynabeads®), calorimetric labels such as colloidal gold or colored glass or plastic (for example, polystyrene, polypropylene, latex, etc.) beads, and biotin for binding to avidin (for example, streptavidin) modified by the aforementioned labels. Patents for teaching the use of the label include, but are not limited to, U.S. Pat. Nos. 3,817,837, 3,850,752, 3,939,350, 3,996,345, 4,277,437, 4,275,149 and 4,366,241 (all of which are incorporated herein by reference). The labels covered in the present disclosure may be detected by methods known in the art. For example, a radioactive label may be detected using a photographic film or a scintillation calculator, and a fluorescent label may be detected using an optical detector to detect the emitted light. An enzyme label is generally detected by providing an enzyme with a substrate and detecting a reaction product produced under the action of the enzyme on the substrate, and a calorimetric label is detected by simply visualizing a colored label. In some embodiments, the detectable label as described above may be linked to a recombinant protein of the present disclosure through linkers of different lengths to reduce potential steric hindrance.

In another aspect, use of the antibody or the antigen-binding fragment thereof in the present disclosure for preparing a kit is provided, where the kit is used for detecting the presence or level of TIM-3 in a sample.

Pharmaceutical Composition and Combination Therapy

The antibody provided by the present disclosure may be used alone or in combination with other therapeutic agents or treatment methods. The antibody against TIM-3 may also be combined with standard cancer treatment.

In some preferred embodiments, the pharmaceutical composition may further include an additional pharmaceutically active agent. In some preferred embodiments, the additional pharmaceutically active agent is a medicament with antitumor activity. In some preferred embodiments, the additional pharmaceutically active agent is a medicament for treating infection. In some preferred embodiments, the additional pharmaceutically active agent is a medicament for treating autoimmune diseases.

In some preferred embodiments, in the pharmaceutical composition, the antibody or the antigen-binding fragment thereof in the present disclosure and the additional pharmaceutically active agent are provided as separate components or as components of a same composition. Therefore, the antibody or the antigen-binding fragment thereof in the present disclosure and the additional pharmaceutically active agent may be administered simultaneously, separately or sequentially.

In some embodiment, the pharmaceutical composition of the present disclosure further includes a second antibody that specifically binds to a receptor or a ligand or a nucleic acid encoding the second antibody, where the receptor or the ligand is selected from PD-1, PD-L1, PD-L2, LAG-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3 or any combination thereof.

In some particular embodiments, the second antibody is an antibody or an antigen-binding fragment thereof that binds to human PD-1. In some preferred embodiments, the pharmaceutical composition of the present disclosure includes an antibody or an antigen-binding fragment thereof that binds to human PD-1.

In some preferred embodiments, the antibody or the antigen-binding fragment thereof that binds to human PD-1, included in the pharmaceutical composition of the present disclosure, is selected from: Nivolumab (Opdivo®) or an antigen binding fragment thereof, or Pembrolizumab (Keytruda®) or an antigen-binding fragment thereof.

In some particular embodiments, the second antibody is an antibody or an antigen-binding fragment thereof that binds to human PD-L1. In some preferred embodiments, the pharmaceutical composition of the present disclosure includes an antibody or an antigen-binding fragment thereof that binds to human PD-L1.

In some embodiments, the antibody or the antigen-binding fragment thereof is used for preparing a medicament which is used for at least any one of: (1) improving activity of immune cells in vitro or in vivo in a subject (such as a human); (2) enhancing an immune response in a subject (such as a human); (3) treating cancer of a subject (such as a human); (4) treating an infectious disease in a subject (such as a human); (5) treating an autoimmune disease in a subject (such as a human); and (6) any combination of (1) to (5).

In some preferred embodiments, the cancer is selected from a solid tumor, a hematological tumor (such as leukemia, lymphoma, myeloma such as multiple myeloma) and a metastatic lesion; for example, including but not limited to, lung cancer, squamous cell lung cancer, melanoma, renal cancer, breast cancer, IM-TN breast cancer, colorectal cancer, leukemia or a metastatic lesion of the cancer.

In some preferred embodiments, the infectious disease is selected from viral infection, bacterial infection, fungal infection and parasitic infection, including but not limited to, HIV, hepatitis virus, herpes virus or sepsis.

In some preferred embodiments, the autoimmune disease is selected from rheumatoid arthritis, psoriasis, systemic lupus erythematosus, primary biliary cirrhosis, autoimmune hemolytic anemia, autoimmune thrombocytopenic purpura, insulin-dependent diabetes mellitus, Graves' disease, myasthenia gravis, autoimmune hepatitis and multiple sclerosis.

Derivatized Antibody

The antibody or the antigen-binding fragment thereof in the present disclosure may be derivatized, for example, be linked to another molecule (e.g., another polypeptide or protein). Generally, the derivatization (e.g., labeling) of the antibody or the antigen-binding fragment thereof will not adversely affect its binding to TIM-3 (especially human TIM-3). Therefore, the antibody or the antigen-binding fragment thereof in the present disclosure is intended to include such derivatized forms. For example, the antibody or the antigen-binding fragment thereof in the present disclosure may be functionally linked (by chemical coupling, gene fusion, non-covalent linkage or other means) to one or more other molecular groups, such as another antibody (for example, to form a bispecific antibody), detection reagent, pharmaceutical reagent and/or protein or polypeptide (for example, avidin or a polyhistidine tag) capable of mediating the binding of the antibody or the antigen-binding fragment thereof to another molecule.

One type of derivatized antibody (for example, the bispecific antibody) is produced by cross-linking two or more antibodies (of the same type or of different types). Methods for obtaining the bispecific antibody are well-known in the art. Examples of these methods include, but are not limited to, a chemical cross-linking method, a cell engineering method (hybrid hybridoma method) or a genetic engineering method.

Another type of derivatized antibody is an antibody linked to a therapeutic moiety. The therapeutic moiety in the present disclosure may be a bacterial toxin, a cytotoxic medicament or a radiotoxin. Examples of the therapeutic moiety include, but are not limited to, taxol, cytochalasin B, mitomycin, etoposide, vincristine or other anti-metabolites, alkylating agents, antibiotics or anti-mitotic medicaments.

Another type of derivatized antibody is a labeled antibody. For example, the antibody or the antigen-binding fragment thereof in the present disclosure may be linked to a detectable label. In the present disclosure, the detectable label may be any substance detectable by a fluorescence, spectroscopy, photochemical, biochemical, immunological, electrical, optical or chemical means. Such labels are well-known in the art and examples of the labels include, but are not limited to, enzymes (for example, horseradish peroxidase, alkaline phosphatase, β-galactosidase, urease, glucose oxidase, etc.), radionuclides (for example, 3H, 125I, 35S, 14C or 32P), fluorescent dyes (for example, fluorescein isothiocyanate (FITC), fluorescein, tetramethylrhodamine isothiocyanate (TRITC), phycoerythrin (PE), Texas red, rhodamine, quantum dots or cyanine dye derivatives (e.g., Cy7, Alexa 750)), acridine ester compounds, magnetic beads (such as Dynabeads®), calorimetric labels such as colloidal gold or colored glass or plastic (for example, polystyrene, polypropylene, latex, etc.) beads, and biotin for binding to avidin (for example, streptavidin) modified by the aforementioned label. Patents for teaching the use of the label include, but are not limited to, U.S. Pat. Nos. 3,817,837, 3,850,752, 3,939,350, 3,996,345, 4,277,437, 4,275,149 and 4,366,241 (all of which are incorporated herein by reference). The detectable label as described above may be detected by methods known in the art. For example, a radioactive label may be detected using a photographic film or a scintillation calculator, and a fluorescent label may be detected using an optical detector to detect the emitted light. An enzyme label is generally detected by providing an enzyme with a substrate and detecting a reaction product produced under the action of the enzyme on the substrate, and a calorimetric label is detected by simply visualizing a colored label. In some embodiments, such a label is applicable to immunological detection (for example, enzyme-linked immunoassay, radioimmunoassay, fluorescence immunoassay, chemiluminescence immunoassay, etc.). In some embodiments, the detectable label as described above may be linked to the antibody or the antigen-binding fragment thereof in the present disclosure through linkers of different lengths to reduce potential steric hindrance.

In addition, the antibody or the antigen-binding fragment thereof in the present disclosure may also be derivatized with chemical groups, such as polyethylene glycol (PEG), methyl, ethyl or glycosyl groups. These groups may be used for improving the biological properties of the antibody, for example, increasing a serum half-life.

Preparation of the Monoclonal Antibody

The monoclonal antibody (mAb) of the present disclosure may be prepared by a variety of technologies, including conventional monoclonal antibody methodology, such as a standard somatic hybridization technology described in Kohler and Milstein, Nature, 1975; 256: 495. Although a somatic hybridization process is preferred, other methods for preparing the monoclonal antibody, such as viral or oncogenic transformation of B lymphocytes, may also be used in principle.

A preferred animal system for preparing hybridomas is a murine system. The preparation of hybridomas in mice is a very complete process. Immunization schemes and technologies for isolating immunized splenocytes for fusion are known in the art. Fusion partners (such as murine myeloma cells) and fusion processes are also known.

In order to express the antibody or a fragment of the antibody, DNA encoding partial or full-length light and heavy chains may be obtained by a standard molecular biology technology (such as PCR amplification or cDNA cloning using hybridomas expressing a target antibody), and the DNA is inserted into an expression vector, so that the target gene is operatively linked to a transcription and translation control sequence and transfected into a host cell for expression. The expression host is preferably a eukaryotic expression vector, more preferably a mammalian cell such as CHO and its derivative cell lines.

The antibody may be purified by a known technology, such as affinity chromatography using protein A or protein G. Subsequently or alternatively, a specific antigen or an epitope thereof may be immobilized on a column to purify an immunospecific antibody through immunoaffinity chromatography. The purification of immunoglobulin is, for example, discussed by D. Wilkinson (published by The Scientist, Inc., Philadelphia PA, Vol. 14, No. 8 (Apr. 17, 2000), pages 25-28).

The chimeric or humanized antibody of the present disclosure may be prepared according to the sequence of the murine monoclonal antibody prepared above. DNA encoding heavy and light chains of immunoglobulin may be obtained from hybridomas of target mice and engineered using the standard molecular biology technology to include a non-murine (e.g., human) immunoglobulin sequence. For example, to create the chimeric antibody, murine variable regions may be linked to human constant regions by methods known in the art (see U.S. Pat. No. 4,816,567 to Cabilly et al., for example). Isolated DNA encoding the VH may be converted into a full-length heavy chain gene by operatively linking the DNA encoding the VH to another DNA molecule encoding heavy chain constant regions (CH1, CH2 and CH3). The sequences of human heavy chain constant region genes are known in the art (see Kabat, E. A. et al., 1991, Sequences of Proteins of Immunological Interest, Fifth Edition, U.S. Department of Health and Human Services, NIH Publication No. 91-3242, for example). DNA fragments including these regions may be obtained through standard PCR amplification. The heavy chain constant region may be a constant region of IgG1, IgG2, IgG3, IgG4, IgA, IgE, IgM or IgD, most preferably a constant region of IgG1 or IgG4.

To create the humanized antibody, a murine CDR may be inserted into a human framework sequence by methods known in the art (see U.S. Pat. No. 5,225,539 to Winter and U.S. Pat. Nos. 5,530,101, 5,585,089, 5,693,762 and 6,180,370 to Queen et al.). Transgenic animals may also be used for antibody humanization, for example, HuMAb mice (Medarex, Inc.) containing human immunoglobulin gene miniloci encoding unrearranged human heavy chain (μ and γ) and κ light chain immunoglobulin sequences plus targeted mutations that deactivate endogenous μ and κ chain loci (see Lonberg et al. (1994) Nature 368 (6474): 856-859, for example); or "KM mice™" carrying human heavy chain transgenes and human light chain transchromosomes (see Patent WO02/43478). Other methods of antibody humanization include a phage display technology.

The present disclosure is further described through the following examples which should not be construed as further limitations. All the drawings, all the reference documents and the contents of patents and published patent applications cited in the entire application are expressly incorporated herein by reference.

BRIEF DESCRIPTION OF DRAWINGS

FIG. 2 illustrates parallel comparisons between amino acid sequences of heavy chain variable regions of five humanized anti-human TIM-3 antibodies including AB12S3, AB12S4, AB12S5, AB12S6 and AB12S7, and a murine antibody Mab22.

FIG. 3 illustrates parallel comparisons between amino acid sequences of light chain variable regions of five humanized anti-human TIM-3 antibodies including AB12S3, AB12S4, AB12S5, AB12S6 and AB12S7, and a murine antibody Mab22.

FIG. 4 illustrates measurement of binding abilities of humanized antibodies to human TIM-3 antigen.

DETAILED DESCRIPTION

Figure 1:
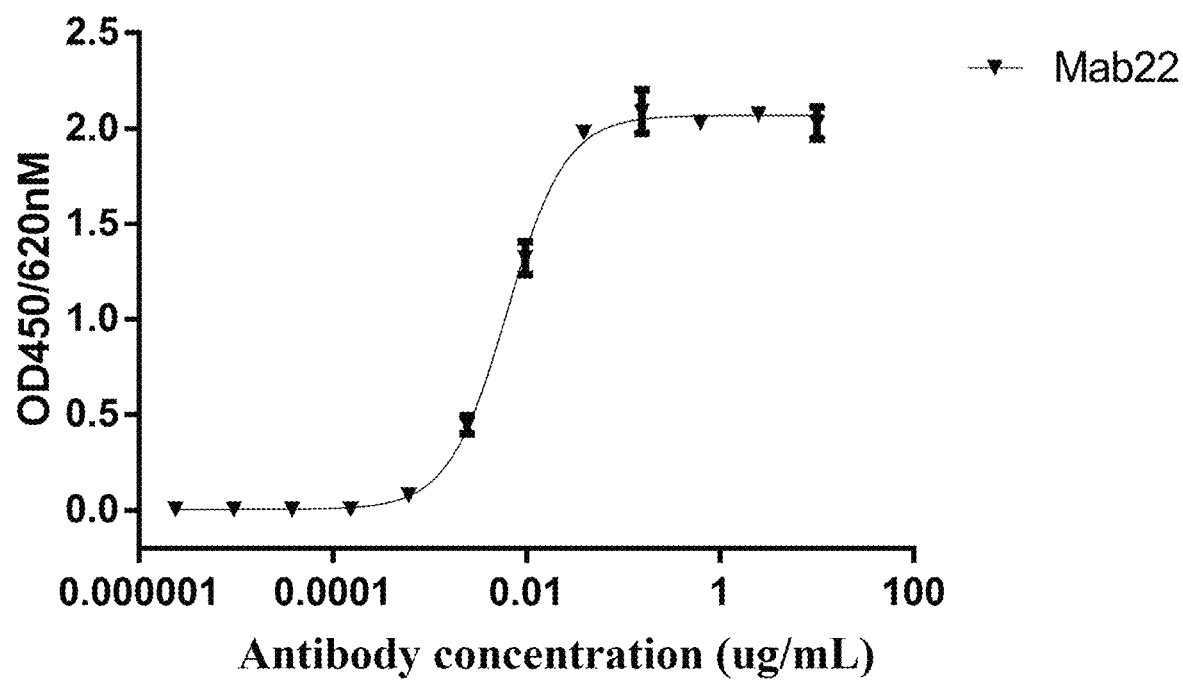
FIG. 1 illustrates measurement of the binding ability of a murine antibody to human TIM-3 antigen.

Example 1 Preparation of a Murine Monoclonal Antibody Against Human TIM-3

50 μg of human TIM-3 antigen (His-tagged TIM-3 extracellular domain expressed by Ampsource Biopharma Shanghai Inc. using a conventional method, protein sequence: Uniport entry No. Q8TDQ) was fully emulsified with Freund's complete adjuvant and immunized male Balb/C mice by a multi-site immunization method once every three weeks. On the 10th day after the third immunization, blood was sampled from the caudal vein, the titer of anti-human TIM-3 antibody in plasma was tested by ELISA to monitor the degree of immune response in mice, and then a mouse with the highest titer of anti-human TIM-3 antibody was boosted once 3 days before fusion. Three days later, the mouse was sacrificed and its spleen was removed and fused with a mouse Sp2/0 myeloma cell strain. $2\times10^8$ Sp2/0 cells were fused with $2\times10^8$ spleen cells in a solution of 50% polyethylene glycol (with a molecular weight of 1450) and 5% dimethyl sulfoxide (DMSO). The number of spleen cells was adjusted to $5\times10^5$/mL by using Iscove's medium (containing 10% fetal bovine serum, 100 U/mL penicillin, 100 μg/mL streptomycin, 0.1 mM hypoxanthine, 0.4 μM aminopterin and 16 μg thymidine), and 0.3 mL was added to the wells of a 96-well plate and placed in a 37° C., 5% $CO_2$ incubator. After 10 days of culture, clones where antibodies in the supernatant bind to TIM-3-His with high affinity were detected separately by high-throughput ELISA. Then the fused cells in the wells of the above monoclonal antibodies were subcloned. Positive wells that compete with human Galectin-9 to bind to TIM-3 were screened by a HTRF method (see tests for the anti-TIM-3 humanized antibody blocking the binding of TIM-3/Galectin-9 in Example 5.6) to obtain hybridoma cell strain #22.

A clone that produced a specific antibody was cultured in RPMI 1640 medium supplemented with 10% FCS. When the cell density reaches approximately $5\times10^5$ cells/mL, the medium was replaced with a serum-free medium. After 2 to 4 days, the cultured medium was centrifuged to collect the culture supernatant. The antibody was purified with protein G column. The eluent of the monoclonal antibody was dialyzed against 150 mM NaCl. The dialyzed solution was filtered and sterilized through a 0.2 μm filter to obtain the purified murine monoclonal antibody Mab22 to be tested.

Example 2 Determination of an Ability of a Murine Antibody to Bind to Human TIM-3 Antigen by ELISA A microtiter plate was coated with human TIM-3 (His-tagged TIM-3 extracellular domain expressed by Ampsource Biopharma Shanghai Inc., a protein sequence: Uniport entry No. Q8TDQ) overnight at room temperature. The coating solution was discarded, and the wells were blocked with skimmed milk dissolved in phosphate buffered saline (PBS) for 0.5 hours and washed with PBS containing 0.05% Tween-20. Then 50 μL of purified murine antibody Mab22 against human TIM-3 were added per well and incubated for 1 h at room temperature. The wells were washed with PBS containing 0.05% Tween 20. Then 50 μL of HRP-labeled goat anti-mouse IgG polyclonal antibody (purchased from Jackson Laboratory) were added per well as the detected antibody.

The results are shown in FIG. 1: the murine antibody Mab22 has higher affinity with human TIM-3, with $EC_{50}$ being 6.30 ng/mL.

Example 3 Subtype Identification and Variable Region Amplification of a Murine Anti-TIM-3 Monoclonal Antibody Antibody subtype identification: the culture supernatant of hybridoma cells was taken and the antibody subtype was identified using IsoStrip™ mouse monoclonal antibody subtype identification kit (from Santa Cruz Biotechnology and with catalog No. sc-24958). The subtype of the murine monoclonal antibody Mab22 was identified as IgG1 (Kappa) type.

Amplification of variable regions of the antibody: the candidate hybridoma cell #22 was cultured to 107 cells in total and centrifuged at 1000 rpm for 10 min to collect the cells. The total RNA was extracted with Trizol kit (Invitrogen), and the first strand of cDNA was synthesized with SMARTer RACE reverse transcription kit and used as a template for the subsequent amplification of DNA sequences of the variable regions of the antibody corresponding to the hybridoma cell. According to the subtype identification result, the heavy and light chain constant region sequences of the antibody subtype were acquired, and specific nested PCR primers were designed, where the primer sequences used in the amplification were complementary to the first framework region of the variable region and the constant region of the antibody. A target gene was amplified by a conventional PCR method, and the amplified product was sequenced to obtain heavy chain variable region sequence SEQ ID NO: 1 and light chain variable region sequence SEQ ID NO: 2 of the antibody Mab22 secreted by hybridoma clone #22. Hybridoma cell strain #22 was deposited at the China Center for Type Culture Collection (CCTCC) on Oct. 25, 2017 (deposit No. CCTCC NO. C2017181).

Example 4 Humanization of a Murine Anti-TIM-3 Monoclonal Antibody

According to the obtained sequences of the variable regions of the murine antibody Mab22, computer-aided three-dimensional modeling and structural analysis of the antibody were performed for antibody humanization. CDR-grafting is a common antibody humanization method to replace FRs of a murine antibody with FRs of a human antibody, so as to maintain activity and reduce immunogenicity. The method of the CDR-grafting for antibody humanization in combination with Discovery Studio analysis tool mainly includes the following steps: (1) 3D structural modeling of the antibody; (2) an analysis of key residues, where amino acid sequences of the variable regions and surrounding frameworks thereof are analyzed through molecular docking, and a spatial combination manner is investigated to determine the key residues that are essential for maintaining the conformation of the CDRs, including three main types: 1. residues located on a binding interface of the VL and the VH and playing a key role in the folding of the two domains; 2. residues close to the CDR and embedded in the protein; 3. residues that directly interact with the CDR, where the interaction includes hydrophobic interaction/hydrogen bonds/salt bridges; (3) the selection of a human template, where the human template needs to satisfy the following two conditions at the same time: firstly, the amino acid sequences of the antibody secreted by hybridoma cells are compared with the amino acid sequence of human germline antibodies to find a sequence with high homology; secondly, the framework sequence of a human germline antibody with low affinity to MHC II (HLA-DR) is selected to reduce immunogenicity; and (4) obtaining the sequence of the humanized antibody through reverse grafting based on the analysis of key residues.

Five humanized antibodies were obtained, namely AB12S3, AB12S4, AB12S5, AB12S6 and AB12S7. The amino acid sequences of the variable regions of the five humanized antibodies and their parental murine antibody are shown in Table 1.

TABLE 1

Amino acid sequences of the variable regions of the murine antibody Mab22 and the humanized antibodies derived therefrom

| | | | |
|---|---|---|---|
| Mab22 | | | |
| SEQ ID NO: 1 | VH | EVQLQLSGPELVKPGASVKMSCKASGYTFTN YVMHWMRQKPGQGLEWIGYIDPDNDGIKYNE KIKGKATLTSDKSSSTAYMELSSLTSEDSAV YYCARDFGYVDWFPYWGQGTLVTVSA | |
| SEQ ID NO: 2 | VL | DIVMTQSHKFMSTSVGNRVSITCKASQDVTT AVAWYQQKSGQSPKLLIYSASNRYIGVPDRF TGSGSGTDFTFTISSVQTEDLAVYYCQQHYS IPPTFGGGTNLEIK | |
| AB12S3 | | | |
| SEQ ID NO: 3 | VH | EVQLVQSGAEVKKPGASVKVSCKASGYTFTN YVMHWMRQAPGQRLEWIGYIDPDNDGIKYNE KIKGKATLTSDKSSSTAYMELSSLRSEDTAV YYCARDFGYVDWFPYWGQGTTVTVSS | |
| SEQ ID NO: 4 | VL | DIVMTQSPSSLSASVGDRVTITCKASQDVTT AVAWYQQKPGKAPKLLIYSASNRYIGVPDRF TGSGSGTDFTFTISSLQPEDIATYYCQQHYS IPPTFGGGTKVEIK | |
| AB12S4 | | | |
| SEQ ID NO: 5 | VH | EVQLVLSGAEVVKPGASVKMSCKASGYTFTN YVMHWMRQKPGQRLEWIGYIDPDNDGIKYNE KIKGKATLTSDKSSSTAYMELSSLRSEDSAV YYCARDFGYVDWFPYWGQGTTVTVSS | |
| SEQ ID NO: 6 | VL | DIVMTQSPSSMSTSVGDRVTITCKASQDVTT AVAWYQQKPGKSPKLLIYSASNRYIGVPDRF TGSGSGTDFTFTISSVQPEDIAVYYCQQHYS IPPTFGGGTNLEIK | |
| AB12S5 | | | |
| SEQ ID NO: 7 | VH | QVQLVQSGAEVKKPGASVKVSCKASGYTFT NYVMHWRQAPGQRLEWMGWIDPDNDGIKYS QKFQGRVTITRDTSASTAYMELSSLRSEDT AVYYCARDFGYVDWFPYWGQGTTVTVSS | |
| SEQ ID NO: 8 | VL | DIQMTQSPSSLSASVGDRVTITCQASQDVT TALNWYQQKPGKAPKLLIYSASNLETGVPS RFSGSGSGTDFTFTISSLQPEDIATYYCQQ HYSIPPTFGGGTKVEIK | |
| AB12S6 | | | |
| SEQ ID NO: 9 | VH | QVQLQLSGAEVKKPGASVKVSCKASGYTFT NYVMHWRQAPGQRLEWMGWIDPDNDGIKYS QKFQGRVTLTSDKSASTAYMELSSLRSEDT AVYYCARDFGYVDWFPYWGQGTLVTVSS | |
| SEQ ID NO: 10 | VL | DIQMTQSPSSMSASVGDRVTITCQASQDVT TALNWYQQKPGKSPKLLIYSASNLETGVPS RFSGSGSGTDFTFTISSLQPEDIATYYCQQ HYSIPPTFGGGTNLEIK | |

TABLE 1-continued

Amino acid sequences of the variable regions of the murine antibody Mab22 and the humanized antibodies derived therefrom

AB12S7

| | | |
|---|---|---|
| SEQ ID NO: 11 | VH | EVQLQLSGAEVKKPGASVKVSCKASGYTFT NYVMHWMRQKPGQRLEWMGWIDPDNDGIKY SQKFQGRVTITRDKSSSTAYMELSSLRSED TAVYYCARDFGYVDWFPYWGQGTLVTVSS |
| SEQ ID NO: 12 | VL | DIVMTQSPSSLSASVGDRVTITCQASQDVT TALNWYQQKSGQSPKLLIYSASNLETGVPS RFSGSGSGTDFTFTISSLQPEDIATYYCQQ HYSIPPTFGGGTNLEIK |

FIG. 2 shows parallel comparisons between the amino acid sequences of the heavy chain variable regions of the five humanized antibodies and the murine antibody Mab22. FIG. 3 shows parallel comparisons between the amino acid sequences of the light chain variable regions of the five humanized antibodies and the murine antibody Mab22. In the variable regions, complementarity determining regions (CDRs) and framework regions (FRs) are indicated, and the CDRs in the heavy and light chain variable regions are defined by the IMGT method.

The amino acid sequences of the CDRs included in the variable regions of the murine monoclonal antibody Mab22 and the five humanized antibodies derived therefrom, AB12S3, AB12S4, AB12S5, AB12S6 and AB12S7, are shown in Table 2 and defined by Kabat, Chothia and IMGT methods separately.

TABLE 2

Sequences of CDRs of the exemplary anti-TIM-3 antibody Mab22 and the humanized antibodies derived therefrom

| Antibody No. | CDR | Kabat | Chothia | IMGT |
|---|---|---|---|---|
| Mab22 | CDR-H1 | NYVMH (SEQ ID NO: 13) | GYTFTNY (SEQ ID NO: 16) | GYTFTNYV (SEQ ID NO: 18) |
| | CDR-H2 | YIDPDNDGIKYNEKIKG (SEQ ID NO: 14) | DPDNDG (SEQ ID NO: 17) | IDPDNDGI (SEQ ID NO: 19) |
| | CDR-H3 | DFGYVDWFPY (SEQ ID NO: 15) | DFGYVDWFPY (SEQ ID NO: 15) | ARDFGYVDWFPY (SEQ ID NO: 20) |
| | CDR-L1 | KASQDVTTAVA (SEQ ID NO: 21) | SQDVTTA (SEQ ID NO: 24) | QDVTTA (SEQ ID NO: 27) |
| | CDR-L2 | SASNRYI (SEQ ID NO: 22) | SAS (SEQ ID NO: 25) | SAS (SEQ ID NO: 25) |
| | CDR-L3 | QQHYSIPPT (SEQ ID NO: 23) | HYSIPP (SEQ ID NO: 26) | QQHYSIPPT (SEQ ID NO: 23) |
| AB12S3 | CDR-H1 | NYVMH (SEQ ID NO: 13) | GYTFTNY (SEQ ID NO: 16) | GYTFTNYV (SEQ ID NO: 18) |
| | CDR-H2 | YIDPDNDGIKYNEKIKG (SEQ ID NO: 14) | DPDNDG (SEQ ID NO: 17) | IDPDNDGI (SEQ ID NO: 19) |
| | CDR-H3 | DFGYVDWFPY (SEQ ID NO: 15) | DFGYVDWFPY (SEQ ID NO: 15) | ARDFGYVDWFPY (SEQ ID NO: 20) |
| | CDR-L1 | KASQDVTTAVA (SEQ ID NO: 21) | SQDVTTA (SEQ ID NO: 24) | QDVTTA (SEQ ID NO: 27) |
| | CDR-L2 | SASNRYI (SEQ ID NO: 22) | SAS (SEQ ID NO: 25) | SAS (SEQ ID NO: 25) |
| | CDR-L3 | QQHYSIPPT (SEQ ID NO: 23) | HYSIPP (SEQ ID NO: 26) | QQHYSIPPT (SEQ ID NO: 23) |
| AB12S4 | CDR-H1 | NYVMH (SEQ ID NO: 13) | GYTFTNY (SEQ ID NO: 16) | GYTFTNYV (SEQ ID NO: 18) |
| | CDR-H2 | YIDPDNDGIKYNEKIKG (SEQ ID NO: 14) | DPDNDG (SEQ ID NO: 17) | IDPDNDGI (SEQ ID NO: 19) |
| | CDR-H3 | DFGYVDWFPY (SEQ ID NO: 15) | DFGYVDWFPY (SEQ ID NO: 15) | ARDFGYVDWFPY (SEQ ID NO: 20) |
| | CDR-L1 | KASQDVTTAVA (SEQ ID NO: 21) | SQDVTTA (SEQ ID NO: 24) | QDVTTA (SEQ ID NO: 27) |
| | CDR-L2 | SASNRYI (SEQ ID NO: 22) | SAS (SEQ ID NO: 25) | SAS (SEQ ID NO: 25) |
| | CDR-L3 | QQHYSIPPT (SEQ ID NO: 23) | HYSIPP (SEQ ID NO: 26) | QQHYSIPPT (SEQ ID NO: 23) |
| AB12S5 | CDR-H1 | NYVMH (SEQ ID NO: 13) | GYTFTNY (SEQ ID NO: 16) | GYTFTNYV (SEQ ID NO: 18) |
| | CDR-H2 | WIDPDNDGIKYSQKFQG (SEQ ID NO: 28) | DPDNDG (SEQ ID NO: 17) | IDPDNDGI (SEQ ID NO: 19) |
| | CDR-H3 | DFGYVDWFPY (SEQ ID NO: 15) | DFGYVDWFPY (SEQ ID NO: 15) | ARDFGYVDWFPY (SEQ ID NO: 20) |
| | CDR-L1 | QASQDVTTALN (SEQ ID NO: 29) | SQDVTTA (SEQ ID NO: 24) | QDVTTA (SEQ ID NO: 27) |

TABLE 2-continued

Sequences of CDRs of the exemplary anti-TIM-3 antibody Mab22 and the humanized antibodies derived thereform

| Antibody No. | CDR | Kabat | Chothia | IMGT |
|---|---|---|---|---|
| | CDR-L2 | SASNLET (SEQ ID NO: 30) | SAS (SEQ ID NO: 25) | SAS (SEQ ID NO: 25) |
| | CDR-L3 | QQHYSIPPT (SEQ ID NO: 23) | HYSIPP (SEQ ID NO: 26) | QQHYSIPPT (SEQ ID NO: 23) |
| AB12S6 | CDR-H1 | NYVMH (SEQ ID NO: 13) | GYTFTNY (SEQ ID NO: 16) | GYTFTNYV (SEQ ID NO: 18) |
| | CDR-H2 | WIDPDNDGIKYSQKFQG (SEQ ID NO: 28) | DPDNDG (SEQ ID NO: 17) | IDPDNDGI (SEQ ID NO: 19) |
| | CDR-H3 | DFGYVDWFPY (SEQ ID NO: 15) | DFGYVDWFPY (SEQ ID NO: 15) | ARDFGYVDWFPY (SEQ ID NO: 20) |
| | CDR-L1 | QASQDVTTALN (SEQ ID NO: 29) | SQDVTTA (SEQ ID NO: 24) | QDVTTA (SEQ ID NO: 27) |
| | CDR-L2 | SASNLET (SEQ ID NO: 30) | SAS (SEQ ID NO: 25) | SAS (SEQ ID NO: 25) |
| | CDR-L3 | QQHYSIPPT (SEQ ID NO: 23) | HYSIPP (SEQ ID NO: 26) | QQHYSIPPT (SEQ ID NO: 23) |
| AB12S7 | CDR-H1 | NYVMH (SEQ ID NO: 13) | GYTFTNY (SEQ ID NO: 16) | GYTFTNYV (SEQ ID NO: 18) |
| | CDR-H2 | WIDPDNDGIKYSQKFQG (SEQ ID NO: 28) | DPDNDG (SEQ ID NO: 17) | IDPDNDGI (SEQ ID NO: 19) |
| | CDR-H3 | DFGYVDWFPY (SEQ ID NO: 15) | DFGYVDWFPY (SEQ ID NO: 15) | ARDFGYVDWFPY (SEQ ID NO: 20) |
| | CDR-L1 | QASQDVTTALN (SEQ ID NO: 29) | SQDVTTA (SEQ ID NO: 24) | QDVTTA (SEQ ID NO: 27) |
| | CDR-L2 | SASNLET (SEQ ID NO: 30) | SAS (SEQ ID NO: 25) | SAS (SEQ ID NO: 25) |
| | CDR-L3 | QQHYSIPPT (SEQ ID NO: 23) | HYSIPP (SEQ ID NO: 26) | QQHYSIPPT (SEQ ID NO: 23) |

To obtain a full-length antibody sequence consisting of two heavy chains and two light chains, the sequences of the VHs and the VLs shown in Table 1 were spliced or assembled with a heavy chain constant region (preferably from human IgG1 or IgG4) and a light chain constant region (preferably, from human κ light chain) of an antibody using conventional technologies. For example, in an embodiment, the anti-TIM-3 antibody molecule includes the heavy chain constant region of human wild-type IgG4 and the human κ light chain constant region shown in Table 3. Alternatively, a modified human IgG4 constant region sequence is used. For example, as shown in Table 3, the anti-TIM-3 antibody molecule includes human IgG4 with a mutation at position 228 (from S to P, for example) according to EU numbering. In another embodiment, the anti-TIM-3 antibody molecule includes the heavy chain constant region of human wild-type IgG1 and the human κ light chain constant region. Alternatively, a modified human IgG1 constant region sequence is used. For example, as shown in Table 3, human IgG1 includes a substitution at position 297 (for example, Asn substituted with Ala) according to EU numbering. In another embodiment, as shown in Table 3, human IgG1 includes a substitution at position 265 according to EU numbering, a substitution at position 329 according to EU numbering, or both substitutions (for example, Asp substituted with Ala at position 265 and/or Pro substituted with Ala at position 329). In another embodiment, as shown in Table 3, human IgG1 includes a substitution at position 234 according to EU numbering, a substitution at position 235 according to EU numbering, or both substitutions (for example, Leu substituted with Ala at position 234 and/or Leu substituted with Ala at position 235).

TABLE 3

Amino acid sequences of human IgG heavy chain constant regions and human K light chain constant region Amino acid sequence of Human K constant region SEQ ID NO: 31  RTVAAPSVFI FPPSDEQLKS GTASVVCLLN NFYPREAKVQ
               WKVDNALQSG NSQESVTEQD SKDSTYSLSS TLTLSKADYE
               KHKVYACEVT HQGLSSPVTK SFNRGEC Amino acid sequence of wild-type IgG1

SEQ ID NO: 32  ASTKGPSVFP LAPSSKSTSG GTAALGCLVK DYFPEPVTVS
               WNSGALTSGV HTFPAVLQSS GLYSLSSVVT VPSSSLGTQT
               YICNVNHKPS NTKVDKRVEP KSCDKTHTCP PCPAPELLGG

TABLE 3-continued

Amino acid sequences of human IgG heavy chain constant regions and human K light chain constant region

```
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK
```

Amino acid sequence of the constant region of IgG1
(N297A) mutant (EU numbering)

SEQ ID NO: 33
```
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPELLGG
PSVFLFPPKP KDTLMISRTP EVTCVVVDVS HEDPEVKFNW
YVDGVEVHNA KTKPREEQYA STYRVVSVLT VLHQDWLNGK
EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK
```

Amino acid sequence of the constant region of IgG1
(D265A, P329A) mutant (EU numbering)

SEQ ID NO: 34
```
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPELLGG
PSVFLFPPKP KDTLMISRTP EVTCVVVAVS HEDPEVKFNW
YVDGVEVHNA KTKPREEQYN STYRVVSVLT VLHQDWLNGK
EYKCKVSNKA LAAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK
```

Amino acid sequence of the constant region of IgG1
(L234A, L235A) mutant (EU numbering)

SEQ ID NO: 35
```
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPEAAGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK
```

Amino acid sequence of wild-type IgG4

SEQ ID NO: 36
```
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPSCP APEFLGGPSV
FLFPPKPKDT LMISRTPEVT CVVVDVSQED PEVQFNWYVD
GVEVHNAKTK PREEQFNSTY RVVSVLTVLH QDWLNGKEYK
CKVSNKGLPS SIEKTISKAK GQPREPQVYT LPPSQEEMTK
NQVSLTCLVK GFYPSDIAVE WESNGQPENN YKTTPPVLDS
DGSFFLYSRL TVDKSRWQEG NVFSCSVMHE ALHNHYTQKS
LSLSLGK
```

Amino acid sequence of the constant region of IgG4
(S228P) mutant (EU numbering)

SEQ ID NO: 37
```
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPPCP APEFLGGPSV
FLFPPKPKDT LMISRTPEVT CVVVDVSQED PEVQFNWYVD
GVEVHNAKTK PREEQFNSTY RVVSVLTVLH QDWLNGKEYK
CKVSNKGLPS SIEKTISKAK GQPREPQVYT LPPSQEEMTK
NQVSLTCLVK GFYPSDIAVE WESNGQPENN YKTTPPVLDS
DGSFFLYSRL TVDKSRWQEG NVFSCSVMHE ALHNHYTQKS
LSLSLGK
```

As shown in Table 4, the humanized antibodies AB12S3 and AB12S4 each include human IgG4 with a mutation at position 228 (from S to P) according to EU numbering and the human κ light chain constant region. Since ADCC and CDC effects are not required for the anti-TIM-3 antibody to function, human IgG4 is preferred for the constant regions of AB12S3 and AB12S4. However, IgG4 is prone to the formation of an incomplete antibody (Fab-arm exchange), so S228P modification can reduce the Fab-arm exchange.

TABLE 4

Amino acid sequences of the heavy and light chains of the humanized antibodies AB12S3 and AB12S4 and the corresponding nucleotide sequences

AB12S3

| | | | |
|---|---|---|---|
| SEQ ID NO: 38 | HC | | EVQLVQSGAEVKKPGASVKVSCKASGYTFTNYV GYVDWFPYWGQGTTVTVSSASTKGPSVFPLAP MHWMRQAPGQRLEWIGYIDPDNDGIKYNEKIKG CSRSTSESTAALGCLVKDYFPEPVTVSWNSGAL KATLTSDKSSSTAYMELSSLRSEDTAVYYCARDF TSGVHTFPAVLQSSGLYSLSSVVTVPSSSLGTKT YTCNVDHKPSNTKVDKRVESKYGPPCPPCPAPE FLGGPSVFLFPPKPKDTLMISRTPEVTCVVVDVS QEDPEVQFNWYVDGVEVHNAKTKPREEQFNST YRVVSVLTVLHQDWLNGKEYKCKVSNKGLPSSI EKTISKAKGQPREPQVYTLPPSQEEMTKNQVSL TCLVKGFYPSDIAVEWESNGQPENNYKTTPPVL DSDGSFFLYSRLTVDKSRWQEGNVFSCSVMHE ALHNHYTQKSLSLSLGK |
| SEQ ID NO: 39 | HC DNA | | GAGGTGCAGCTGGTGCAGTCCGGAGCTGAGG TGAAGAAGCCAGGAGCTTCCGTGAAGGTGAG CTGCAAGGCCTCTGGCTATACATTCACCAACTA CGTGATGCACTGGATGAGACAGGCTCCAGGA CAGCGCCTGGAGTGGATCGGCTATATCGACCC TGATAACGACGGCATCAAGTACAATGAGAAGAT CAAGGGCAAGGCCACACTGACCTCCGATAAGT CCAGCTCTACCGCTTACATGGAGCTGTCCAGC CTGAGAAGCGAGGACACAGCCGTGTACTATTG CGCTCGCGATTTTGGCTATGTGGACTGGTTCC CCTACTGGGGCCAGGGCACCACAGTGACCGT GTCTTCCGCCTCTACCAAGGGCCCTTCCGTGT TCCCTCTGGCCCCATGTTCCCGCAGCACCTCT GAGTCCACAGCCGCTCTGGGCTGCCTGGTGA AGGACTATTTCCCCGAGCCTGTGACCGTGTCC TGGAACAGCGGCGCTCTGACCTCCGGAGTGC ACACATTTCCCGCCGTGCTGCAGTCTTCCGGC CTGTACAGCCTGAGCTCTGTGGTGACCGTGC CATCCAGCTCTCTGGGCACCAAGACATATACC TGTAACGTGGATCATAAGCCCTCCAATACAAAG GTGGACAAGCGCGTGGAGAGCAAGTACGGAC CACCATGTCCTCCATGCCCAGCTCCCGAGTTT CTGGGCGGCCCTAGCGTGTTCCTGTTTCCCC CTAAGCCAAAGGATACCCTGATGATCAGCAGG ACCCCTGAGGTGACATGCGTGGTGGTGGACG TGTCCCAGGAGGACCCAGAGGTGCAGTTCAA CTGGTACGTGGACGGCGTGGAGGTGCACAAT GCCAAGACCAAGCCTCGGGAGGAGCAGTTTA ATTCCACCTACAGAGTGGTGAGCGTGCTGACA GTGCTGCATCAGGACTGGCTGAACGGCAAGG AGTATAAGTGTAAGGTGTCCAATAAGGGCCTG CCATCCAGCATCGAGAAGACCATCAGCAAGGC TAAGGGCCAGCCCAGGGAGCCTCAGGTGTAC ACACTGCCACCCTCTCAGGAGGAGATGACCAA GAACCAGGTGTCCCTGACATGCCTGGTGAAG GGCTTCTATCCTTCCGATATCGCCGTGGAGTG GGAGAGCAATGGCCAGCCAGAGAACAATTACA AGACCACACCTCCAGTGCTGGATTCTGACGGC TCCTTCTTTCTGTATTCCCGGCTGACCGTGGA CAAGAGCAGATGGCAGGAGGGCAACGTGTTT AGCTGTTCTGTGATGCATGAGGCTCTGCACAA TCATTACACACAGAAGTCCCTGAGCCTGTCTC TGGGCAAG |
| SEQ ID NO: 40 | LC | | DIVMTQSPSSLSASVGDRVTITCKASQDVTTAVA WYQQKPGKAPKLLIYSASNRYIGVPDRFTGSGS GTDFTFTISSLQPEDIATYYCQQHYSIPPTFGGG TKVEIKRTVAAPSVFIFPPSDEQLKSGTASVVCLL NNFYPREAKVQWKVDNALQSGNSQESVTEQDS KDSTYSLSSTLTLSKADYEKHKVYACEVTHQGLS SPVTKSFNRGEC |

TABLE 4-continued

Amino acid sequences of the heavy and light chains of the humanized antibodies AB12S3 and AB12S4 and the corresponding nucleotide sequences

| SEQ ID NO: 41 | LC DNA | GACATCGTGATGACACAGAGCCCTAGCTCTCT<br>GAGCGCCTCTGTGGGCGATAGAGTGACAATCA<br>CCTGTAAGGCTTCTCAGGACGTGACCACAGCC<br>GTGGCTTGGTACCAGCAGAAGCCCGGCAAGG<br>CCCCTAAGCTGCTGATCTATTCCGCTAGCAATA<br>GATACATCGGCGTGCCTGATCGCTTTACCGGC<br>TCTGGCTCCGGCACAGACTTTACATTCACCAT<br>CTCCAGCCTGCAGCCAGAGGACATCGCCACC<br>TACTATTGCCAGCAGCATTATAGCATCCCCCCT<br>ACCTTCGGCGGCGGCACAAAGGTGGAGATCA<br>AGAGGACCGTGGCTGCCCCCTCCGTGTTCAT<br>CTTTCCCCCTTCCGATGAGCAGCTGAAGTCCG<br>GCACAGCCAGCGTGGTGTGCCTGCTGAACAA<br>TTTCTACCCTAGAGAGGCTAAGGTGCAGTGGA<br>AGGTGGACAACGCCCTGCAGAGCGGCAATTC<br>TCAGGAGTCCGTGACCGAGCAGGATAGCAAG<br>GACTCTACATATTCCCTGTCCAGCACACTGACC<br>CTGAGCAAGGCTGATTACGAGAAGCACAAGGT<br>GTATGCCTGTGAGGTGACCCATCAGGGCCTGT<br>CTTCCCCTGTGACAAAGTCTTTCAACCGGGGC<br>GAGTGC |
|---|---|---|

AB12S4

| SEQ ID NO: 42 | HC | EVQLVLSGAEVVKPGASVKMSCKASGYTFTNYV<br>MHWMRQKPGQRLEWIGYIDPDNDGIKYNEKIKG<br>KATLTSDKSSSTAYMELSSLRSEDSAVYYCARDF<br>GYVDWFPYWGQGTTVTVSSASTKGPSVFPLAP<br>CSRSTSESTAALGCLVKDYFPEPVTVSWNSGAL<br>TSGVHTFPAVLQSSGLYSLSSVVTVPSSSLGTKT<br>YTCNVDHKPSNTKVDKRVESKYGPPCPPCPAPE<br>FLGGPSVFLFPPKPKDTLMISRTPEVTCVVVDVS<br>QEDPEVQFNWYVDGVEVHNAKTKPREEQFNST<br>YRVVSVLTVLHQDWLNGKEYKCKVSNKGLPSSI<br>EKTISKAKGQPREPQVYTLPPSQEEMTKNQVSL<br>TCLVKGFYPSDIAVEWESNGQPENNYKTTPPVL<br>DSDGSFFLYSRLTVDKSRWQEGNVFSCSVMHE<br>ALHNHYTQKSLSLSLGK |
|---|---|---|
| SEQ ID NO: 43 | HC DNA | GAGGTGCAGCTGGTGCTGTCCGGAGCTGAGG<br>TGGTGAAGCCAGGAGCTTCCGTGAAGATGAG<br>CTGCAAGGCCTCTGGCTATACATTCACCAACTA<br>CGTGATGCACTGGATGAGACAGAAGCCAGGA<br>CAGCGCCTGGAGTGGATCGGCTATATCGACCC<br>TGATAACGACGGCATCAAGTACAATGAGAAGAT<br>CAAGGGCAAGGCCACACTGACCTCCGATAAGT<br>CCAGCTCTACCGCTTACATGGAGCTGTCCAGC<br>CTGAGAAGCGAGGACAGCGCCGTGTACTATTG<br>CGCTCGCGATTTTGGCTATGTGGACTGGTTCC<br>CCTACTGGGGCCAGGGCACCACAGTGACCGT<br>GTCTTCCGCCTCTACCAAGGGCCCTTCCGTGT<br>TCCCTCTGGCCCCATGTTCCCGCAGCACCTCT<br>GAGTCCACAGCCGCTCTGGGCTGCCTGGTGA<br>AGGACTATTTCCCCGAGCCTGTGACCGTGTCC<br>TGGAACAGCGGCGCTCTGACCTCCGGAGTGC<br>ACACATTTCCCGCCGTGCTGCAGTCTTCCGGC<br>CTGTACAGCCTGAGCTCTGTGGTGACCGTGC<br>CATCCAGCTCTCTGGGCACCAAGACATATACC<br>TGTAACGTGGATCATAAGCCCTCCAATACAAAG<br>GTGGACAAGCGCGTGGAGAGCAAGTACGGAC<br>CACCATGTCCTCCATGCCCAGCTCCCGAGTTT<br>CTGGGCGGCCCTAGCGTGTTCCTGTTTCCCC<br>CTAAGCCAAAGGATACCCTGATGATCAGCAGG<br>ACCCCTGAGGTGACATGCGTGGTGGTGGACG<br>TGTCCCAGGAGGACCCAGAGGTGCAGTTCAA<br>CTGGTACGTGGACGGCGTGGAGGTGCACAAT<br>GCCAAGACCAAGCCTCGGGAGGAGCAGTTTA<br>ATTCCACCTACAGAGTGGTGAGCGTGCTGACA<br>GTGCTGCATCAGGACTGGCTGAACGGCAAGG<br>AGTATAAGTGTAAGGTGTCCAATAAGGGCCTG<br>CCATCCAGCATCGAGAAGACCATCAGCAAGGC<br>TAAGGGCCAGCCCAGGGAGCCTCAGGTGTAC<br>ACACTGCCACCCTCTCAGGAGGAGATGACCAA<br>GAACCAGGTGTCCCTGACATGCCTGGTGAAG<br>GGCTTCTATCCTTCCGATATCGCCGTGGAGTG<br>GGAGAGCAATGGCCAGCCAGAGAACAATTACA |

TABLE 4-continued

Amino acid sequences of the heavy and light chains of the humanized antibodies AB12S3 and AB12S4 and the corresponding nucleotide sequences

|  |  |  |
|---|---|---|
|  |  | AGACCACACCTCCAGTGCTGGATTCTGACGGC<br>TCCTTCTTTCTGTATTCCCGGCTGACCGTGGA<br>CAAGAGCAGATGGCAGGAGGGCAACGTGTTT<br>AGCTGTTCTGTGATGCATGAGGCTCTGCACAA<br>TCATTACACACAGAAGTCCCTGAGCCTGTCTC<br>TGGGCAAG |
| SEQ ID NO: 44 | LC | DIVMTQSPSSMSTSVGDRVTITCKASQDVTTAVA<br>WYQQKPGKSPKLLIYSASNRYIGVPDRFTGSGS<br>GTDFTFTISSVQPEDIAVYYCQQHYSIPPTFGGG<br>TNLEIKRTVAAPSVFIFPPSDEQLKSGTASVVCLL<br>NNFYPREAKVQWKVDNALQSGNSQESVTEQDS<br>KDSTYSLSSTLTLSKADYEKHKVYACEVTHQGLS<br>SPVTKSFNRGEC |
| SEQ ID NO: 45 | LC DNA | GACATCGTGATGACACAGAGCCCTAGCTCTAT<br>GAGCACCTCTGTGGGCGATAGAGTGACAATCA<br>CCTGTAAGGCTTCTCAGGACGTGACCACAGCC<br>GTGGCTTGGTACCAGCAGAAGCCCGGCAAGA<br>GCCCTAAGCTGCTGATCTATTCCGCTAGCAATA<br>GATACATCGGCGTGCCTGATCGCTTTACCGGC<br>TCTGGCTCCGGCACAGACTTTACATTCACCAT<br>CTCCAGCGTGCAGCCAGAGGACATCGCCGTG<br>TACTATTGCCAGCAGCATTATAGCATCCCCCCT<br>ACCTTCGGCGGCGGCACAAATCTGGAGATCAA<br>GAGGACCGTGGCTGCCCCCTCCGTGTTCATC<br>TTTCCCCCTTCCGATGAGCAGCTGAAGTCCGG<br>CACAGCCAGCGTGGTGTGCCTGCTGAACAATT<br>TCTACCCTAGAGAGGCTAAGGTGCAGTGGAAG<br>GTGGACAACGCCCTGCAGAGCGGCAATTCTC<br>AGGAGTCCGTGACCGAGCAGGATAGCAAGGA<br>CTCTACATATTCCCTGTCCAGCACACTGACCCT<br>GAGCAAGGCTGATTACGAGAAGCACAAGGTGT<br>ATGCCTGTGAGGTGACCCATCAGGGCCTGTCT<br>TCCCCTGTGACAAAGTCTTTCAACCGGGGCGA<br>GTGC |

Example 5 Qualities of Anti-TIM-3 Humanized Antibodies

5.1 Determination of Abilities of Anti-TIM-3 Humanized Antibodies to Bind to Human TIM-3

The abilities of the humanized antibodies AB12S3 and AB12S4 to bind to human TIM-3 (His-tagged TIM-3 extracellular domain expressed by Ampsource Biopharma Shanghai Inc., protein sequence: Uniport entry No. Q8TDQ) antigen were determined by a conventional ELISA method, and the detailed method is the same as that in Example 2. The results are shown in FIG. 4. The humanized antibodies AB12S3 and AB12S4 can both specifically bind to the human TIM-3 antigen as control antibody AB12S1 (the sequences of the variable regions of AB12S1 are derived from anti-TIM-3 antibody ABTIM3 in U.S. Pat. No. 9,605,070, and the amino acid sequence of its heavy chain is SEQ ID NO: 46 and the amino acid sequence of its light chain is SEQ ID NO: 47 in the present disclosure). However, another humanized IgG-irrelevant antibody, used as negative control, cannot bind to human TIM-3.

5.2 Tests on the Affinity Analysis of Anti-TIM-3 Humanized Antibodies

The binding affinity constants of the purified humanized antibodies AB12S3, AB12S4, AB12S5, AB12S6 and AB12S7 to the antigen were determined by bio-layer interferometry (BLI) (with ForteBio Octet RED&QK system from PALL). A polyclonal antibody against human IgG Fc was immobilized on the surface of a CM5 chip by an amino coupling method. The humanized antibody was flowed over and interacted with the polyclonal antibody to be captured on the surface of the chip. Antigen proteins, as mobile phases, were flowed over the surface of the antibody and interacted with the antibody. The obtained data was processed, and experimental data was fitted using a 1:1 binding model with Biacore T200 analysis software. The fitted data substantially coincided with the experimental data. Association and dissociation rate constants ka and kd were obtained. The Equilibrium dissociation constant $K_D$ was obtained by dividing ka by kd (see Table 5). The results show that the affinity of the obtained humanized antibodies has no significant losses, and the binding affinity of candidate antibodies AB12S3, AB12S4, AB12S5, AB12S6 and AB12S7 to human TIM-3 is comparable to that of the murine antibody Mab22, there $K_D$ values all reach a pM level. The humanized antibodies well maintain the affinity of the parental murine monoclonal antibody and greatly reduce the immunogenicity of the parental murine monoclonal antibody.

TABLE 5

Results of the determination of the affinity of the antibodies

| Ab | KD (M) | Ka (1/Ms) | Kd (1/s) |
|---|---|---|---|
| AB12S3 | 2.711E−12 | 2.51E+05 | 6.806E−07 |
| AB12S4 | <1.0E−12 | 2.54E+05 | <1.0E−07 |
| AB12S5 | 4.821E−12 | 1.31E+05 | 6.315E−07 |

TABLE 5-continued

Results of the determination of the affinity of the antibodies

| Ab | KD (M) | Ka (1/Ms) | Kd (1/s) |
|---|---|---|---|
| AB12S6 | 4.382E−12 | 1.98E+05 | 8.676E−07 |
| AB12S7 | 3.437E−12 | 2.23E+05 | 7.664E−07 |
| Mab22 | <1.0E−12 | 3.45E+05 | <1.0E−07 |

5.3 Determination of Tm Values of Anti-TIM-3 Humanized Antibodies

The Tm values of anti-TIM-3 antibodies were determined by a differential scanning fluorimetry (DSF) method. Detailed experimental steps are as follows: AB12S1, AB12S3 and AB12S4 were diluted with PBS to 1 mg/mL, and 12.5 μL of AB12S1, 12.5 μL of AB12S3 and 12.5 μL of AB12S4 were each added with 5 μL of 40×SYPRO Orange dye (from Life Technologies and with catalog No. 4306737) and 7.5 μL of ddH$_2$O. Then the above samples were each added to and reacted in a Q-PCR system (Applied Biosystems ABI 7500), where Q-PCR parameters were set as follows: Target (ROX), programs (25° C., 3 min; 1% rate, 95° C.; 95° C., 2 min).

Figure 5:
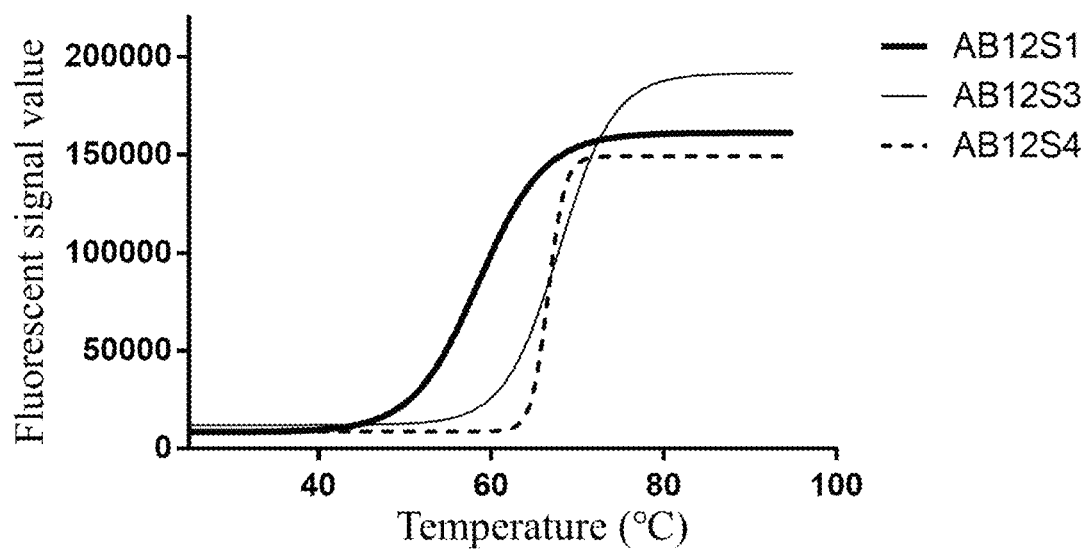
FIG. 5 illustrates measurement of Tm values of humanized antibodies.

The results are shown in FIG. 5. The Tm value (67.89° C.) of candidate antibody AB12S3 and the Tm value (66.61° C.) of candidate antibody AB12S4 are at least 8° C. higher than that of control antibody AB12S1 (58.54° C.). Therefore, it can be specified that the humanized antibodies AB12S3 and AB12S4 prepared by the present disclosure each have better thermal stability.

5.4 Determination of Cross-Reactivity of Anti-TIM-3 Humanized Antibodies with Different Species The cross-reactivity of the anti-TIM-3 humanized antibody AB12S3 with TIM-3 antigens from different species was determined by a conventional ELISA method.

Detailed experimental steps: Microtiter plates were coated with 100 μL of human TIM-3 (His-tagged TIM-3 extracellular domain expressed by Ampsource Biopharma Shanghai Inc., protein sequence: Uniport entry No. Q8TDQ), 100 μL of monkey TIM-3 (from Sino Biological Inc. and with catalog No. 90312-C02H), 100 μL of mouse TIM-3 protein (from Sino Biological Inc. with catalog No. 51152-M08H), each at 1 μg/mL, overnight at room temperature. The coating solution was discarded, and the wells were blocked with skimmed milk dissolved in phosphate buffered saline (PBS) for 0.5 hours and washed with PBS containing 0.05% Tween-20. Then 50 μL of purified HRP-labeled antibody AB12S3 were added per well, incubated for 1 h at room temperature, and washed 5 times with PBS containing 0.05% Tween-20. 100 μL of TMB were added to corresponding wells, and developed at room temperature for 5 min. 50 μL of 2N H$_2$SO$_4$ were added to stop, and read with a microplate reader at 450 nm. The results were imported into Graph Prism, and EC$_{50}$ values were calculated.

Figure 6:
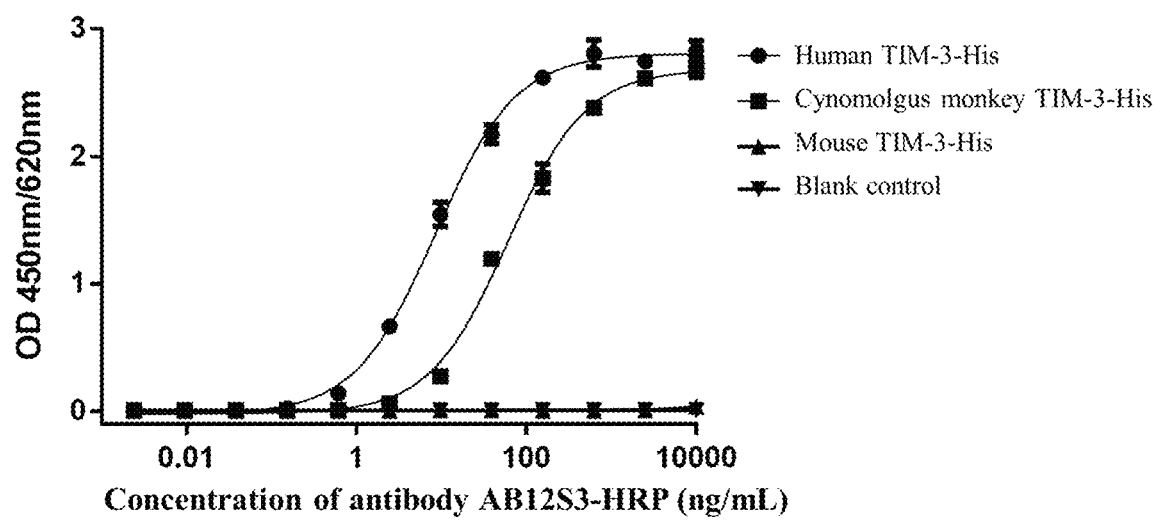
FIG. 6 illustrates measurement of affinity of antibody AB12S3 to TIM-3 antigens from different species by ELISA.

As shown in FIG. 6, the results indicate that AB12S3 can bind to human TIM-3 and monkey TIM-3 rather than murine TIM-3.

5.5 Determination of the Specificity of an Anti-TIM-3 Humanized Antibody

Human TIM-3 is homologous with TIM-1 and TIM-4 proteins. Whether an anti-TIM-3 humanized antibody AB12S3 specifically binds to human TIM-3 proteins was verified by an ELISA method.

Detailed experimental steps: human TIM-1 (from Sino Biological Inc. and with catalog No. 11051-H08H1), human TIM-3 (from Sino Biological Inc. and with catalog No. 10390-H08H), human TIM-4 (from Sino Biological Inc. with catalog No. 12161-H08H) were diluted to 1 μg/mL with pH9.6 carbonic acid buffer, and 100 μL/well were used to coat microtiter plates overnight at 4° C.; the wells were washed once with 300 μL of PBST, added with 200 μL of PBS solution containing 2% BSA, and blocked for 2 h at 37° C.; AB12S3 was diluted with a PBST solution containing 2% BSA, with a starting concentration of 10 μg/mL, by 4 fold, to obtain a total of 11 concentration gradients, and 100 μL were added per well to corresponding wells and incubated for 2 h at 37° C.; the wells were washed 3 times with 300 μL of PBST; HRP-labeled goat anti-human IgG (Jackson Immuno Research) was diluted at 1:10000 with the PBS solution containing 2% BSA, and 100 μL were added per well to corresponding wells and incubated at 37° C. for 1 h; the wells were washed 5 times with 300 μL of PBST; 100 μL of TMB substrate was added per well to corresponding wells, and developed at room temperature for 5 min; then 50 μL of 1M H$_2$SO$_4$ solution was added to stop. The absorbance was determined by a microplate reader at 450 nm. The results were imported into Graph Prism and EC$_{50}$ values were calculated.

Figure 7:
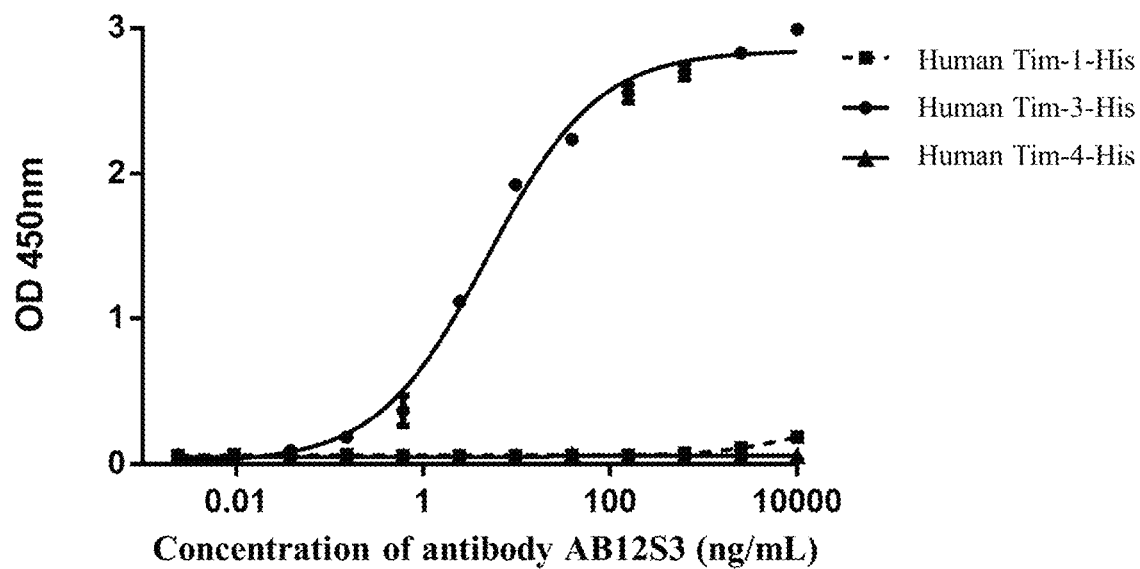
FIG. 7 illustrates measurement of specific binding of antibody AB12S3 to TIM-3 antigens by ELISA.

As shown in FIG. 7, the results indicate that AB12S3 specifically binds to human TIM-3 proteins rather than human TIM-1 and human TIM-4 proteins.

5.6 Detection of an Anti-TIM-3 Humanized Antibody Blocking the Binding of TIM-3/Galectin-9

HTRF is short for homogeneous time-resolved fluorescence. The HTRF analyzes the binding effects of molecules through wavelength detection. When biomolecules interact, two excitation lights at 620 nm and 665 nm are present; when the biomolecules do not interact, only one excitation light at 620 nm is present.

The effect of the anti-TIM-3 humanized antibody in blocking the binding of TIM-3/Galectin-9 was determined using a TIM-3/Gal9 binding assay kit (Cibio, catalog No. 63ADK000CTLPEF) operated according to the method described in the instructions. Detailed experimental steps: antibodies AB12S1 and AB12S3 were diluted with PBS to 10000 ng/mL, 1000 ng/mL 100 ng/mL, 10 ng/mL and 1 ng/mL, respectively. A 384-well fluorescent plate was used, 4 μL of 5 nM TIM3-Euk solution was added per well, 2 μL of diluted antibody was added, and then 4 μL of 40 nM Tag-Gal9 was added per well, and the wells were incubated at room temperature for 5 min. Finally, 4 μL of Anti-Tag-XL665 was added per well, and the 384-well plate was sealed with a sealing film and incubated at room temperature for 1 h. Fluorescence values at 665 nm and 620 nm were read using a multi-function microplate reader. The results were imported into Graph Prism, and IC$_{50}$ values were calculated.

Figure 8:
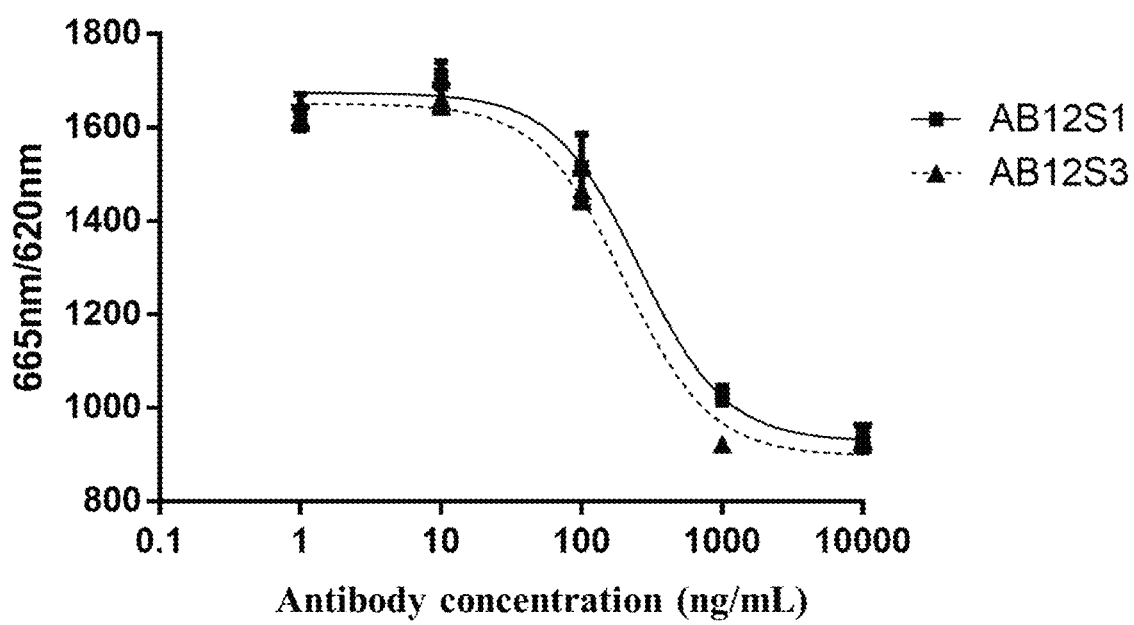
FIG. 8 illustrates measurement of abilities of AB12S1 and AB12S3 to block the binding of TIM-3/Galectin-9 by HTRF.

As shown in FIG. 8, the results show that antibody AB12S3 (IC$_{50}$=202.4 ng/mL) has a stronger ability to block the binding of TIM-3/Galectin-9 than antibody AB12S1 (IC$_{50}$=258.7 ng/mL).

5.7 Detection of an Anti-TIM-3 Humanized Antibody Blocking the Binding of TIM-3/PtdSer The detection of the anti-TIM-3 humanized antibody blocking the binding of TIM-3/PtdSer was performed by a competitive ELISA method.

Detailed experimental steps: PtdSer (purchased from Sigma and with catalog No. P6641) was diluted to 1.3 µM with pH9.6 carbonic acid buffer, and 100 µL/well was added to a microtiter plate overnight at 4° C.; the wells were washed once with 300 µL of PBST, added with 100 µL of PBS solution containing 2% BSA, and blocked for 2 h at 37° C.; AB12S1 and AB12S3 were diluted with a PBST solution containing 2% BSA separately (with a stating concentration of 800 µg/mL, 3 fold serial dilution, a total of 7 concentration gradients), TIM-3 was diluted with the PBST solution containing 2% BSA (to a final concentration of 6 µg/mL), they were mixed at 1:1, and 100 µL was added per well and incubated for 2 h at 37° C.; the wells were washed 3 times with 300 µL of PBST; HRP-labeled anti-6xHis tag mAb (purchased from Biolegend and with catalog No. 652504) was diluted at 1:4000 with the PBST solution containing 2% BSA, and 100 µL were added per well and incubated at 37° C. for 1 h; the wells were washed 5 times with 300 µL of PBST; 100 µL of TMB solution were added to corresponding wells, and developed at room temperature for 20 min; then 50 µL of 1M $H_2SO_4$ solution were added to stop. The absorbance was read by a microplate reader at 450 nm. The results were imported into Graph Prism software and $IC_{50}$ values were calculated.

Figure 9:
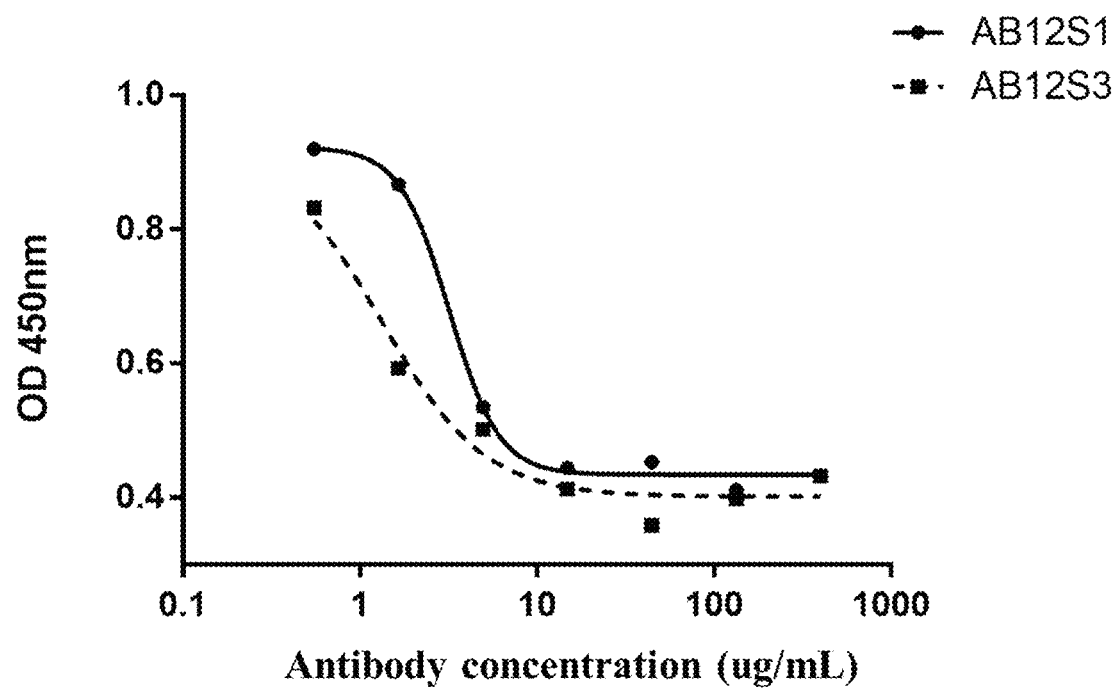
FIG. 9 illustrates measurement of abilities of AB12S1 and AB12S3 to block the binding of TIM-3/PS by competitive ELISA.

As shown in FIG. 9, the results show that AB12S3 ($IC_{50}$=1.33 µg/mL) has a stronger ability to block the binding of TIM-3/PtdSer than AB12S1 ($IC_{50}$=3.20 µg/mL).

5.8 an Anti-TIM-3 Humanized Antibody Enhances the Activation of $CD8^+$ T Cells After quiescent T cells are activated, CD69 is expressed on the surface of cell membranes. The expression of CD69 after $CD8^+$ T cells are stimulated by a superantigen SEB in the presence of the anti-TIM-3 antibody is determined by FACS to evaluate the effect of the anti-TIM-3 antibody in enhancing the function of T lymphocytes. Fresh mononuclear cells (human PBMCs) were obtained from human peripheral blood by a density gradient centrifugation method (Lymphoprep™, human lymphocyte separation solution, STEMCELL), and a T cell sorting reagent (STEMCELL, #19053) was used for obtaining high-purity $CD8^+$ T cells. The obtained $CD8^+$ T cells were re-suspended in a culture medium containing 1 ng/mL Staphylococcal Enterotoxin B (SEB), the cell density was adjusted to $5.6 \times 10^5$/mL, and 180 µL/well ($10^5$ cells/well) were inoculated into a 96-well cell culture plate. Antibodies AB12S3 and AB12S4 were diluted in 10-fold serial dilution, 20 µL were added per well, and AB12S1 was used as positive control. Each sample had three concentrations of 100 µg/mL, 10 µg/mL and 1 µg/mL. Each concentration of each antibody corresponded to 3 replicate wells. After 48 hours, the cells were collected and the expression of CD69 on the surface of $CD8^+$ T cells was detected by FACS. The method was as follows: 300 g of cells were centrifuged for 5 min, the supernatant was discarded, each well was washed with 200 µL of 2% BSA in PBS, the cells were centrifuged, re-suspended with 100 µL/well, 2.5 µL/well of CD69 antibody (BD Company, #555531) were added, the cells were incubated at 4° C. for 1 h, centrifuged, re-suspended in 100 µL of PBS containing 2% BSA, and placed on the machine. The expression of CD69 was detected.

Figure 10:
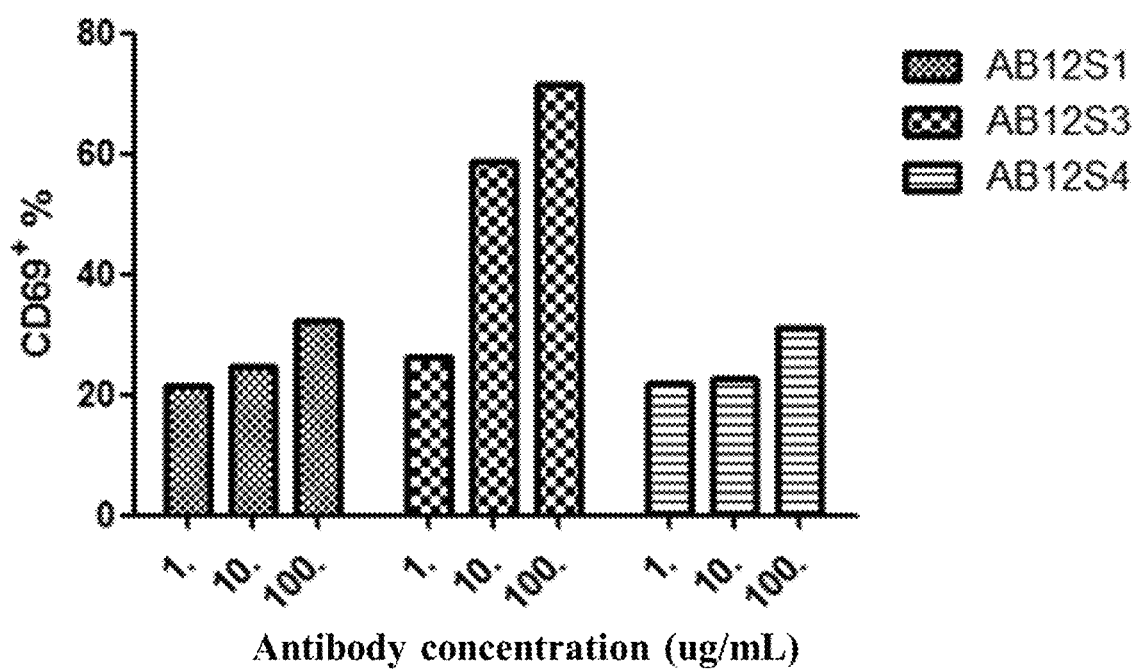
FIG. 10 illustrates effects of AB12S1, AB12S3 and AB12S4 on the expression of CD69 on the surface of CD8$^+$ T cells.

The results are shown in FIG. 10: compared with AB12S1 and AB12S4, AB12S3 significantly up-regulates the expression of CD69 on the surface of $CD8^+$ T cells.

5.9 Ability of an Anti-TIM-3 Humanized Antibody to Stimulate T Cells In Vitro to Kill Tumor Cells A human non-small cell lung cancer cell strain, HCC827 cells (Cell Bank of Chinese Academy of Sciences), and a human breast ductal carcinoma cell strain, HCC1954 cells (Cell Bank of Chinese Academy of Sciences), were inoculated into a 96-well cell culture plate. An anti-TIM-3 humanized antibody AB12S3 with a concentration of 5 µg/mL was added. Isolated serum IgG of a healthy volunteer was used as negative control. Then an anti-CD3 antibody (OKT3) and interleukin-2 (Sino Biological Inc., 11848-HNAY1) activated T cells were added at an effector-target ratio of 4:1 and cultured for 24 hours. Cell proliferation reagent CCK-8 (Dojindo Laboratories) was used for determining the survival of the cells. The survival rate of a culture well without T cells (i.e., a target cell group) was recorded as 100%. The survival of the cells was determined, and a killing rate (%) was calculated by the following formula: Killing rate (%)= (1-OD value of a test group/OD value of the target cell group)×100%. The differences between the three replicate wells of the AB12S3 group and the differences between the three replicate wells of the human IgG group were counted using SPSS, and p values were calculated.

Figure 11:
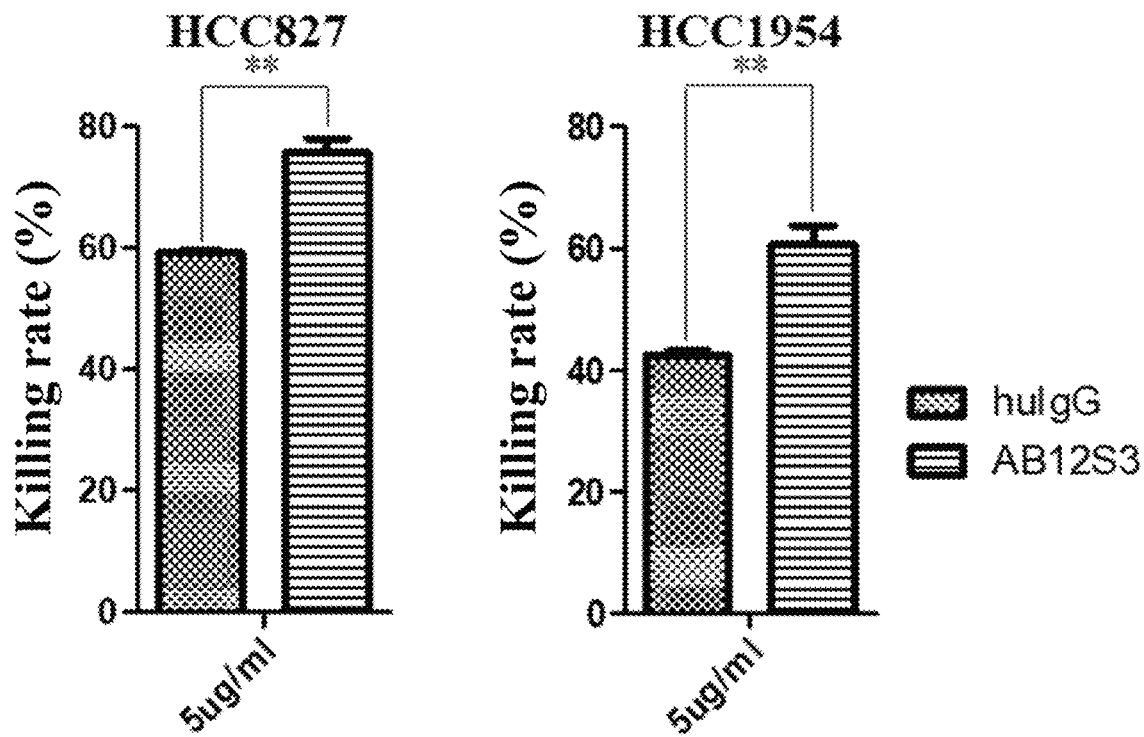
FIG. 11 illustrates an ability of humanized anti-TIM-3 antibody AB12S3 to promote T cells in vitro to kill tumor cells.

The results are shown in FIG. 11. Compared with the HuIgG group, the AB12S3 group has a killing rate for target cells HCC827 that is increased from 59.2% to 75.8% by 27.9% (p<0.01) and has a killing rate for target cells HCC1954 that is increased from 42.4% to 60.8% by 43.3% (p<0.01). Experiments indicate that the anti-TIM-3 humanized antibody AB12S3 can significantly improve the ability of T cells to kill tumor cells.

5.10 Detection of In Vivo Efficacy of the Anti-TIM-3 Humanized Antibody in hTIM3 Transgenic Mice A mouse subcutaneous tumor-bearing model was used for verifying the efficacy of the antibody AB12S3, and a transgenic mouse model was used for evaluation. Each male transgenic mouse (Biocytogen) carrying human TIM-3 at an age of 6-7 weeks was subcutaneously injected with 0.1 mL ($5 \times 10^5$) of MC38 cells. When a tumor volume reached about 100 mm³, the mice were randomly grouped into 3 groups each with 5 mice: a negative control group (normal saline), a 10 mg/kg AB12S1 antibody group, and a 10 mg/kg AB12S3 antibody group. The mice were intraperitoneally administrated once every three days and 6 times in total. Then the tumor volume was measured.

Figure 12:
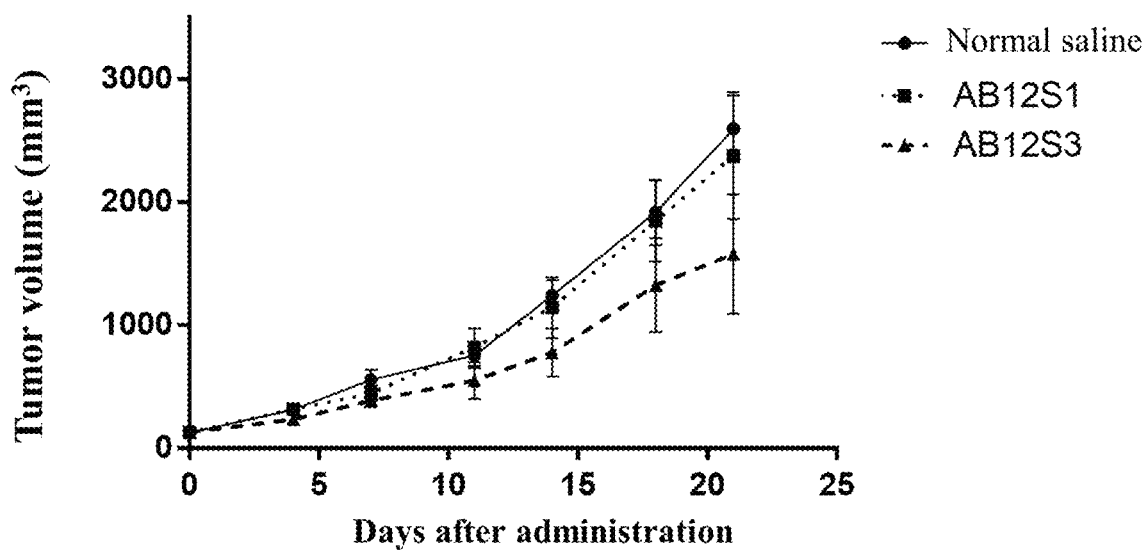
FIG. 12 illustrates in vivo drug efficacy measurement of an antibody AB12S3 and a control antibody AB12S1 in transgenic mice.

The results are shown in FIG. 12. Compared with the negative control group, the antibody AB12S3 has a function of significantly inhibiting tumor growth, but the control antibody AB12S1 has no obvious anti-tumor effect.

5.11 an Effect of an Anti-TIM-3 Humanized Antibody in Promoting SEB to Stimulate PBMCs to Secrete IFN-γ

Figure 13:
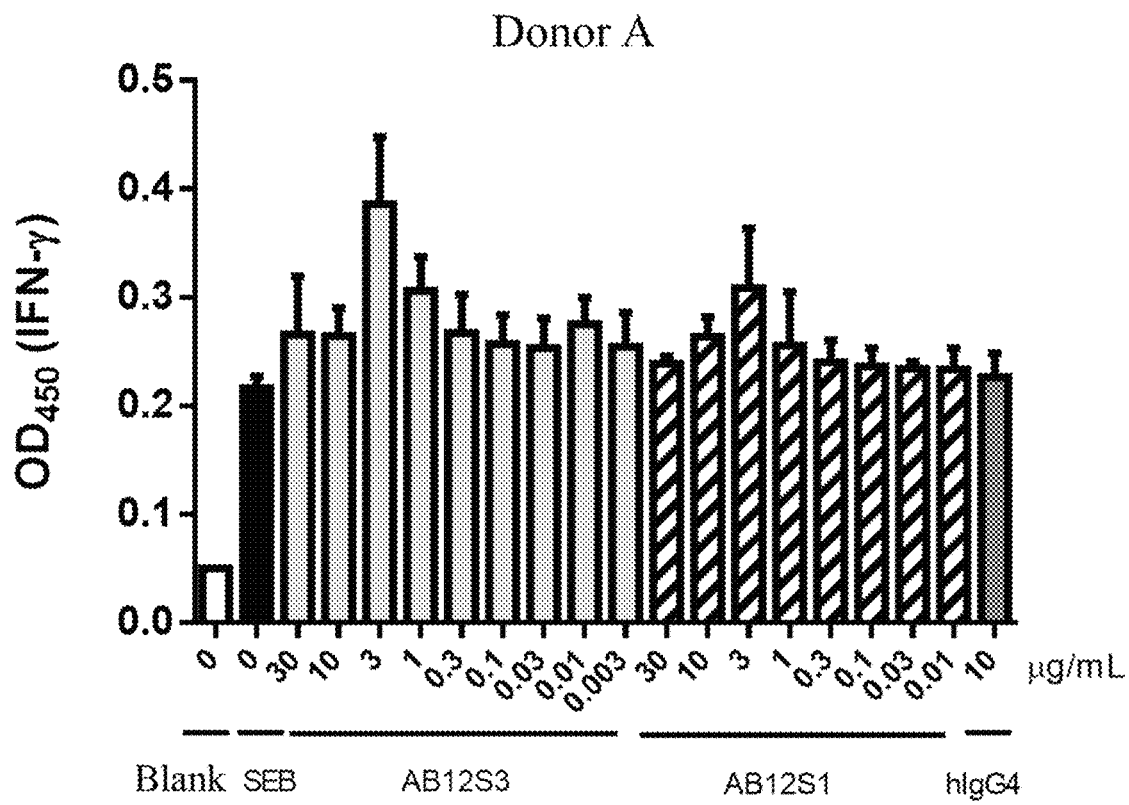
FIG. 13 illustrates effects of a humanized anti-human TIM-3 antibody AB12S3 and a positive control antibody AB12S1 in promoting SEB to stimulate PBMCs derived from donor A to secrete IFN-γ.
Figure 14:
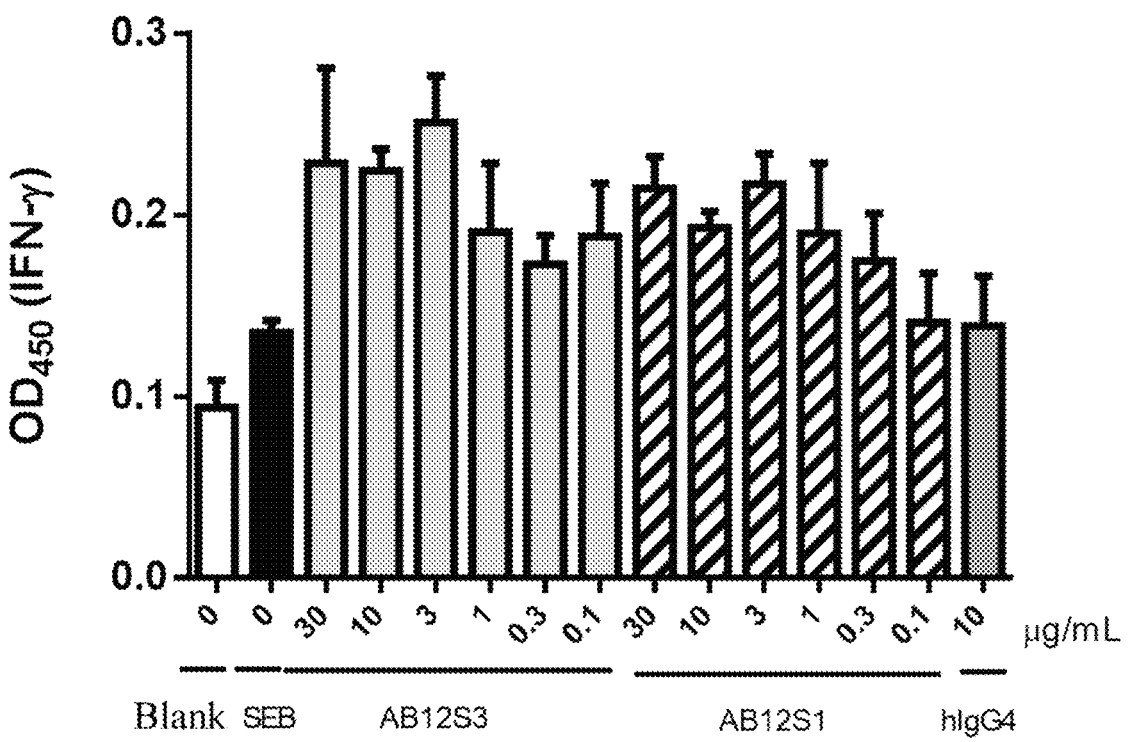
FIG. 14 illustrates effects of a humanized anti-human TIM-3 antibody AB12S3 and a positive control antibody AB12S1 in promoting SEB to stimulate PBMCs derived from donor B to secrete IFN-γ.

TIM-3 can be expressed in activated T cells such as $CD8^+$ T cells, $CD4^+$ T cells and Th1 cells. The anti-TIM-3 antibody inhibits TIM-3 activity by binding to TIM-3 and thus promotes IFN-γ secretion. In this example, SEB was used for stimulating PBMCs (containing T lymphocytes, etc.) to secrete IFN-γ as a detection indicator to detect the activity of the anti-TIM-3 antibody. Fresh mononuclear cells (PBMCs) were obtained from human (donor A and donor B) peripheral blood and inoculated in a 96-well plate. The 1 ng/ml SEB solution, AB12S3 with different concentrations and the control antibody AB12S1 with different concentrations were added and incubated in a 37° C., 5% CO2 incubator for 72 h. After the actions were over, the supernatant was aspirated, and the content of IFN-γ in the supernatant was detected with an IFN-γ detection kit. As shown in FIGS. 13 and 14, AB12S3 significantly promotes the activity of SEB to stimulate PBMCs to secrete IFN-γ, and is superior to the control antibody AB12S1.

5.12 Effect of an Anti-TIM-3 Humanized Antibody on Cytokine Secretion in a Mixed Lymphocyte Reaction (MLR)

Figure 15:
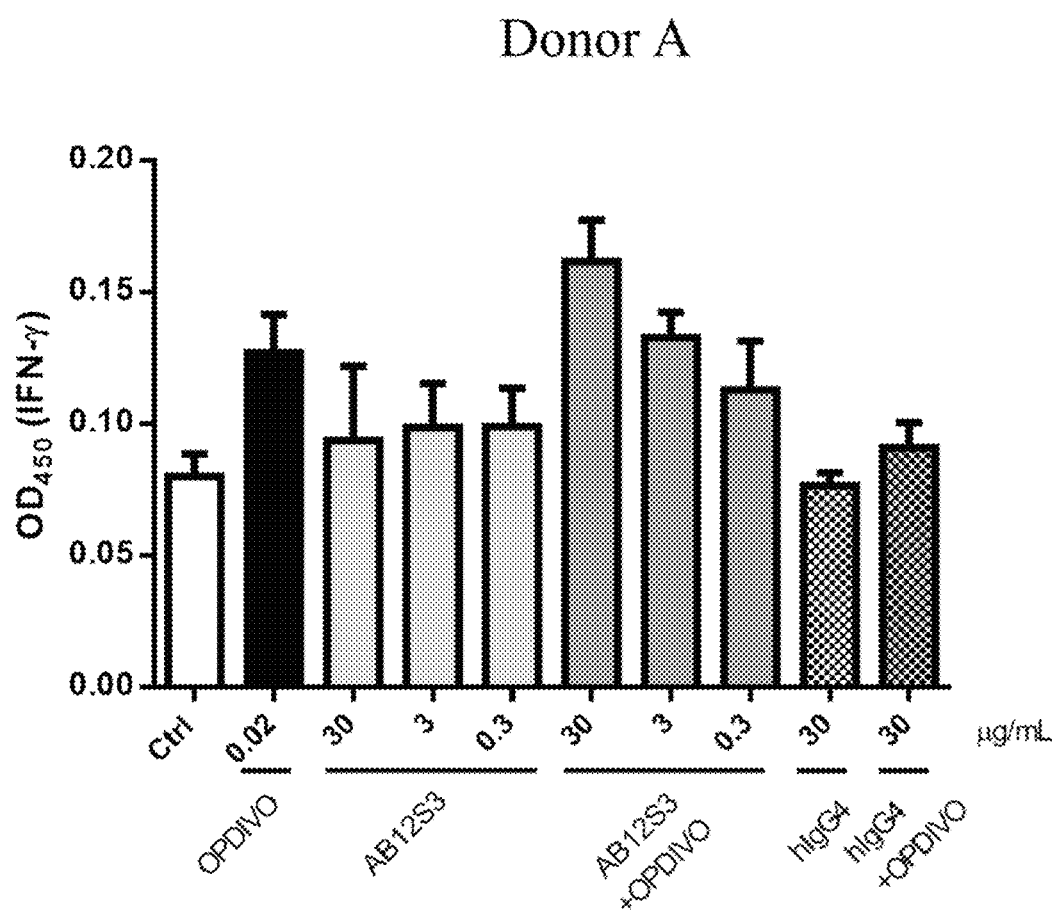
FIG. 15 illustrates effects of a humanized anti-human TIM-3 antibody AB12S3 and the humanized antibody AB12S3 in combination with OPDIVO® in stimulating the secretion of IFN-γ in an MLR of donor A.
Figure 16:
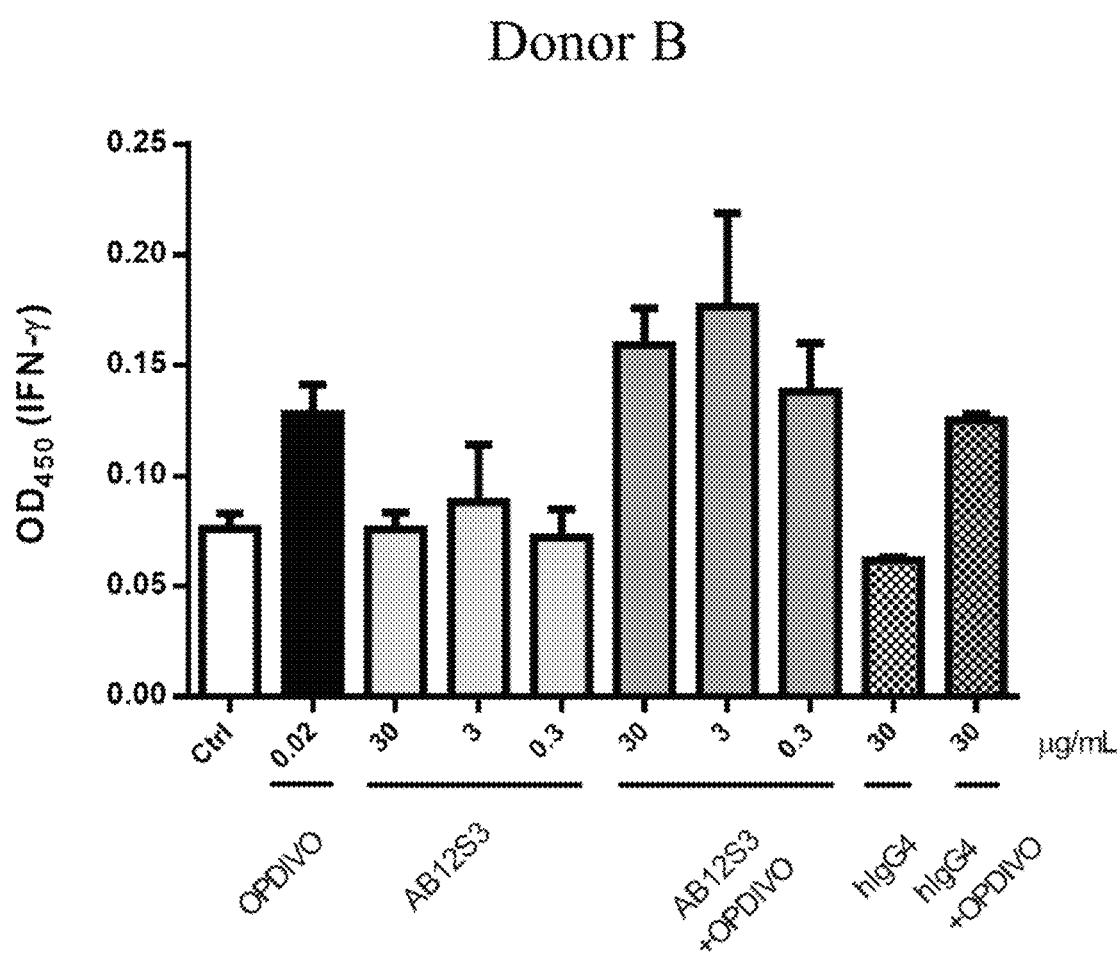
FIG. 16 illustrates effects of a humanized anti-human TIM-3 antibody AB12S3 and the humanized antibody AB12S3 in combination with OPDIVO® in stimulating the secretion of IFN-γ in an MLR of donor B.

CD14$^+$ monocytes were sorted out from PBMCs of donor A and donor B with a CD14 magnetic bead sorting kit, and then induced with GM-CSF and rhIL-4 for 7 days to differentiate into mature dendritic cells (DC). CD4$^+$ T cells were sorted out from the PBMCs with a CD4$^+$ T cell magnetic bead sorting kit, and then mixed with mature DC cells. Different concentrations of AB12S3 were added alone or in combination with OPDIVO® (the concentration of OPDIVO® was 0.02 μg/ml). They were incubated for 5 days in a 37° C. incubator. After the actions were over, the supernatant was aspirated, and the content of IFN-γ in the supernatant was detected with an IFN-γ detection kit. The effects of AB12S3, PD-1 antibody OPDIVO®, and AB12S3 in combination with PD-1 antibody OPDIVO® on the secretion of IFN-γ in the MLR were detected. As shown in FIGS. 15 and 16, AB12S3 in combination with OPDIVO® has a synergistic promotion effect on the secretion of IFN-γ in the MLR.

All the publications mentioned in the present disclosure are incorporated herein by reference as if each publication is separately incorporated herein by reference. In addition, it should be understood that those skilled in the art, who have read the disclosure, can make various changes or modifications on the present disclosure, and these equivalent forms fall within the scope of the appended claims.

| | | |
|---|---|---|
| 0-1 | Form PCT/RO/134 (SAFE) Indications relating to deposited microorganism | |
| 0-1-1 | or other biological material (PCT Rule 13bis) Prepared Using | CEPCT Version 10.20.32 MT/FOP 20140331/0.20.5.21 |
| 0-2 | International application No. | PCT/CN2019/083727 |
| 0-3 | Applicant's or agent's file reference | PCT190361PPC |
| 1 | The indications made below relate to the deposited microorganism or other biological material referred | |
| 1-1 | to in the description | Lines 25 and 26 on page 17; line 30 on |
| 1-2 | on page line | page 39; line 1 on page 40 |
| 1-3 | Identification of deposit | |
| 1-3-1 | Name of depositary institution | China Center for Type Culture Collection |
| 1-3-2 | Address of depositary institution | WuHan University, Wuhan, China, postal code: 430072, Hubei (CN). |
| 1-3-3 | Date of deposit | Oct. 25, 2017 (25. 10. 2017) |
| 1-3-4 | Accession Number | CCTCC C2017181 |
| 1-4 | Additional indications | |
| 1-5 | Designated states for which indications are made | All designated States |
| 1-6 | Indications submitted separately The indications will be submitted to the International Bureau later For receiving Office use only | |
| 0-4 | This sheet was received with the international application (Yes or No) | |
| 0-4-1 | Authorized officer For International Bureau use only | |
| 0-5 | Date of receipt of the record copy by the International Bureau | |
| 0-5-1 | Authorized officer | |

What is claimed is:

1. An antibody or an antigen-binding fragment thereof capable of specifically binding to TIM-3, comprising complementarity determining regions (CDRs) selected from following groups:
   (a) following three CDRs of a heavy chain variable region (VH):
   (i) CDR-H1, which has a sequence of CDR-H1 contained in a VH as shown by SEQ ID NO: 1, or has a sequence with one or more substitutions, deletions or additions relative to the sequence of CDR-H1 contained in the VH;
   (ii) CDR-H2, which has a sequence of CDR-H2 contained in the VH as shown by SEQ ID NO: 1, or has a sequence with one or more substitutions, deletions or additions relative to the sequence of CDR-H2 contained in the VH; and
   (iii) CDR-H3, which has a sequence of CDR-H3 contained in the VH as shown by SEQ ID NO: 1, or has a sequence with one or more substitutions, deletions or additions relative to the sequence of CDR-H3 contained in the VH; and/or
   following three CDRs of a light chain variable region (VL):
   (iv) CDR-L1, which has a sequence of CDR-L1 contained in a VL as shown by SEQ ID NO: 2, or has a sequence with one or more substitutions, deletions or additions relative to the sequence of CDR-L1 contained in the VL;
   (v) CDR-L2, which has a sequence of CDR-L2 contained in the VL as shown by SEQ ID NO: 2, or has a sequence with one or more substitutions, deletions or additions relative to the sequence of CDR-L2 contained in the VL; and
   (vi) CDR-L3, which has a sequence of CDR-L3 contained in the VL as shown by SEQ ID NO: 2, or has a sequence with one or more substitutions, deletions or additions relative to the sequence of CDR-L3 contained in the VL; or
   (b) following three CDRs of a heavy chain variable region (VH):
   (i) CDR-H1, which has a sequence of CDR-H1 contained in a VH as shown by SEQ ID NO: 7, or has a sequence with one or more substitutions, deletions or additions relative to the sequence of CDR-H1 contained in the VH;
   (ii) CDR-H2, which has a sequence of CDR-H2 contained in the VH as shown by SEQ ID NO: 7, or has a sequence with one or more substitutions, deletions or additions relative to the sequence of CDR-H2 contained in the VH; and
   (iii) CDR-H3, which has a sequence of CDR-H3 contained in the VH as shown by SEQ ID NO: 7, or has a sequence with one or more substitutions, deletions or additions relative to the sequence of CDR-H3 contained in the VH; and/or
   following three CDRs of a light chain variable region (VL):
   (iv) CDR-L1, which has a sequence of CDR-L1 contained in a VL as shown by SEQ ID NO: 8, or has a sequence with one or more substitutions, deletions or additions relative to the sequence of CDR-L1 contained in the VL;
   (v) CDR-L2, which has a sequence of CDR-L2 contained in the VL as shown by SEQ ID NO: 8, or has a sequence with one or more substitutions, deletions or additions relative to the sequence of CDR-L2 contained in the VL; and
   (vi) CDR-L3, which has a sequence of CDR-L3 contained in the VL as shown by SEQ ID NO: 8, or has a sequence with one or more substitutions, deletions or additions relative to the sequence of CDR-L3 contained in the VL;

wherein, the substitutions in any one of (i) to (vi) are conservative substitutions;
   wherein, CDR-H1, CDR-H2 and CDR-H3 contained in the heavy chain variable region (VH), and/or CDR-L1, CDR-L2 and CDR-L3 contained in the light chain variable region (VL) are defined by a Kabat, Chothia or IMGT numbering system.

2. The antibody or the antigen-binding fragment thereof according to claim 1, comprising:
   (a) three CDRs contained in a heavy chain variable region (VH) selected from:
   a VH as shown by any one of SEQ ID NO: 1, SEQ ID NO: 3, SEQ ID NO: 5, SEQ ID NO: 7, SEQ ID NO: 9 and SEQ ID NO: 11; and/or
   (b) three CDRs contained in a light chain variable region (VL) selected from:
   a VL as shown by any one of SEQ ID NO: 2, SEQ ID NO: 4, SEQ ID NO: 6, SEQ ID NO: 8, SEQ ID NO: 10 and SEQ ID NO: 12;
   wherein, the three CDRs contained in the heavy chain variable region (VH), and/or the three CDRs contained in the light chain variable region (VL) are defined by the Kabat, Chothia or IMGT numbering system.

3. The antibody or the antigen-binding fragment thereof according to claim 2, comprising:
   (1) three CDRs contained in the heavy chain variable region (VH) as shown by SEQ ID NO: 1, and/or three CDRs contained in the light chain variable region (VL) as shown by SEQ ID NO: 2;
   wherein the three CDRs contained in the heavy chain variable region (VH) and the three CDRs contained in the light chain variable region (VL) are defined by the IMGT numbering system;
   (2) (a) three CDRs contained in the heavy chain variable region (VH) as shown by SEQ ID NO: 1, and/or three CDRs contained in the light chain variable region (VL) as shown by SEQ ID NO: 2; or (b) three CDRs contained in the heavy chain variable region (VH) as shown by SEQ ID NO: 7, and/or three CDRs contained in the light chain variable region (VL) as shown by SEQ ID NO: 8;
   wherein the three CDRs contained in the heavy chain variable region (VH) and the three CDRs contained in the light chain variable region (VL) are defined by the Kabat numbering system; or
   (3) three CDRs contained in the heavy chain variable region (VH) as shown by SEQ ID NO: 1, and/or three CDRs contained in the light chain variable region (VL) as shown by SEQ ID NO: 2;
   wherein the three CDRs contained in the heavy chain variable region (VH) and the three CDRs contained in the light chain variable region (VL) are defined by the Chothia numbering system.

4. The antibody or the antigen-binding fragment thereof according to claim 1, comprising:
(1) CDRs defined by the IMGT numbering system:
(1a) following three heavy chain variable region (VH) CDRs:
(i) CDR-H1, consisting of a sequence as shown by SEQ ID NO: 18, or a sequence with one or more substitutions, deletions or additions relative to the sequence as shown by SEQ ID NO: 18;
(ii) CDR-H2, consisting of a sequence as shown by SEQ ID NO: 19, or a sequence with one or more substitutions, deletions or additions relative to the sequence as shown by SEQ ID NO: 19; and
(iii) CDR-H3, consisting of a sequence as shown by SEQ ID NO: 20, or a sequence with one or more substitutions, deletions or additions relative to the sequence as shown by SEQ ID NO: 20; and/or
(1b) following three light chain variable region (VL) CDRs:
(iv) CDR-L1, consisting of a sequence as shown by SEQ ID NO: 27, or a sequence with one or more substitutions, deletions or additions relative to the sequence as shown by SEQ ID NO: 27;
(v) CDR-L2, consisting of a sequence as shown by SEQ ID NO: 25, or a sequence with one or more substitutions, deletions or additions relative to the sequence as shown by SEQ ID NO: 25; and
(vi) CDR-L3, consisting of a sequence as shown by SEQ ID NO: 23, or a sequence with one or more substitutions, deletions or additions relative to the sequence as shown by SEQ ID NO: 23; or
(2) CDRs defined by the Chothia numbering system:
(2a) following three heavy chain variable region (VH) CDRs:
(i) CDR-H1, consisting of a sequence as shown by SEQ ID NO: 16, or a sequence with one or more substitutions, deletions or additions relative to the sequence as shown by SEQ ID NO: 16;
(ii) CDR-H2, consisting of a sequence as shown by SEQ ID NO: 17, or a sequence with one or more substitutions, deletions or additions relative to the sequence as shown by SEQ ID NO: 17; and
(iii) CDR-H3, consisting of a sequence as shown by SEQ ID NO: 15, or a sequence with one or more substitutions, deletions or additions relative to the sequence as shown by SEQ ID NO: 15; and/or
(2b) following three light chain variable region (VL) CDRs:
(iv) CDR-L1, consisting of a sequence as shown by SEQ ID NO: 24, or a sequence with one or more substitutions, deletions or additions relative to the sequence as shown by SEQ ID NO: 24;
(v) CDR-L2, consisting of a sequence as shown by SEQ ID NO: 25, or a sequence with one or more substitutions, deletions or additions relative to the sequence as shown by SEQ ID NO: 25; and
(vi) CDR-L3, consisting of a sequence as shown by SEQ ID NO: 26, or a sequence with one or more substitutions, deletions or additions relative to the sequence as shown by SEQ ID NO: 26; or
(3) CDRs defined by the Kabat numbering system:
(3a) following three heavy chain variable region (VH) CDRs:
(i) CDR-H1, consisting of a sequence as shown by SEQ ID NO: 13, or a sequence with one or more substitutions, deletions or additions relative to the sequence as shown by SEQ ID NO: 13;
(ii) CDR-H2, consisting of a sequence as shown by SEQ ID NO: 14, or a sequence with one or more substitutions, deletions or additions relative to the sequence as shown by SEQ ID NO: 14; and
(iii) CDR-H3, consisting of a sequence as shown by SEQ ID NO: 15, or a sequence with one or more substitutions, deletions or additions relative to the sequence as shown by SEQ ID NO: 15; and/or
(3b) following three light chain variable region (VL) CDRs:
(iv) CDR-L1, consisting of a sequence as shown by SEQ ID NO: 21, or a sequence with one or more substitutions, deletions or additions relative to the sequence as shown by SEQ ID NO: 21;
(v) CDR-L2, consisting of a sequence as shown by SEQ ID NO: 22, or a sequence with one or more substitutions, deletions or additions relative to the sequence as shown by SEQ ID NO: 22; and
(vi) CDR-L3, consisting of a sequence as shown by SEQ ID NO: 23, or a sequence with one or more substitutions, deletions or additions relative to the sequence as shown by SEQ ID NO: 23; or
(4) CDRs defined by the Kabat numbering system:
(4a) following three heavy chain variable region (VH) CDRs:
(i) CDR-H1, consisting of a sequence as shown by SEQ ID NO: 13, or a sequence with one or more substitutions, deletions or additions relative to the sequence as shown by SEQ ID NO: 13;
(ii) CDR-H2, consisting of a sequence as shown by SEQ ID NO: 28, or a sequence with one or more substitutions, deletions or additions relative to the sequence as shown by SEQ ID NO: 28; and
(iii) CDR-H3, consisting of a sequence as shown by SEQ ID NO: 15, or a sequence with one or more substitutions, deletions or additions relative to the sequence as shown by SEQ ID NO: 15; and/or
(4b) following three light chain variable regions (VL) CDRs:
(iv) CDR-L1, consisting of a sequence as shown by SEQ ID NO: 29, or a sequence with one or more substitutions, deletions or additions relative to the sequence as shown by SEQ ID NO: 29;
(v) CDR-L2, consisting of a sequence as shown by SEQ ID NO: 30, or a sequence with one or more substitutions, deletions or additions relative to the sequence as shown by SEQ ID NO: 30; and
(vi) CDR-L3, consisting of a sequence as shown by SEQ ID NO: 23, or a sequence with one or more substitutions, deletions or additions relative to the sequence as shown by SEQ ID NO: 23;
wherein, the substitutions in any one of (i) to (vi) are conservative substitutions.

5. The antibody or the antigen-binding fragment thereof according to claim 4, wherein
(1) the antibody or an antigen-binding fragment comprises the following six CDRs defined in accordance with the IMGT numbering system: CDR-H1 as shown by SEQ ID NO: 18, CDR-H2 as shown by SEQ ID NO: 19 and CDR-H3 as shown by SEQ ID NO: 20; CDR-L1 as shown by SEQ ID NO: 27, CDR-L2 as shown by SEQ ID NO: 25 and CDR-L3 as shown by SEQ ID NO: 2; or
(2) the antibody or an antigen-binding fragment comprises the following six CDRs defined in accordance with the Chothia numbering system: CDR-H1 as shown by SEQ ID NO: 16, CDR-H2 as shown by SEQ ID NO: 17 and CDR-H3 as shown by SEQ ID NO: 15; CDR-L1 as shown by SEQ ID NO: 24, CDR-L2 as shown by SEQ ID NO: 25 and CDR-L3 as shown by SEQ ID NO: 26; or (3) the antibody or an antigen-binding fragment comprises the following six CDRs defined in accordance with the Kabat numbering system:

(3a) CDR-H1 as shown by SEQ ID NO: 13, CDR-H2 as shown by SEQ ID NO: 14 and CDR-H3 as shown by SEQ ID NO: 15; CDR-L1 as shown by SEQ ID NO: 21, CDR-L2 as shown by SEQ ID NO: 22 and CDR-L3 as shown by SEQ ID NO: 23; or (3b) CDR-H1 as shown by SEQ ID NO: 13, CDR-H2 as shown by SEQ ID NO: 28 and CDR-H3 as shown by SEQ ID NO: 15; CDR-L1 as shown by SEQ ID NO: 29, CDR-L2 as shown by SEQ ID NO: 30 and CDR-L3 as shown by SEQ ID NO: 23.

6. The antibody or the antigen-binding fragment thereof according to claim 1, comprising:
(a) a heavy chain variable region (VH), comprising an amino acid sequence selected from:
(i) a sequence as shown by any one of SEQ ID NOs: 1, 3, 5, 7, 9 and 11;
(ii) a sequence with one or more substitutions, deletions or additions relative to the sequence as shown by any one of SEQ ID NOs: 1, 3, 5, 7, 9 and 11; or
(iii) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by any one of SEQ ID NOs: 1, 3, 5, 7, 9 and 11; and/or
(b) a light chain variable region (VL), comprising an amino acid sequence selected from:
(iv) a sequence as shown by any one of SEQ ID NOs: 2, 4, 6, 8, 10 and 12;
(v) a sequence with one or more substitutions, deletions or additions relative to the sequence as shown by any one of SEQ ID NOs: 2, 4, 6, 8, 10 and 12; or
(vi) a sequence with at least 80%, at least 85%, at least 90%, at least 91%, at least 92%, at least 93%, at least 94%, at least 95%, at least 96%, at least 97%, at least 98%, at least 99% or 100% sequence identity relative to the sequence as shown by any one of SEQ ID NOs: 2, 4, 6, 8, 10 and 12;
wherein, the substitutions in (ii) or (v) are conservative substitutions.

7. The antibody or the antigen-binding fragment thereof according to claim 1, comprising:
(1) a VH having a sequence as shown by SEQ ID NO: 1 and a VL having a sequence as shown by SEQ ID NO: 2;
(2) a VH having a sequence as shown by SEQ ID NO: 3 and a VL having a sequence as shown by SEQ ID NO: 4;
(3) a VH having a sequence as shown by SEQ ID NO: 5 and a VL having a sequence as shown by SEQ ID NO: 6;
(4) a VH having a sequence as shown by SEQ ID NO: 7 and a VL having a sequence as shown by SEQ ID NO: 8;
(5) a VH having a sequence as shown by SEQ ID NO: 9 and a VL having a sequence as shown by SEQ ID NO: 10; or
(6) a VH having a sequence as shown by SEQ ID NO: 11 and a VL having a sequence as shown by SEQ ID NO: 12.

8. The antibody or the antigen-binding fragment thereof according to claim 7, further comprising a heavy chain constant region and a light chain constant region,
wherein the light chain constant region is a κ light chain constant region and the heavy chain constant region is selected from:
(1) a heavy chain constant region of human IgG1;
(2) a heavy chain constant region of human IgG4;
(3) a variant of the heavy chain constant region of human IgG1, wherein, relative to a wild-type sequence from which the variant is derived, the variant has a substitution(s): Leu234Ala, Leu235Ala;
(4) a variant of the heavy chain constant region of human IgG1, wherein, relative to a wild-type sequence from which the variant is derived, the variant has a substitution: Asn297Ala;
(5) a variant of the heavy chain constant region of human IgG1, wherein, relative to a wild-type sequence from which the variant is derived, the variant has a substitution(s): Asp265Ala, Pr391; or
(6) a variant of the heavy chain constant region of human IgG4, wherein, relative to a wild-type sequence from which the variant is derived, the variant has a substitution: Ser228Pro;
wherein amino acid positions above are positions according to an EU numbering system.

9. The antibody or the antigen-binding fragment thereof according to claim 8, wherein the antibody or the antigen-binding fragment thereof comprises a heavy chain constant region (CH) as shown by any one of SEQ ID NOs: 32-37; and, the antibody or the antigen-binding fragment thereof comprises a light chain constant region (CL) as shown by SEQ ID NO: 31.

10. The antibody or the antigen-binding fragment thereof according to claim 1, wherein the antibody or the antigen-binding fragment thereof is a chimeric antibody or a humanized antibody.

11. The antibody or the antigen-binding fragment thereof according to claim 1, wherein the antibody or the antigen-binding fragment thereof is selected from scFv, Fab, Fab', (Fab')$_2$, an Fv fragment, a diabody, a bispecific antibody or a multi-specific antibody.

12. An isolated nucleic acid molecule encoding the antibody or the antigen-binding fragment thereof according to claim 1, or a heavy chain variable region and/or a light chain variable region thereof.

13. A method for preparing the antibody or the antigen-binding fragment thereof according to claim 1, comprising:
culturing a host cell comprising an isolated nucleic acid molecule encoding the antibody or the antigen-binding fragment thereof, or a heavy chain variable region and/or a light chain variable region thereof under a condition where an expression of the antibody or the antigen-binding fragment thereof is allowed, and
recovering the antibody or the antigen-binding fragment thereof from a culture of the cultured host cell.

14. A pharmaceutical composition, comprising the antibody or the antigen-binding fragment thereof according to claim 1.

15. The pharmaceutical composition according to claim 14, further comprising a second antibody that specifically binds to a receptor or a ligand or a nucleic acid encoding the second antibody, wherein the receptor or the ligand is selected from PD-1, PD-L1, PD-L2, LAG-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3 or any combination thereof.

16. The pharmaceutical composition according to claim 14, wherein the pharmaceutical composition further comprises an additional pharmaceutically active agent;
- wherein the additional pharmaceutically active agent is a medicament with anti-tumor activity, wherein the tumor is selected from lung cancer, squamous cell lung cancer, melanoma, renal cancer, breast cancer, IM-TN breast cancer, colorectal cancer, leukemia or a metastatic lesion of the cancer; or
- the additional pharmaceutically active agent is a medicament for treating an infectious disease, wherein the infectious disease is selected from viral infection, bacterial infection, fungal infection and parasitic infection, including but not limited to, HIV, hepatitis virus, herpes virus or sepsis; or
- the additional pharmaceutically active agent is a medicament for treating autoimmune diseases, wherein the autoimmune disease is selected from rheumatoid arthritis, psoriasis, systemic lupus erythematosus, primary biliary cirrhosis, autoimmune hemolytic anemia, autoimmune thrombocytopenic purpura, insulin-dependent diabetes mellitus, Graves' disease, myasthenia gravis, autoimmune hepatitis and multiple sclerosis.

17. A diagnostic or therapeutic kit, comprising the antibody or the antigen-binding fragment thereof according to claim 1 and instructions for use.

18. A method for enhancing an immune response and/or treating a tumor, an infectious disease or an autoimmune disease in a subject, comprising administering to a subject in need thereof an effective amount of the antibody or antigen binding fragment thereof of claim 1, or a pharmaceutical composition comprising the antibody or antigen-binding fragment thereof.

19. The method of claim 18, wherein:
(1) the tumor is selected from lung cancer, squamous cell lung cancer, melanoma, renal cancer, breast cancer, IM-TN breast cancer, colorectal cancer, leukemia or a metastatic lesion of the cancer;
(2) the infectious disease is selected from viral infection, bacterial infection, fungal infection and parasitic infection, including but not limited to, HIV, hepatitis virus, herpes virus or sepsis;
(3) the autoimmune disease is selected from rheumatoid arthritis, psoriasis, systemic lupus erythematosus, primary biliary cirrhosis, autoimmune hemolytic anemia, autoimmune thrombocytopenic purpura, insulin-dependent diabetes mellitus, Graves' disease, myasthenia gravis, autoimmune hepatitis and multiple sclerosis.

20. A hybridoma cell strain, which is:
hybridoma cell strain #22, deposited at China Center for Type Culture Collection (CCTCC) and having a deposit number CCTCC NO. C2017181.

* * * * *

SEQUENCE LISTING

```
<160> NUMBER OF SEQ ID NOS: 47

<210> SEQ ID NO 1
<211> LENGTH: 119
<212> TYPE: PRT
<213> ORGANISM: Mus musculus domesticus

<400> SEQUENCE: 1

Glu Val Gln Leu Gln Leu Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Met His Trp Met Arg Gln Lys Pro Gly Gln Gly Leu Glu Trp Ile
        35                  40                  45

Gly Tyr Ile Asp Pro Asp Asn Asp Gly Ile Lys Tyr Asn Glu Lys Ile
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
```

```
                    85                  90                  95
Ala Arg Asp Phe Gly Tyr Val Asp Trp Phe Pro Tyr Trp Gly Gln Gly
                100                 105                 110

Thr Leu Val Thr Val Ser Ala
        115

<210> SEQ ID NO 2
<211> LENGTH: 107
<212> TYPE: PRT
<213> ORGANISM: Mus musculus domesticus

<400> SEQUENCE: 2

Asp Ile Val Met Thr Gln Ser His Lys Phe Met Ser Thr Ser Val Gly
1               5                   10                  15

Asn Arg Val Ser Ile Thr Cys Lys Ala Ser Gln Asp Val Thr Thr Ala
                20                  25                  30

Val Ala Trp Tyr Gln Gln Lys Ser Gly Gln Ser Pro Lys Leu Leu Ile
            35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Thr
65                  70                  75                  80

Glu Asp Leu Ala Val Tyr Tyr Cys Gln Gln His Tyr Ser Ile Pro Pro
                85                  90                  95

Thr Phe Gly Gly Gly Thr Asn Leu Glu Ile Lys
                100                 105

<210> SEQ ID NO 3
<211> LENGTH: 119
<212> TYPE: PRT
<213> ORGANISM: Artificial sequence
<220> FEATURE:
<223> OTHER INFORMATION: AB12S3-VH

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Met Arg Gln Ala Pro Gly Gln Arg Leu Glu Trp Ile
            35                  40                  45

Gly Tyr Ile Asp Pro Asp Asn Asp Gly Ile Lys Tyr Asn Glu Lys Ile
    50                  55                  60

Lys Gly Lys Ala Thr Leu Thr Ser Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Gly Tyr Val Asp Trp Phe Pro Tyr Trp Gly Gln Gly
                100                 105                 110

Thr Thr Val Thr Val Ser Ser
        115

<210> SEQ ID NO 4
<211> LENGTH: 107
<212> TYPE: PRT
<213> ORGANISM: Artificial sequence
<220> FEATURE:
<223> OTHER INFORMATION: AB12S3-VL
```

<400> SEQUENCE: 4

Asp Ile Val Met Thr Gln Ser Pro Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Gln Gln His Tyr Ser Ile Pro Pro
                85                  90                  95

Thr Phe Gly Gly Gly Thr Lys Val Glu Ile Lys
            100                 105

<210> SEQ ID NO 5
<211> LENGTH: 119
<212> TYPE: PRT
<213> ORGANISM: Artificial sequence
<220> FEATURE:
<223> OTHER INFORMATION: AB12S4-VH

<400> SEQUENCE: 5

Glu Val Gln Leu Val Leu Ser Gly Ala Glu Val Val Lys Pro Gly Ala
1               5                   10                  15

Ser Val Lys Met Ser Cys Lys Ala Ser Gly Tyr Thr Phe Thr Asn Tyr
            20                  25                  30

Val Met His Trp Met Arg Gln Lys Pro Gly Gln Arg Leu Glu Trp Ile
        35                  40                  45

Gly Tyr Ile Asp Pro Asp Asn Asp Gly Ile Lys Tyr Asn Glu Lys Ile
    50                  55                  60

Lys Gly Lys Ala Thr Leu Thr Ser Asp Lys Ser Ser Thr Ala Tyr
65              70                  75                  80

Met Glu Leu Ser Ser Leu Arg Ser Glu Asp Ser Ala Val Tyr Tyr Cys
                85                  90                  95

Ala Arg Asp Phe Gly Tyr Val Asp Trp Phe Pro Tyr Trp Gly Gln Gly
            100                 105                 110

Thr Thr Val Thr Val Ser Ser
        115

<210> SEQ ID NO 6
<211> LENGTH: 107
<212> TYPE: PRT
<213> ORGANISM: Artificial sequence
<220> FEATURE:
<223> OTHER INFORMATION: AB12S4-VL

<400> SEQUENCE: 6

Asp Ile Val Met Thr Gln Ser Pro Ser Met Ser Thr Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Pro
65                  70                  75                  80

Glu Asp Ile Ala Val Tyr Tyr Cys Gln Gln His Tyr Ser Ile Pro Pro
                85                  90                  95

Thr Phe Gly Gly Gly Thr Asn Leu Glu Ile Lys
            100                 105

<210> SEQ ID NO 7
<211> LENGTH: 119
<212> TYPE: PRT
<213> ORGANISM: Artificial sequence
<220> FEATURE:
<223> OTHER INFORMATION: AB12S5-VH

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Arg Gln Ala Pro Gly Gln Arg Leu Glu Trp Met
            35                  40                  45

Gly Trp Ile Asp Pro Asp Asn Asp Gly Ile Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Gly Tyr Val Asp Trp Phe Pro Tyr Trp Gly Gln Gly
            100                 105                 110

Thr Thr Val Thr Val Ser Ser
        115

<210> SEQ ID NO 8
<211> LENGTH: 107
<212> TYPE: PRT
<213> ORGANISM: Artificial sequence
<220> FEATURE:
<223> OTHER INFORMATION: AB12S5-VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Thr Thr Ala
                20                  25                  30

Leu Asn Trp Tyr Gln Gln Lys Pro Gly Lys Ala Pro Lys Leu Leu Ile
            35                  40                  45

Tyr Ser Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Pro
                85                  90                  95

Thr Phe Gly Gly Gly Thr Lys Val Glu Ile Lys
            100                 105

<210> SEQ ID NO 9
<211> LENGTH: 119
<212> TYPE: PRT
<213> ORGANISM: Artificial sequence

<220> FEATURE:
<223> OTHER INFORMATION: AB12S6-VH

<400> SEQUENCE: 9

Gln Val Gln Leu Gln Leu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Arg Gln Ala Pro Gly Gln Arg Leu Glu Trp Met
            35                  40                  45

Gly Trp Ile Asp Pro Asp Asn Asp Gly Ile Lys Tyr Ser Gln Lys Phe
        50                  55                  60

Gln Gly Arg Val Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Gly Tyr Val Asp Trp Phe Pro Tyr Trp Gly Gln Gly
            100                 105                 110

Thr Leu Val Thr Val Ser Ser
            115

<210> SEQ ID NO 10
<211> LENGTH: 107
<212> TYPE: PRT
<213> ORGANISM: Artificial sequence
<220> FEATURE:
<223> OTHER INFORMATION: AB12S6-VL

<400> SEQUENCE: 10

Asp Ile Gln Met Thr Gln Ser Pro Ser Ser Met Ser Ala Ser Val Gly
1               5                   10                  15

Asp Arg Val Thr Ile Thr Cys Gln Ala Ser Gln Asp Val Thr Thr Ala
                20                  25                  30

Leu Asn Trp Tyr Gln Gln Lys Pro Gly Lys Ser Pro Lys Leu Leu Ile
            35                  40                  45

Tyr Ser Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Pro
                85                  90                  95

Thr Phe Gly Gly Gly Thr Asn Leu Glu Ile Lys
            100                 105

<210> SEQ ID NO 11
<211> LENGTH: 119
<212> TYPE: PRT
<213> ORGANISM: Artificial sequence
<220> FEATURE:
<223> OTHER INFORMATION: AB12S7-VH

<400> SEQUENCE: 11

Glu Val Gln Leu Gln Leu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Met Arg Gln Lys Pro Gly Gln Arg Leu Glu Trp Met
            35                  40                  45

Gly Trp Ile Asp Pro Asp Asn Asp Gly Ile Lys Tyr Ser Gln Lys Phe
    50                  55                  60

Gln Gly Arg Val Thr Ile Thr Arg Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Phe Gly Tyr Val Asp Trp Phe Pro Tyr Trp Gly Gln Gly
            100                 105                 110

Thr Leu Val Thr Val Ser Ser
            115

<210> SEQ ID NO 12
<211> LENGTH: 107
<212> TYPE: PRT
<213> ORGANISM: Artificial sequence
<220> FEATURE:
<223> OTHER INFORMATION: AB12S7-VL

<400> SEQUENCE: 12

Asp Ile Val Met Thr Gln Ser Pro Ser Ser Leu Ser Ala Ser Val Gly
 1               5                   10                  15

Asp Arg Val Thr Ile Thr Cys Gln Ala Ser Gln Asp Val Thr Thr Ala
            20                  25                  30

Leu Asn Trp Tyr Gln Gln Lys Ser Gly Gln Ser Pro Lys Leu Leu Ile
        35                  40                  45

Tyr Ser Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Ile Pro Pro
                 85                  90                  95

Thr Phe Gly Gly Gly Thr Asn Leu Glu Ile Lys
            100                 105

<210> SEQ ID NO 13
<211> LENGTH: 5
<212> TYPE: PRT
<213> ORGANISM: Mus musculus domesticus

<400> SEQUENCE: 13

Asn Tyr Val Met His
 1               5

<210> SEQ ID NO 14
<211> LENGTH: 17
<212> TYPE: PRT
<213> ORGANISM: Mus musculus domesticus

<400> SEQUENCE: 14

Tyr Ile Asp Pro Asp Asn Asp Gly Ile Lys Tyr Asn Glu Lys Ile Lys
 1               5                   10                  15

Gly

<210> SEQ ID NO 15
<211> LENGTH: 10
<212> TYPE: PRT
<213> ORGANISM: Mus musculus domesticus

<400> SEQUENCE: 15

Asp Phe Gly Tyr Val Asp Trp Phe Pro Tyr

```
<210> SEQ ID NO 16
<211> LENGTH: 7
<212> TYPE: PRT
<213> ORGANISM: Mus musculus domesticus

<400> SEQUENCE: 16

Gly Tyr Thr Phe Thr Asn Tyr
1               5

<210> SEQ ID NO 17
<211> LENGTH: 6
<212> TYPE: PRT
<213> ORGANISM: Mus musculus domesticus

<400> SEQUENCE: 17

Asp Pro Asp Asn Asp Gly
1               5

<210> SEQ ID NO 18
<211> LENGTH: 8
<212> TYPE: PRT
<213> ORGANISM: Mus musculus domesticus

<400> SEQUENCE: 18

Gly Tyr Thr Phe Thr Asn Tyr Val
1               5

<210> SEQ ID NO 19
<211> LENGTH: 8
<212> TYPE: PRT
<213> ORGANISM: Mus musculus domesticus

<400> SEQUENCE: 19

Ile Asp Pro Asp Asn Asp Gly Ile
1               5

<210> SEQ ID NO 20
<211> LENGTH: 12
<212> TYPE: PRT
<213> ORGANISM: Mus musculus domesticus

<400> SEQUENCE: 20

Ala Arg Asp Phe Gly Tyr Val Asp Trp Phe Pro Tyr
1               5                   10

<210> SEQ ID NO 21
<211> LENGTH: 11
<212> TYPE: PRT
<213> ORGANISM: Mus musculus domesticus

<400> SEQUENCE: 21

Lys Ala Ser Gln Asp Val Thr Thr Ala Val Ala
1               5                   10

<210> SEQ ID NO 22
<211> LENGTH: 7
<212> TYPE: PRT
<213> ORGANISM: Mus musculus domesticus

<400> SEQUENCE: 22

Ser Ala Ser Asn Arg Tyr Ile
1               5
```

```
<210> SEQ ID NO 23
<211> LENGTH: 9
<212> TYPE: PRT
<213> ORGANISM: Mus musculus domesticus

<400> SEQUENCE: 23

Gln Gln His Tyr Ser Ile Pro Pro Thr
1               5

<210> SEQ ID NO 24
<211> LENGTH: 7
<212> TYPE: PRT
<213> ORGANISM: Mus musculus domesticus

<400> SEQUENCE: 24

Ser Gln Asp Val Thr Thr Ala
1               5

<210> SEQ ID NO 25
<211> LENGTH: 3
<212> TYPE: PRT
<213> ORGANISM: Mus musculus domesticus

<400> SEQUENCE: 25

Ser Ala Ser
1

<210> SEQ ID NO 26
<211> LENGTH: 6
<212> TYPE: PRT
<213> ORGANISM: Mus musculus domesticus

<400> SEQUENCE: 26

His Tyr Ser Ile Pro Pro
1               5

<210> SEQ ID NO 27
<211> LENGTH: 6
<212> TYPE: PRT
<213> ORGANISM: Mus musculus domesticus

<400> SEQUENCE: 27

Gln Asp Val Thr Thr Ala
1               5

<210> SEQ ID NO 28
<211> LENGTH: 17
<212> TYPE: PRT
<213> ORGANISM: Artificial sequence
<220> FEATURE:
<223> OTHER INFORMATION: CDR-H2

<400> SEQUENCE: 28

Trp Ile Asp Pro Asp Asn Asp Gly Ile Lys Tyr Ser Gln Lys Phe Gln
1               5                   10                  15

Gly

<210> SEQ ID NO 29
<211> LENGTH: 11
<212> TYPE: PRT
<213> ORGANISM: Artificial sequence
<220> FEATURE:
<223> OTHER INFORMATION: CDR-L1

<400> SEQUENCE: 29
```

```
Gln Ala Ser Gln Asp Val Thr Thr Ala Leu Asn
1               5                   10
```

<210> SEQ ID NO 30
<211> LENGTH: 7
<212> TYPE: PRT
<213> ORGANISM: Artificial sequence
<220> FEATURE:
<223> OTHER INFORMATION: CDR-L2

<400> SEQUENCE: 30

```
Ser Ala Ser Asn Leu Glu Thr
1               5
```

<210> SEQ ID NO 31
<211> LENGTH: 107
<212> TYPE: PRT
<213> ORGANISM: Homo sapiens

<400> SEQUENCE: 31

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 32
<211> LENGTH: 330
<212> TYPE: PRT
<213> ORGANISM: Homo sapiens

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 33
<211> LENGTH: 330
<212> TYPE: PRT
<213> ORGANISM: Artificial sequence
<220> FEATURE:
<223> OTHER INFORMATION: Amino acid sequence of the constant region of
      IgG1 (N297A) mutant

<400> SEQUENCE: 33

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 34
<211> LENGTH: 330
<212> TYPE: PRT
<213> ORGANISM: Artificial sequence
<220> FEATURE:
<223> OTHER INFORMATION: Amino acid sequence of the constant region of
      IgG1(D265A,P329A) mutant

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Ala Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 330
<212> TYPE: PRT
<213> ORGANISM: Artificial sequence
<220> FEATURE:
<223> OTHER INFORMATION: Amino acid sequence of the constant region of
      IgG1 (L234A,L235A) mutant

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
            210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 37
<211> LENGTH: 327
<212> TYPE: PRT
<213> ORGANISM: Artificial sequence
<220> FEATURE:
<223> OTHER INFORMATION: Amino acid sequence of the constant region of
      IgG4(S228P) mutant

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

```
Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 38
<211> LENGTH: 446
<212> TYPE: PRT
<213> ORGANISM: Artificial sequence
<220> FEATURE:
<223> OTHER INFORMATION: AB12S3-HC

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Met Arg Gln Ala Pro Gly Gln Arg Leu Glu Trp Ile
        35                  40                  45

Gly Tyr Ile Asp Pro Asp Asn Asp Gly Ile Lys Tyr Asn Glu Lys Ile
    50                  55                  60

Lys Gly Lys Ala Thr Leu Thr Ser Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Gly Tyr Val Asp Trp Phe Pro Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 39
<211> LENGTH: 1338
<212> TYPE: DNA
<213> ORGANISM: Artificial sequence
<220> FEATURE:
<223> OTHER INFORMATION: AB12S3-HC

<400> SEQUENCE: 39
```

| | |
|---|---:|
| gaggtgcagc tggtgcagtc cggagctgag gtgaagaagc caggagcttc cgtgaaggtg | 60 |
| agctgcaagg cctctggcta cattcacc aactacgtga tgcactggat gagacaggct | 120 |
| ccaggacagc gcctggagtg gatcggctat atcgaccctg ataacgacgg catcaagtac | 180 |
| aatgagaaga tcaagggcaa ggccacactg acctccgata gtccagctc taccgcttac | 240 |
| atggagctgt ccagcctgag aagcgaggac acagccgtgt actattgcgc tgcgatttt | 300 |
| ggctatgtgg actggttccc ctactgggggc cagggcacca cagtgaccgt gtcttccgcc | 360 |
| tctaccaagg gcccttccgt gttccctctg gccccatgtt cccgcagcac ctctgagtcc | 420 |
| acagccgctc tgggctgcct ggtgaaggac tatttcccg agcctgtgac cgtgtcctgg | 480 |
| aacagcggcg ctctgacctc cggagtgcac acatttcccg ccgtgctgca gtcttccggc | 540 |
| ctgtacagcc tgagctctgt ggtgaccgtg ccatccagct ctctgggcac caagacatat | 600 |
| acctgtaacg tggatcataa gccctccaat acaaaggtgg acaagcgcgt ggagagcaag | 660 |
| tacgaccac catgtcctcc atgcccagct cccgagtttc tgggcggccc tagcgtgttc | 720 |
| ctgtttccc ctaagccaaa ggatacccctg atgatcagca ggacccctga ggtgacatgc | 780 |
| gtggtggtgg acgtgtccca ggaggaccca gaggtgcagt tcaactggta cgtggacggc | 840 |
| gtggaggtgc acaatgccaa gaccaagcct cgggaggagc agtttaattc cacctacaga | 900 |
| gtggtgagcg tgctgacagt gctgcatcag gactggctga acggcaagga gtataagtgt | 960 |
| aaggtgtcca ataagggcct gccatccagc atcgagaaga ccatcagcaa ggctaagggc | 1020 |
| cagcccaggg agcctcaggt gtacacactg ccaccctctc aggaggagat gaccaagaac | 1080 |
| caggtgtccc tgacatgcct ggtgaagggc ttctatcctt ccgatatcgc cgtggagtgg | 1140 |
| gagagcaatg gccagccaga gaacaattac aagaccacac ctccagtgct ggattctgac | 1200 |
| ggctccttct tctgtattc ccggctgacc gtggacaaga gcagatgca ggagggcaac | 1260 |
| gtgtttagct gttctgtgat gcatgaggct ctgcacaatc attacacaca gaagtccctg | 1320 | agcctgtctc tgggcaag                                                    1338

<210> SEQ ID NO 40
<211> LENGTH: 214
<212> TYPE: PRT
<213> ORGANISM: Artificial sequence
<220> FEATURE:
<223> OTHER INFORMATION: AB12S3-LC

<400> SEQUENCE: 40

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 642
<212> TYPE: DNA
<213> ORGANISM: Artificial sequence
<220> FEATURE:
<223> OTHER INFORMATION: AB12S3-LC

<400> SEQUENCE: 41
gacatcgtga tgacacagag ccctagctct ctgagcgcct ctgtgggcga tagagtgaca      60
atcacctgta aggcttctca ggacgtgacc acagccgtgg cttggtacca gcagaagccc     120
ggcaaggccc ctaagctgct gatctattcc gctagcaata gatacatcgg cgtgcctgat     180
cgctttaccg gctctggctc cggcacagac tttacattca ccatctccag cctgcagcca     240
gaggacatcg ccacctacta ttgccagcag cattatagca tcccccctac cttcggcggc     300
ggcacaaagg tggagatcaa gaggaccgtg gctgccccct ccgtgttcat ctttccccct     360
tccgatgagc agctgaagtc cggcacagcc agcgtggtgt gcctgctgaa caatttctac     420
cctagagagg ctaaggtgca gtggaaggtg gacaacgccc tgcagagcgg caattctcag     480

```
gagtccgtga ccgagcagga tagcaaggac tctacatatt ccctgtccag cacactgacc    540
ctgagcaagg ctgattacga gaagcacaag gtgtatgcct gtgaggtgac ccatcagggc    600
ctgtcttccc ctgtgacaaa gtctttcaac cggggcgagt gc                      642
```

<210> SEQ ID NO 42
<211> LENGTH: 446
<212> TYPE: PRT
<213> ORGANISM: Artificial sequence
<220> FEATURE:
<223> OTHER INFORMATION: AB12S4-HC

<400> SEQUENCE: 42

| Glu | Val | Gln | Leu | Val | Leu | Ser | Gly | Ala | Glu | Val | Val | Lys | Pro | Gly | Ala |
|---|---|---|---|---|---|---|---|---|---|---|---|---|---|---|---|
| 1 | | | | 5 | | | | | 10 | | | | | 15 | |

Ser Val Lys Met Ser Cys Lys Ala Ser Gly Tyr Thr Phe Thr Asn Tyr
            20                  25                  30

Val Met His Trp Met Arg Gln Lys Pro Gly Gln Arg Leu Glu Trp Ile
        35                  40                  45

Gly Tyr Ile Asp Pro Asp Asn Asp Gly Ile Lys Tyr Asn Glu Lys Ile
    50                  55                  60

Lys Gly Lys Ala Thr Leu Thr Ser Asp Lys Ser Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Asp Phe Gly Tyr Val Asp Trp Phe Pro Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

```
Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 43
<211> LENGTH: 1338
<212> TYPE: DNA
<213> ORGANISM: Artificial sequence
<220> FEATURE:
<223> OTHER INFORMATION: AB12S4-HC

<400> SEQUENCE: 43
gaggtgcagc tggtgctgtc cggagctgag gtggtgaagc aggagcttc cgtgaagatg      60 agctgcaagg cctctggcta tacattcacc aactacgtga tgcactggat gagacagaag    120
ccaggacagc gcctggagtg gatcggctat atcgaccctg ataacgacgg catcaagtac    180
aatgagaaga tcaagggcaa ggccacactg acctccgata gtccagctc taccgcttac    240 atggagctgt ccagcctgag aagcgaggac agcgccgtgt actattgcgc tcgcgatttt    300
ggctatgtgg actggttccc ctactgggc agggcacca cagtgaccgt gtcttccgcc     360
tctaccaagg gccttccgt gttccctctg gccccatgtt cccgcagcac ctctgagtcc    420
acagccgctc tgggctgcct ggtgaaggac tatttcccg agcctgtgac cgtgtcctgg    480
aacagcggcg ctctgacctc cggagtgcac acatttcccg ccgtgctgca gtcttccggc    540
ctgtacagcc tgagctctgt ggtgaccgtg ccatccagct ctctgggcac caagacatat    600
acctgtaacg tggatcataa gcctccaat acaaaggtgg acaagcgcgt ggagagcaag    660
tacggaccac catgtcctcc atgcccagct cccgagtttc tgggcggccc tagcgtgttc    720
ctgtttcccc ctaagccaaa ggatacctg atgatcagca ggacccctga ggtgacatgc    780
gtggtggtgg acgtgtccca ggaggaccca gaggtgcagt tcaactggta cgtggacggc    840
gtggaggtgc acaatgccaa gaccaagcct cgggaggagc agtttaattc cacctacaga    900
gtggtgagcg tgctgacagt gctgcatcag gactggctga acggcaagga gtataagtgt    960
aaggtgtcca ataagggcct gccatccagc atcgagaaga ccatcagcaa ggctaagggc   1020
cagcccaggg agcctcaggt gtacacactg ccaccctctc aggaggagat gaccaagaac   1080
caggtgtccc tgacatgcct ggtgaagggc ttctatcctt ccgatatcgc cgtggagtgg   1140
gagagcaatg ccagccagga gaacaattac aagaccacac tccagtgct ggattctgac   1200 ggctccttct ttctgtattc ccggctgacc gtggacaaga gcagatggca ggagggcaac   1260
gtgtttagct gttctgtgat gcatgaggct ctgcacaatc attacacaca gaagtccctg   1320
agcctgtctc tgggcaag                                                  1338
```

<210> SEQ ID NO 44
<211> LENGTH: 214
<212> TYPE: PRT
<213> ORGANISM: Artificial sequence
<220> FEATURE:
<223> OTHER INFORMATION: AB12S4-LC

<400> SEQUENCE: 44

```
Asp Ile Val Met Thr Gln Ser Pro Ser Ser Met Ser Thr Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Pro
65                  70                  75                  80

Glu Asp Ile Ala Val Tyr Tyr Cys Gln Gln His Tyr Ser Ile Pro Pro
                85                  90                  95

Thr Phe Gly Gly Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 642
<212> TYPE: DNA
<213> ORGANISM: Artificial sequence
<220> FEATURE:
<223> OTHER INFORMATION: AB12S4-LC

<400> SEQUENCE: 45

```
gacatcgtga tgacacagag ccctagctct atgagcacct ctgtgggcga tagagtgaca      60
atcacctgta aggcttctca ggacgtgacc acagccgtgg cttggtacca gcagaagccc     120
ggcaagagcc ctaagctgct gatctattcc gctagcaata gatacatcgg cgtgcctgat     180
cgctttaccg gctctggctc cggcacagac tttacattca ccatctccag cgtgcagcca     240
gaggacatcg ccgtgtacta ttgccagcag cattatagca tccccccctac cttcggcggc     300 ggcacaaatc tggagatcaa gaggaccgtg gctgccccct ccgtgttcat ctttcccccc     360
tccgatgagc agctgaagtc cggcacagcc agcgtggtgt gcctgctgaa caatttctac     420
cctagagagg ctaaggtgca gtggaaggtg gacaacgccc tgcagagcgg caattctcag     480
gagtccgtga ccgagcagga tagcaaggac tctacatatt ccctgtccag cacactgacc     540
```

-continued

```
ctgagcaagg ctgattacga gaagcacaag gtgtatgcct gtgaggtgac ccatcagggc      600
ctgtcttccc ctgtgacaaa gtctttcaac cggggcgagt gc      642
```

<210> SEQ ID NO 46
<211> LENGTH: 448
<212> TYPE: PRT
<213> ORGANISM: Artificial sequence
<220> FEATURE:
<223> OTHER INFORMATION: Amino acid sequence of the VH of AB12S1

<400> SEQUENCE: 46

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Ile Lys Gln Thr Pro Gly Gln Gly Leu Glu Trp Ile
        35                  40                  45

Gly Asp Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Arg Val Gly Gly Ala Phe Pro Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Gln Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Leu His Glu Ala
            420                 425                 430

Leu His Asn His Tyr Thr Gln Lys Ser Leu Ser Leu Ser Pro Gly Lys
            435                 440                 445

<210> SEQ ID NO 47
<211> LENGTH: 218
<212> TYPE: PRT
<213> ORGANISM: Artificial sequence
<220> FEATURE:
<223> OTHER INFORMATION: Amino acid sequence of the VL of AB12S1

<400> SEQUENCE: 47

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Ile Tyr Phe Cys Gln Gln Ser Arg
                85                  90                  95

Lys Asp Pro Ser Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215